United States Patent
Hoelzemann et al.

(10) Patent No.: US 9,273,029 B2
(45) Date of Patent: Mar. 1, 2016

(54) PYRIDINE-AND PYRAZINE DERIVATIVES

(75) Inventors: Guenter Hoelzemann, Seeheim-Jugenheim (DE); Hans-Michael Eggenweiler, Darmstadt (DE); Srinivasa R. Karra, Pembroke, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/118,845

(22) PCT Filed: Apr. 11, 2012

(86) PCT No.: PCT/US2012/032983
§ 371 (c)(1),
(2), (4) Date: Feb. 3, 2014

(87) PCT Pub. No.: WO2012/161877
PCT Pub. Date: Nov. 29, 2012

(65) Prior Publication Data
US 2014/0142097 A1      May 22, 2014

Related U.S. Application Data

(60) Provisional application No. 61/488,997, filed on May 23, 2011.

(51) Int. Cl.
*C07D 401/12* (2006.01)
*A61K 31/444* (2006.01)
*A61K 31/4545* (2006.01)
*A61K 31/496* (2006.01)
*A61K 31/497* (2006.01)
*A61K 31/501* (2006.01)
*A61K 31/5377* (2006.01)
*A61K 45/06* (2006.01)
*C07D 401/14* (2006.01)
*C07D 405/14* (2006.01)
*C07D 409/14* (2006.01)
*C07D 471/04* (2006.01)
*C07D 491/048* (2006.01)
*C07D 409/04* (2006.01)

(52) U.S. Cl.
CPC ............ *C07D 401/12* (2013.01); *A61K 31/444* (2013.01); *A61K 31/4545* (2013.01); *A61K 31/496* (2013.01); *A61K 31/497* (2013.01); *A61K 31/501* (2013.01); *A61K 31/5377* (2013.01); *A61K 45/06* (2013.01); *C07D 401/14* (2013.01); *C07D 405/14* (2013.01); *C07D 409/04* (2013.01); *C07D 409/14* (2013.01); *C07D 471/04* (2013.01); *C07D 491/048* (2013.01)

(58) Field of Classification Search
None
See application file for complete search history.

(56) References Cited

U.S. PATENT DOCUMENTS

| 7,595,319 | B2 | 9/2009 | Berg et al. | |
| 8,198,285 | B2 | 6/2012 | Feng et al. | |
| 2004/0186113 | A1* | 9/2004 | Berg et al. | 514/255.05 |
| 2006/0052396 | A1* | 3/2006 | Berg et al. | 514/255.06 |
| 2006/0173014 | A1 | 8/2006 | Berg et al. | |
| 2007/0213322 | A1 | 9/2007 | Berg et al. | |

FOREIGN PATENT DOCUMENTS

| WO | 03/004472 A1 | 1/2003 |
| WO | 03/004475 A1 | 1/2003 |
| WO | 2004/055005 A1 | 7/2004 |
| WO | 2004/055006 A1 | 7/2004 |
| WO | 2005/079802 A1 | 9/2005 |
| WO | 2007/102770 A1 | 9/2007 |
| WO | 2007/129044 A1 | 11/2007 |
| WO | 2009/030890 A1 | 3/2009 |
| WO | 2009/053737 A2 | 4/2009 |
| WO | 2009/122180 A1 | 10/2009 |
| WO | 2010/071837 A1 | 6/2010 |
| WO | 2010/100431 A1 | 9/2010 |
| WO | 2011/089416 A1 | 7/2011 |

OTHER PUBLICATIONS

Yoshida, Masaru, et al., Study of biodegradable copoly(L-lactic acid/glycolic acid) formulations with controlled release of Z-100 for application in radiation therapy, International Journal of Pharmaceutics, 1995, pp. 61-67, vol. 115.
Alessi Dario R., et al., Molecular basis for the substrate specificity of protein kinase B; comparison with MAPKAP kinase-1 and p70 S6 kinase, FEBS Letters, 1996, pp. 333-338, vol. 399.
Barbie, D.A., et al., Systematic RNA interference reveals that oncogenic KRAS-driven cancers require TBK1, nature, Nov. 5, 2009, pp. 108-114, vol. 462, No. 5.
Berg, Stefan, et al., Discovery of Novel Potent and Highly Selective Glycogen Synthase Kinase-3Beta (GSK3Beta) Inhibitors for Alzheimer's Disease: Design, Synthesis, and Characterization of Pyrazines, Journal of Medicinal Chemistry, Apr. 10, 2012, p. B-E.
Boehm, Jesse S., et al., Integrative Genomic Approaches Identify IKBKE as a Breast Cancer Oncogene, Cell, Jun. 15, 2007, pp. 1065-1079, vol. 129.
Campos-Gonzales, R., et al., Tyrosine Phosphorylation of Mitogen-activated Protein Kinase in Cells with Tyrosine Kinase-negative Epidermal Growth Factor Receptors, The Journal of Biological Chemistry, Jul. 25, 1992, pp. 14535-14538, vol. 267, No. 21.
Chien, Yuchen, et al., RalB GTPase-Mediated Activation of the IkappaB Family Kinase TBK1 Couples Innate Immune Signaling to Tumor Cell Survival, Cell, Oct. 6, 2006, pp. 157-170, vol. 127.
Davies, Stephen P., et al., Specificity and mechanism of action of some commonly used protein kinase inhibitors, Biochem J., 2000, pp. 95-105, vol. 351.

(Continued)

*Primary Examiner* — Timothy R Rozof
(74) *Attorney, Agent, or Firm* — Thomas W. Brown; EMD Serono Research Institute

(57) ABSTRACT

Compounds of the formula (I) in which R, $R^1$ and X have the meanings indicated in claim 1, are inhibitors of TBK1 and IKKε and can be employed, inter alia, for the treatment of cancer and inflammatory diseases

36 Claims, No Drawings

(56) References Cited

OTHER PUBLICATIONS

Eddy, Sean F. et al., Inducible IkappaB Kinase/IkappaB Kinase • Expression is Induced by CK2 and Promotes Aberrant Nuclear Factor- kappaB Activation in Breast Cancer Cells, Cancer Research, 2005, pp. 11375-11383, vol. 65.

Fingl, Edward, et al., The Pharmacological Basis of Therapeutics, Chapter 1, p. 1, Macmillan Publishing Co., Inc., New York, 1975.

Foster, Allan B., et al., Deuterium Isotope Effects in the Metabolism of Drugs and Xenobiotics: Implications for Drug Design, Advances in Drug Research, 1985, pp. 1-40, vol. 14.

Gillette, James R., Theory for the Observed Isotope Effects on the Formation of Multiple Products by Different Kinetic Mechanisms of Cytochrome P450 Enzymes, Biochemistry, 1994, pp. 2927-2937, vol. 33.

Hanzlik, Robert P. et al., Active Site Dynamics of Toluene Hydroxylation by Cytochrome P-450, Journal of Organic Chemistry, 1990, pp. 3992-3997, vol. 55.

Houben-Weyl, Methoden der organischen Chemie [Methods of Organic Chemistry], Georg-Thieme-Verlag, Stuttgart, 1952-1987.

Jarman, Michael, et al., The deuterium isotope effect for the alpha-hydroxylation of tamoxifen by rat liver microsomes accounts for the reduced genotoxicity of [D5-ethyl]tamoxifen, Carcinogenesis, 1995, pp. 683-688, 1995, vol. 16, No. 4.

Khwaja, Asim, et al., Matrix Adhesion and Ras transformation both activate a phosphoinositide 3-OH kinase and protein kinase B/Akt cellular survival pathway, The EMBO Journal, 1997, pp. 2783-2793, Vo. 16, No. 10.

Korherr, Christian, et al., Identification of proangiogenic genes by high-throughput functional genomics: TBK1 and the IRF3 pathway, PNAS, Mar. 14, 2006, pp. 4240-4245, vol. 103., No. 11.

Ou, Yi-Hung, et al., TBK-1 Directly Engages, Akt/PKB Survival Signaling to Support Oncogenic Transformation, Molecular Cell, Feb. 18, 2011, pp. 458-470, vol. 41.

Paquet, Dominik, et al., A zebrafish model of tauopathy allows in vivo imaging of neuronal cell death and drug evaluation, The Journal of Clinical Investigation, May 2009, pp. 1382-1395, vol. 119, No. 5.

Reider, Paul J., et al., Synthesis of (R)-Serine-2-d and Its Conversion to the Broad Spectrum Antibiotic Fludalanine, Journal of Organic Chemistry, 1987, pp. 3326-3334, vol. 52, No. 15.

Ross, Heike, et al., A non-radioactive method for the assay of many serine/threonine-specific protein kinases, Biochem. J., 2002, p. 977-981, vol. 366.

Sills, Matthew A., et al., Comparison of Assay Technologies for a Tyrosine Kinase Assay Generates Different Results in High Throughput Screening, Journal of Biomolecular Screening, 2002, pp. 191-214, vol. 7, No. 3.

Sorg, Gabriele, Automated High Throughput Screening for Serine Kinase Inhibitors Using a LEADSeeker(TM) Scintillation Proximity Assay in the 1536-Well Format, Journal of Biomolecular Screening, 2002, pp. 11-19, 2002, vol. 7.

Tyle, Praveen, Iontophoretic Devices for Drug Delivery, Pharmaceutical Research, 1986, pp. 318-326, vol. 3, No. 6.

Weinstein-Oppenheimer Caroline R., et al., Pharmacology & Therapeutics., 2000, pp. 229-279, vol. 88.

White, Donald E. et al., Oncogene, 2001, pp. 7064-7072, vol. 20.

Chemical Encylopaedia, vol. 4, pp. 990-993, publ. Soviet Encyclopaedia, Moscow, 1988.

\* cited by examiner

PYRIDINE-AND PYRAZINE DERIVATIVES

BACKGROUND OF THE INVENTION

The invention had the object of finding novel compounds having valuable properties, in particular those which can be used for the preparation of medicaments.

The present invention relates to pyridine compounds that are capable of inhibiting one or more kinases. The compounds find applications in the treatment of a variety of disorders, including cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The present invention relates to compounds and to the use of compounds in which the inhibition, regulation and/or modulation of signal transduction by kinases, in particular receptor tyrosine kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

In particular, the present invention relates to compounds and to the use of compounds in which the inhibition, regulation and/or modulation of signal transduction by TBK1 and IKKε plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

IKKε and TBK1 are serine/threonine kinases which are highly homologous to one another and to other IkB kinases. The two kinases play an integral role in the innate immune system. Double-stranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene. In addition, the authors were able to show that IKKε is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defense as proangiogenic factors [C. Korherr et al., PNAS, 103, 4240-4245, 2006]. In 2006, Chien et al. [Y. Chien et al., Cell 127, 157-170, 2006] published that TBK1−/− cells can only be transformed to a limited extent using oncogenic Ras, which suggests an involvement of TBK1 in the Ras-mediated transformation. Furthermore, they were able to show that an RNAi-mediated knock-down of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

IKKε and TBK1 are highly homologous Ser/Thr kinases critically involved in the innate immune response through induction of type 1 interferons and other cytokines. These kinases are stimulated in response to viral/bacterial infection. Immune response to viral and bacterial infection involves the binding of antigens such as bacterial lipopolysaccharide (LPS), viral doublestranded RNS (dsRNA) to Toll like receptors, then subsequent activation of TBK1 pathway. Activated TBK1 and IKKε phosphorylate IRF3 and IRF7, which triggers the dimerization and nuclear translocation of those interferon regulatory transcription factors, ultimately inducing a signaling cascades leading to IFN production.

Recently, IKKε and TBK1 have also been implicated in cancer. It has been shown that IKKε cooperates with activated MEK to transform human cells. In addition, IKKε is frequently amplified/overexpressed in breast cancer cell lines and patient-derived tumors. TBK1 is induced under hypoxic conditions and expressed at significant levels in many solid tumors.

Furthermore, TBK1 is required to support oncogenic Ras transformation, and TBK1 kinase activity is elevated in transformed cells and required for their survival in culture. Similarly, it was found that TBK1 and NF-kB signalling are essential in KRAS mutant tumors. They have identified TBK1 as a synthetic lethal partner of oncogenic KRAS. Lit.:

Y. H. Ou et al., Molecular Cell 41, 458-470, 2011;

D. A. Barbie et al., nature, 1-5, 2009.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore suitable for the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined. The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

In addition, the compounds according to the invention can be used to achieve additive or synergistic effects in certain existing cancer chemotherapies and radiotherapies and/or to restore the efficacy of certain existing cancer chemotherapies and radiotherapies.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a target kinase together in such a manner that the compound can affect the enzyme activity of the kinase either directly; i.e., by interacting with the kinase itself or indirectly; i.e., by interacting with another molecule on which the catalytic activity of the kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

For any compound used in this invention, a therapeutically effective amount, also referred to herein as a therapeutically effective dose, can be estimated initially from cell culture assays. For example, a dose can be formulated in animal models to achieve a circulating concentration range that includes the IC50 or the IC100 as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the LD50 and the ED50. The dose ratio between toxic and therapeutic effect is the therapeutic index and can be expressed as the ratio between LD50 and ED50. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition, (see, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day.

Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

Preferred diseases or disorders that the compounds described herein may be useful in preventing, treating and/or studying are cell proliferative disorders, especially cancer such as, but not limited to, papilloma, blastoglioma, Kaposi's sarcoma, melanoma, lung cancer, ovarian cancer, prostate cancer, squamous cell carcinoma, astrocytoma, head cancer, neck cancer, skin cancer, liver cancer, bladder cancer, breast cancer, lung cancer, uterus cancer, prostate cancer, testis carcinoma, colorectal cancer, thyroid cancer, pancreatic cancer, gastric cancer, hepatocellular carcinoma, leukemia, lymphoma, Hodgkin's disease and Burkitt's disease.

PRIOR ART

Other heterocyclic derivatives and their use as anti-tumour agents have been described in WO 2007/129044.

Other pyridine and pyrazine derivatives have been described in the use for the treatment of cancer in WO 2009/053737 and for the treatment of other diseases in WO 2004/055005.

Other heterocyclic derivatives have been disclosed as IKKε inhibitors in WO 2009/122180.

Pyrrolopyrimidines have been describes as IKKε and TBK1 inhibitors in WO 2010/100431.

Pyrimidine derivatives have been describes as IKKε and TBK1 inhibitors in WO 2009/030890.

SUMMARY OF THE INVENTION

The invention relates to compounds of the formula I

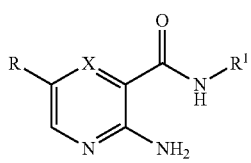

I in which
X denotes CH or N,
R denotes Ar or Het, $R^1$ denotes furyl, thienyl, pyrrolyl, imidazolyl, pyrazolyl, oxazolyl, isoxazolyl, thiazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by Hal, A, $OR^5$, CN, COOA, COOH, $CON(R^5)_2$ and/or $NR^5COA'$, Ar denotes phenyl, biphenyl or naphtyl, each of which is unsubstituted or mono-, di- or trisubstituted by Hal, A, $Het^1$, $(CH_2)_nOR^5$, $(CH_2)_nN(R^5)_2$, $NO_2$, CN, $(CH_2)_nCOOR^5$, $CON(R^5)_2$, $CONH(CH_2)_qNHCOOA'$, $CON[R^5(CH_2)_nHet^1]$, $NR^5COA$, NHCOOA, $NR^5SO_2A$, $COR^5$, $SO_2Het^2$, $SO_2N(R^5)_2$ and/or $S(O)_pA$, Het denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl, 1,3-benzodioxolyl, benzothiophenyl, benzofuranyl or imidazopyridyl, each of which is unsubstituted or mono-, di- or trisubstituted by A, COA, $(CH_2)_pHet^2$, OH, OA, Hal, $(CH_2)_pN(R^5)_2$, $NO_2$, CN, $(CH_2)_pCOOR^5$, $(CH_2)_pCON(R^5)_2$, $NR^5COA$, $(CH_2)_pCOHet^2$ and/or $(CH_2)_pphenyl$, $Het^1$ denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, each of which is unsubstituted or mono-, di- or trisubstituted by A, OH, OA, Hal, CN and/or $(CH_2)_pCOOR^5$, $Het^2$ denotes dihydropyrrolyl, pyrrolidinyl, tetrahydroimidazolyl, dihydropyrazolyl, tetrahydropyrazolyl, dihydropyridyl, tetrahydropyridyl, piperidinyl, morpholinyl, hexahydropyridazinyl, hexahydropyrimidinyl, [1,3]dioxolanyl, piperazinyl, each of which is unsubstituted or monosubstituted by OH and/or A, A' denotes unbranched or branched alkyl having 1-6 C atoms, in which 1-7 H atoms may be replaced by F, A denotes unbranched or branched alkyl having 1-10 C atoms, in which one or two non-adjacent CH and/or $CH_2$ groups may be replaced by N, O, S atoms and/or by —CH=CH— groups and/or in addition 1-7 H atoms may be replaced by F, $R^5$ denotes H or unbranched or branched alkyl having 1-6 C atoms, in which 1-7 H atoms may be replaced by F, Hal denotes F, Cl, Br or I,
n denotes 0, 1, 2, 3 or 4,
p denotes 0, 1 or 2,
q denotes 1, 2, 3 or 4, and pharmaceutically usable salts, tautomers and stereoisomers thereof, including mixtures thereof in all ratios.

The invention also relates to the optically active forms (stereoisomers), salts, the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides. Of course, the invention also relates to the solvates of the salts.

The term pharmaceutically usable derivatives is taken to mean, for example, the salts of the compounds according to the invention and also so-called prodrug compounds. The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to claims 1-12 and pharmaceutically usable salts, tautomers and stereoisomers thereof, characterised in that
a) a compound of the formula II

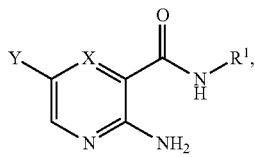

in which Y denotes an Br or I,
X and $R^1$ have the meanings indicated in Claim 1,
is reacted with a compound of formula III

R-L     III in which R has the meaning indicated in Claim1 and
L denotes a boronic acid or a boronic acid ester group,
or
b) a compound of the formula IV

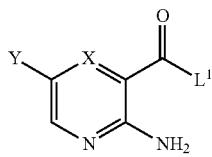

in which R and X have the meanings indicated in Claim 1 and
$L^1$ denotes Cl, Br, I or a free or reactively functionally modified OH group,
is reacted with a compound of the formula V $R^1$—$NH_2$     V in which $R^1$ has the meaning indicated in Claim 1,
or
c) that it is liberated from one of its functional derivatives by treatment with a solvolysing or hydrolysing agent,
and/or a base or acid of the formula I is converted into one of its salts.

Above and below, the radicals $R^1$, R and X have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two CH and/or $CH_2$ groups in A may also be replaced by N, O or S atoms and/or by —CH=CH— groups. A thus also denotes, for example, 2-methoxyethyl. More preferably, A denotes unbranched or branched alkyl having 1-6 C atoms, in which one or two non-adjacent CH and/or $CH_2$ groups may be replaced by N and/or O atoms and/or in addition 1-7 H atoms may be replaced by F.

A' denotes alkyl, is unbranched (linear) or branched, and has 1, 2, 3, 4, 5 or 6 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A' preferably denotes alkyl having 1, 2, 3 or 4 C atoms, preferably methyl, ethyl, propyl, isopropyl, butyl, isobutyl, sec-butyl, tert-butyl or trifluoromethyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Ar particularly preferably denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$.

Het preferably denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl.

Het¹ preferably denotes pyrazolyl or imidazolyl, each of which is unsubstituted or monosubstituted by A.

Het² preferably denotes pyrrolidinyl, piperidinyl, morpholinyl, [1,3]dioxolanyl, piperazinyl, each of which is unsubstituted or monosubstituted by OH and/or A.

R¹ preferably denotes pyridyl, pyrimidyl, pyridazinyl or furo[3,2-b]pyridyl, each of which is unsubstituted or monosubstituted by Hal, A, OR⁵, COOA, COOH, CON(R⁵)₂ and/or NR⁵COA'.

R⁵ preferably denotes H, alkyl having 1, 2, 3 or 4 C atoms, more preferably H, methyl, ethyl, propyl, isopropyl, butyl, isobutyl, sec-butyl, tert-butyl or trifluoromethyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail have the meaning indicated for the formula I, but in which in Ia R¹ denotes pyridyl, pyrimidyl, pyridazinyl or furo[3,2-b]pyridyl, each of which is unsubstituted or monosubstituted by Hal, A, OR⁵, COOA, COOH, CON(R⁵)₂ and/or NR⁵COA';

in Ib Ar denotes phenyl, biphenyl or naphtyl, each of which is unsubstituted or mono-, di- or trisubstituted by A, Hal, Het¹, COR⁵, CON(R⁵)₂, CONH(CH₂)ₑNHCOOA', CON[R⁵(CH₂)ₙHet¹], NHCOOA, (CH₂)ₙN(R⁵)₂, (CH₂)ₙOR⁵, (CH₂)ₙCOOR⁵, SO₂Het² and/or SO₂N(R⁵)₂;

in Ic Het denotes thienyl, pyrazolyl, pyridyl, each of which is unsubstituted or mono- or disubstituted by A, (CH₂)ₚHet², (CH₂)ₚCON(R⁵)₂ and/or (CH₂)ₚphenyl;

in Id Het¹ denotes pyrazolyl or imidazolyl, each of which is unsubstituted or monosubstituted by A;

in Ie Het² denotes pyrrolidinyl, piperidinyl, morpholinyl, [1,3]dioxolanyl, piperazinyl, each of which is unsubstituted or monosubstituted by OH and/or A;

in If A denotes unbranched or branched alkyl having 1-6 C atoms, in which one or two non-adjacent CH and/or CH₂ groups may be replaced by N and/or O atoms and/or in addition 1-7 H atoms may be replaced by F;

in Ig X denotes CH oder N,
R denotes Ar or Het,
R¹ denotes pyridyl, pyrimidyl, pyridazinyl or furo[3,2-b]pyridyl, each of which is unsubstituted or monosubstituted by Hal, A, OR⁵, COOA, COOH, CON(R⁵)₂ and/or NR⁵COA',
Ar denotes phenyl, biphenyl or naphtyl, each of which is unsubstituted or mono-, di- or trisubstituted by A, Hal, Het¹, COR⁵, CON(R⁵)₂, CONH(CH₂)ₑNHCOOA', CON[R⁵(CH₂)ₙHet¹], NHCOOA, (CH₂)ₙN(R⁵)₂, (CH₂)ₙOR⁵, (CH₂)ₙCOOR⁵, SO₂Het² and/or SO₂N(R⁵)₂,
Het denotes thienyl, pyrazolyl, pyridyl, each of which is unsubstituted or mono- or disubstituted by A, (CH₂)ₚHet², (CH₂)ₚCON(R⁵)₂ and/or (CH₂)ₚphenyl,
Het¹ denotes pyrazolyl or imidazolyl, each of which is unsubstituted or monosubstituted by A,
Het² denotes pyrrolidinyl, piperidinyl, morpholinyl, [1,3]dioxolanyl, piperazinyl, each of which is unsubstituted or monosubstituted by OH and/or A,
A' denotes unbranched or branched alkyl having 1-6 C atoms, in which 1-7 H atoms may be replaced by F,
A denotes unbranched or branched alkyl having 1-6 C atoms, in which one or two non-adjacent CH and/or CH₂ groups may be replaced by N and/or O atoms and/or in addition 1-7 H atoms may be replaced by F,
R⁵ denotes H or unbranched or branched alkyl having 1-6 C atoms, in which 1-7 H atoms may be replaced by F,
Hal denotes F, Cl, Br or I,
n denotes 0, 1, 2, 3 or 4,
p denotes 0, 1 or 2,
q denotes 1, 2, 3 or 4,
and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II with a compound of formula III.

The compounds of the formula II and of formula III are generally known. If they are novel, however, they can be prepared by methods known per se.

The reaction is carried out under standard conditions known as Suzuki reaction to the skilled artisan.

In the compounds of the formula III, L preferably denotes

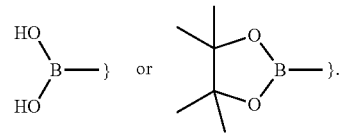

Depending on the conditions used, the reaction time is between a few minutes and 14 days, the reaction temperature is between about −30° and 140°, normally between 0° and 110°, in particular between about 60° and about 110°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, imethoxyethane, acetonitrile, dichloromethane, DMF and/or water.

Furthermore, compounds of the formula I can preferably be obtained by reacting a compound of the formula IV with a compound of the formula V.

The compounds of the formula IV and of formula V are generally known. If they are novel, however, they can be prepared by methods known per se.

In the compounds of the formula IV, $L^1$ preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

The cleavage of an ether is carried out by methods as are known to the person skilled in the art.

A standard method of ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar.

Esters can be saponified, for example, using acetic acid or using NaOH or KOH in water, water/THF or water/dioxane, at temperatures between 0 and 100°.

Alkylations on the nitrogen are carried out under standard conditions, as are known to the person skilled in the art.

The compounds of the formulae I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' denotes an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" denotes a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl, tolyl; aryloxyalkanoyl, such as POA; alkoxycarbonyl, such as methoxycarbonyl, ethoxycarbonyl, 2,2,2-tri-chloroethoxycarbonyl, BOC, 2-iodoethoxycarbonyl; aralkoxycarbonyl, such as CBZ ("carbobenzoxy"), 4-methoxybenzyloxycarbonyl, FMOC; arylsulfonyl, such as Mtr, Pbf, Pmc. Preferred amino-protecting groups are BOC and Mtr, furthermore CBZ, Fmoc, benzyl and acetyl.

The expression "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5 N HCl in dioxane at 15-30°, the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalene-sulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)-methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; $di(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other iso-topes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and the pharmaceutically usable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the pharmaceutically usable salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or the pharmaceutically usable salts, tautomers and stereoisomers thereof, including mixtures thereof in all ratios, and at least one further medicament active ingredient.

The invention also relates to a set (kit) consisting of separate packs of (a) an effective amount of a compound of the formula I and/or the pharmaceutically usable salts, tautomers and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or the pharmaceutically usable salts, tautomers and stereoisomers thereof, including mixtures thereof in all ratios, and an effective amount of a further medicament active ingredient in dissolved or lyophilised form.

Use

The invention relates to the compounds of formula I for the use for the treatment of cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The invention relates to the use of compounds of formula I for the preparation of a medicament for the treatment of cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

The invention relates to a method of treating a mammal having a disease selected from cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease, wherein the method comprises administering to a mammal a therapeutically effective amount of a compound of formula I.

The present compounds are suitable as pharmaceutical active ingredients for mammals, especially for humans, in the treatment and control of cancer diseases and inflammatory diseases.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

The present invention encompasses the use of the compounds of the formula I and/or physiologically acceptable salts, tautomers and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts, tautomers and solvates thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the cancer disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamine-platinum(II)]bis[diamine(chloro)platinum(II)] tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(di-methylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylene-dioxy)-5-methyl-7-hydroxy-8-methoxybenzo[c]phenanthridinium, 6,9-bis[[(2-amino-ethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Test for the Inhibition of IKKε

IKKε—Kinase Assay (IKKepsilon)
Summary

The kinase assay is performed either as 384-well Flashplate assay (for e.g. Topcount measurement). 1 nM IKKε, 800 nM biotinylated IκBα(19-42) peptide (Biotin-C6-C6-GLK-KERLLDDRHDSGLDSMKDEE) SEQ ID NO: 1 and 10 μM ATP (spiked with 0.3 μCi $^{33}$P-ATP/well) are incubated in a total volume of 50 μl (10 mM MOPS, 10 mM Mg-acetat, 0.1 mM EGTA, 1 mM Dithiothreitol, 0.02% Brij35, 0.1% BSA, 0.1% BioStab, pH 7.5) with or without test compound for 2 hours at 30° C. The reaction is stopped with 25 μl 200 mM EDTA. After 30 Min at room temperature the liquid is removed and each well washed thrice with 100 μl 0.9% sodium chloride solution. Non-specific reaction is determined in presence of 3 μM MSC2119074 (BX-795). Radioactivity is measured with Topcount (PerkinElmer). Results (e.g. IC$_{50}$-values) are calculated with program tools provided by the IT-department (e.g. AssayExplorer, Symyx).

Test for the Inhibition of TBK1

Enzyme Test
Summary

The kinase assay is performed as 384-well Flashplate assay (for e.g. Topcount measurement. 0.6 nM TANK binding kinase (TBK1), 800 nM biotinylated MELK-derived peptide (Biotin-Ah-Ah-AKPKGNKDYHLQTCCGSLAYRRR) SEQ ID NO: 2 and 10 μM ATP (spiked with 0.25 μCi $^{33}$P-

ATP/well) are incubated in a total volume of 50 µl (10 mM MOPS, 10 mM Mg-acetat, 0.1 mM EGTA, 1 mM DTT, 0.02% Brij35, 0.1% BSA, pH 7.5) with or without test compound for 120 Min at 30° C. The reaction is stopped with 25 µl 200 mM EDTA. After 30 Min at room temperature the liquid is removed and each well washed thrice with 100 µl 0.9% sodium chloride solution. Nonspecific reaction is determined in presence of 100 nM Staurosporine. Radioactivity is measured in a Topcount (PerkinElmer). Results (e.g. $IC_{50}$-values) are calculated with program tools provided by the IT-department (e.g. AssayExplorer, Symyx).

Cell Test

Dose Response Inhibition of Phospho-IRF3 @ Ser 386 cell/MDAMB468/INH/PHOS/IMAG/pIRF3

1. Scope

Although TBK1 and IKKε are best known as key players in the innate immune response, recent findings have pointed towards a role for TBK1 and IKKε in Ras-induced oncogenic transformation. TBK1 was identified as a RalB effector in the Ras-like (Ral)-guanine nucleotide exchange factor (GEF) pathway that is required for Ras-induced transformation. TBK1 directly activates IRF3 which, upon phosphorylation, homodimerizes and translocates to the nucleus where it activates processes involved with inflammation, immune regulation, cell survival and proliferation.

This assay has been devised in order to assess the efficacy/potency of TBK1/IKKε inhibitor compounds based on the immunocytochemical detection of nuclear localised phospho-IRF3, a target directly downstream of TBK1.

Treatment with Polyinosine-polycytidylic acid (poly(I:C), a synthetic analog of doublestranded RNA (dsRNA), a molecular pattern associated with viral infection which is recognized by Toll-like receptor 3 (TLR3) is used to induce TBK1/IKKε activity and IRF3 phosphorylation at Ser386.

2. Assay Overview

Day 1: MDA-MB-468 cells are detached with HyQ-Tase, counted, and seeded into a 384-well clear bottom TC-surface plate at density of 10,000 cells per well in a total volume of 35 ul complete medium. Alternatively cells are directly seeded from frozen vials.

Day 2: Cells are pre-treated with inhibitor compounds for 1 h prior to Poly(I:C) stimulation. After 2 h of incubation with Poly(I:C), cells are fixed in (para)formaldehyde (PFA) and permeabilized with methanol (MeOH). The cells are then blocked and incubated with an anti-pIRF3 antibody at 4oC overnight.

Day 3: The primary antibody is washed off, an AlexaFluor488-conjugated secondary is added, cells are counterstained with propidium iodide followed by image acquisition on IMX Ultra high content reader.

3. Reagents, Materials cells: ATCC HTB 132, Burger lab (MP-CB 2010-327 or MDA-MB-468/10)

plating medium=culture medium:
  RPMI 1640, Invitrogen # 31870
  10% FCS, Invitrogen # 10270-106
    2 mM Glutamax, Invitrogen #35050-038
    1 mM Natrium-Pyruvat, Invitrogen # 11360
    1% Pen/Strep
  37° C., 5% CO2 plates: black/clear bottom 384well bottom cell culture plates, Falcon #35 3962 or Greiner #781090 subcultivation: HyQ-Tase, Thermo Scientific (HyClone) # SV30030.01 other reagents:

Poly(I:C) (LMW), Invivogen # tlrl-picw (prepare 20 mg/ml stock in sterile PBS, denature 30 min 55oC in waterbath, slowly cool to RT, store at −20 oC in aliquots)

reference inhibitor: MSC2119074A-4=BX-795 (IC50: 200-800 nM)
  inhibitory control: 10 µM MSC2119074A-4=BX-795
  neutral control: 0.5% DMSO a 10point dose-response curve with MSC2119074A-4=BX-795 is included in each experiment Hepes, Merck #1.10110

PBS 1×DPBS, Invitrogen # 14190

Formaldehyde (methanol-free, 16%, ultrapure EM Grade), Polysciences # 18814 (storage RT), final conc.: 4%

Methanol, Merck # 1.06009.1011 (−20 oC pre-cooled)

Goat Serum, PAA # B15-035 (storage 4 oC, long time −20 oC), final conc.: 10%

BSA (IgG and Protease free, 30%), US-Biological # A1317(storage 4 oC, long time −20 oC), final conc.: 2%

Tween 20 Detergent, Calbiochem # 655204 (storage RT), (prepare 10% stock in water; final conc.: 0.1%)

anti-pIRF-3 Rabbit mAb, Epitomics # 2526-B (storage −20 oC), final conc.: 1:2000 in PBS/2% BSA Alexa Fluor Goat-anti-Rabbit-488, Invitrogen # A11034 or # A11008 (storage 4 oC, dark), final conc.: 1:2000 in PBS/2% BSA/0.1% Tween Propidium Iodide (PI), Fluka # 81845, 1 mg/ml in H2O (storage 4 oC, dark), final conc.: 0.2 µg/ml 4. Procedure Seed 10,000 cells/walls/35ul of complete RPMI + 10% FCS into black/clear bottom 384 well bottom cell culture plates

↓

Incubate for 2 h at room temperature on the bench followed by further incubation for 22 h at 37° C., 5% CO$_2$ and 90% rH

↓ compound treatment: Add 5µl prediluted compounds, standard or control reagents (8 fold conc.)
cpd. dilution from DMSO stocks in 20mM Hepes pH 7.2;
final DMSO conc.: 0.5% serial dilution of cpds from
10mM stocks (Remp) 10 steps, 3.16 fold in DMSO
30µM 9.49 µM 3µM 0.95µM 0.3µM
0.095µM 0.03µM 0.0095µM 0.003µM 0.00095µM
Incubate for 60 minutes at 37° C., 5% CO$_2$ and 90% rH

↓ stimulation treatment: Add 10µl Poly (I:C) to all wells except for unstimulated controls such that a final concentration of 100ug/ml is achieved (stock 20mg/ml → 1:40 in PBS) (5 fold conc.) Incubate for 120 minutes at 37° C., 5% CO$_2$ and 90% rH

↓ completely aspirate supernatant

↓

-continued
Fix cells: Add 100µl 4% Paraformaldehyde in PBS
Incubate for 15 minutes at RT

↓

Wash 3x with 80µl PBS (Tecan powerwasher),
completely aspirate supernatant
put plate on ice

↓

Permeabilize cells: Quickly add 100µl-20° C. cold MeOH
(pre-cool reservoir)
Incubate for 10 minutes at RT or 4° C.

↓

Wash once with 80µl PBS (Tecan powerwasher),
completely aspirate supernatant

↓

Block non-specific binding: Add 30µl 10% goat serum in
PBS/2% BSA
Shake on Multidrop Combi (17 seconds)
Incubate for 60 minutes at 37° C.

↓

Completely aspirate supernatant

↓

Primary staining: Add 25µl of primary antibody diluted 1:2000 in
PBS/2% BSA
Shake on Multidrop Combi (17 seconds)
Incubate O/N at 4° C.

↓

Wash 3x with 80µl PBS (Tecan powerwasher),
completely aspirate supernatant

↓

Secondary staining and nuclear staining: Add 25µl of secondary
antibody (1:2000)
and
0.2µg/ml Propidium iodide in PBS/2% BSA/0.1% Tween
Shake on Multidrop Combi (17 seconds)
Incubate for 75 minutes at 37° C.

↓

Wash 3x with 80µl PBS (Tecan powerwasher),
completely aspirate supernatant

↓

Dispense 80µl PBS into all wells

↓

-continued
Seal plates with transparent adhesive seals

↓

Image aquisition at IMX Ultra (Metaexpress 3.1. scan settings
TBK_10x_pin8)

↓

Image analysis (Metaexpress 3.1. <cell scoring>, TBK1-Cellscoring)

↓ data analysis and reporting with Assay explorer

HPLC/MS conditions:
column: Chromolith Speed ROD RP-18e, 50×4.6 mm$^2$
gradient: A:B=96:4 to 0:100
flow rate: 2.4 ml/min
eluent A: water+0.05% formic acid
eluent B: acetonitrile+0.04% formic acid
wavelength: 220 nm
mass spectroscopy: positive mode
$^1$H NMR: coupling constant J [Hz].

Preferred general scheme for manufacturing compounds of formula I

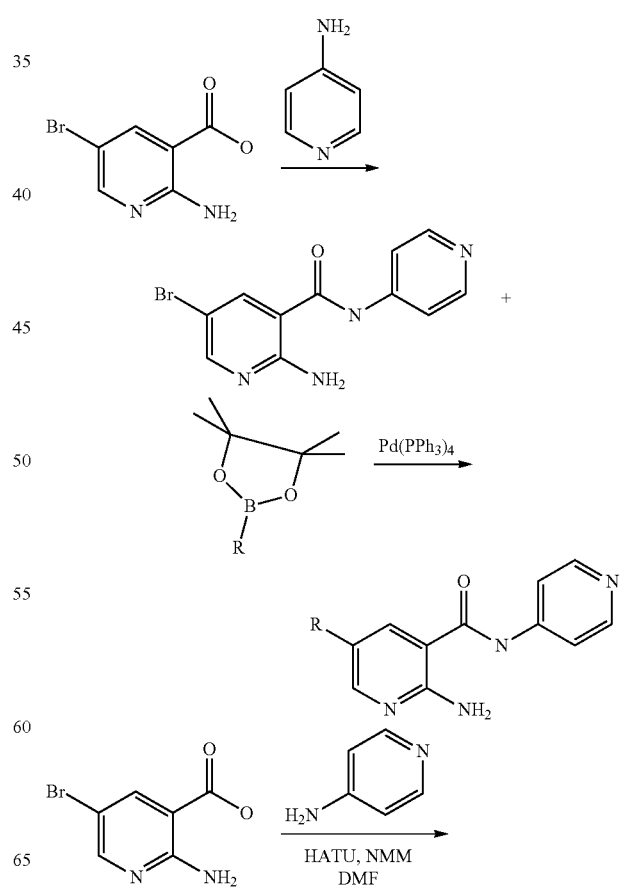

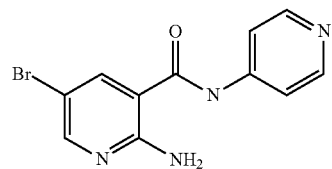

Experimental Procedure:

To a stirred solution of 5-bromo-2-amino-nicotinic acid (500 mg, 2.3 mol, 1 eq) and 4-aminopyridine (260 mg, 2.7 mol, 1.2 eq) in dry DMF (5 ml) is added HATU (1.31 g, 3.4 mol, 1.5 eq) and N-methylmorpholine (690 mg, 6.9 mol, 3 eq) and allowed to stir for 3 h. After the completion of the reaction, the reaction mixture is concentrated; water is added, solid precipitated out and filtered, washed with NaHCO₃ and water to afford the product.

$^1$H NMR (400 MHz, DMSO-$d_6$) δ 10.51 (s, 1H), 8.47-8.46 (d, J=5.4 Hz, 2H), 8.25-8.22 (dd, J=2.4, 7.4 Hz, 2H), 7.69-7.67 (d, J=6.2 Hz, 2H).

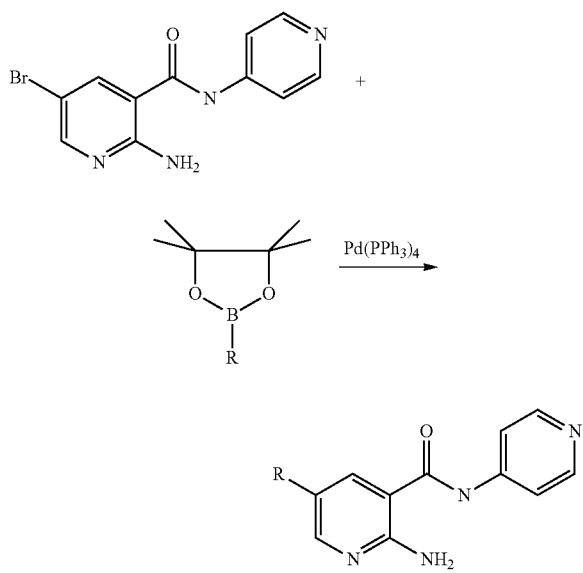

To a stirred solution of 2-amino-5-bromo-N-pyridin-4-yl-nicotinamide (1 eq) in toluene: ethanol (4:1), substituted boronic acid (1.2 eq), 2 M Na₂CO₃ (1.5 eq) is added and degassed for 15 min under N₂ atmosphere. To this reaction mixture Pd(PPh₃)₄ (0.012 eq) is added and heated to 100° C. for 18 hr. After the completion of the reaction the mixture is passed through a Celite bed to remove the inorganic impurities. The filtrate is concentrated under vacuum. Column chromatography affords the pure compound.

EXAMPLE 1

The preparation of 2-Amino-5-(5-piperidin-1-ylmethyl-thiophen-2-yl)-N-pyridin-4-yl-nicotinamide ("A1") is carried out analogously to the following scheme

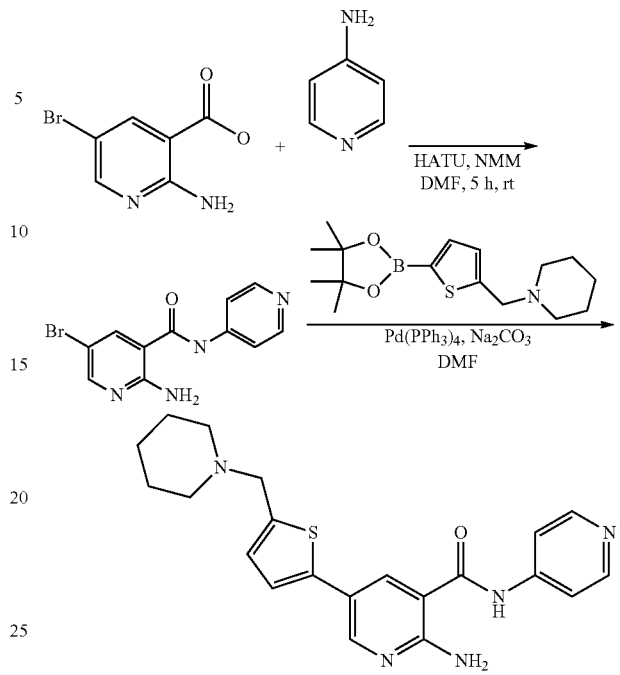

1.1 2-Amino-5-bromo-N-pyridin-4-yl-nicotinamide:

2.0 g of 2-amino-5-bromonicotinic acid and 1.06 g of 4-amino-pyridine are dissolved in 20 mL DMF. 5.26 g HATU ((2-(7-aza-1H-benzotriazole-1-yl)-1,1,3,3-tetramethyl-uronium hexafluorophosphate) and 3.04 mL N-methylmorpholine are added to the solution.

The mixture is stirred for 5 h at room temperature. The DMF is evaporated and the residue is triturated with water. The solid is filtered off and washed with NaHCO₃ solution and water. 2.5 g of a light brown solid is obtained;

HPLC/MS: 1.13 min, [M+H]=293;

$^1$H NMR (400 MHz, DMSO-$d_6$) δ [ppm] 10.51 (s, 1H, NH), 8.48 (d, J=6.0, 2H), 8.25 (dd, J=10.8, 2.3, 2H), 7.69 (d, J=6.3, 2H), 7.18 (s, 2H, NH₂).

1.2 2-Amino-5-(5-piperidin-1-ylmethyl-thiophen-2-yl)-N-pyridin-4-yl-nicotinamide ("A1")

200 mg of 2-amino-5-bromo-N-pyridin-4-yl-nicotinamide and 218 mg 5-(1-piperidinylmethyl)-thiophene-2-boronic acid pinacol ester are dissolved in 8 ml of DMF. 0.84 ml of a 2 molar Na₂CO₃ solution is added under nitrogen. 7.81 mg of tetrakis(triphenylphosphin)-palladium(0) is added. The mixture is stirred for 6 h at 100° C.

The reaction mixture is cooled to room temperature and the DMF is evaporated. Water is added and the resulting precipitate is filtered off, washed with water and dried. The solid is triturated with ethyl acetate and filtered off. 47 mg of the desired product "A1" are obtained as light brown solid;

HPLC/MS: 1.08 min, [M+H]=394;

$^1$H NMR (500 MHz, DMSO-$d_6$) δ [ppm] 10.58 (s, 1H, NH), 8.48 (d, J=6.2, 2H), 8.44 (d, J=2.3, 1H), 8.22 (d, J=2.3, 1H), 7.71 (dd, J=4.8, 1.5, 2H), 7.25 (d, J=3.5, 1H), 7.13 (s, 2H, NH₂), 6.93 (d, J=3.5, 1H), 3.61 (s, 2H), 2.37 (br, 4H), 1.51 (m, 4H), 1.39 (m, 2H).

The following compounds are obtained analogously

2-Amino-N-pyridin-4-yl-5-(5-pyrrolidin-1-ylmethyl-thiophen-2-yl)-nicotinamide ("A2")

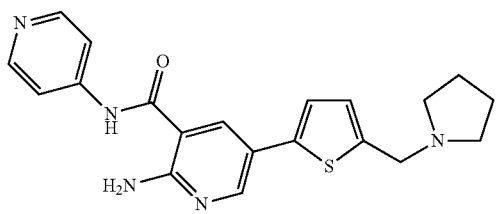 [SMILES: Nc1ncc(-c2ccc(CN3CCCC3)s2)cc1C(=O)Nc1ccncc1]

The reaction of 2-amino-5-bromo-N-pyridin-4-yl-nicotinamide with 5-(1-pyrrolidinyl-methyl)thiophene-2-boronic acid pinacol ester gives compound "A2";
HPLC/MS: 1.16 min, [M+H]=380;
¹H NMR (400 MHz, DMSO-d₆) δ [ppm] 10.51 (s, 1H, NH), 8.51-8.46 (m, 3H), 8.27 (d, J=2.4, 1H), 8.24 (d, J=2.4, 1H), 7.69 (m, 3H), 7.18 (s, 2H), 4.70 (s, 2H), 3.54 (m, 2H), 3.23 (m, 2H), 2.12 (m, 2H), 1.98 (m, 2H);

2-Amino-5-(5-methyl-thiophen-2-yl)-N-pyridin-4-yl-nicotinamide ("A3")

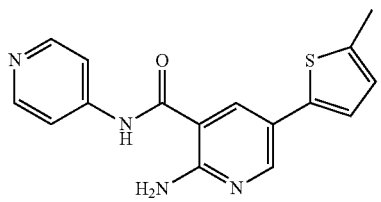 [SMILES: Cc1ccc(-c2cnc(N)c(C(=O)Nc3ccncc3)c2)s1]

The reaction of 2-amino-5-bromo-N-pyridin-4-yl-nicotinamide with 5-methylthiophene-2-boronic acid pinacol ester gives the compound "A3";
HPLC/MS: 1.45 min, [M+H]=311;
¹H NMR (400 MHz, DMSO-d₆) δ [ppm] 10.74 (s, 1H, NH), 8.53 (d, J=4.9, 2H), 8.40 (d, J=2.3, 1H), 8.22 (d, J=2.1, 1H), 7.79 (d, J=11.8, 2H), 7.22 (d, J=3.5, 1H), 7.12 (s, 2H, NH₂), 6.86-6.74 (m, 1H), 2.47 (s, 3H);

2-Amino-5-(3-pyrazol-1-yl-phenyl)-N-pyridin-4-yl-nicotinamide ("A4")

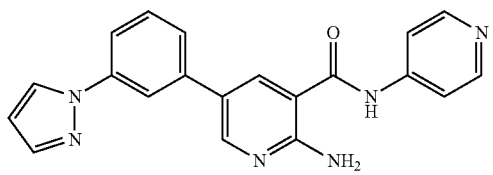 [SMILES: Nc1ncc(-c2cccc(-n3cccn3)c2)cc1C(=O)Nc1ccncc1]

The reaction of 2-amino-5-bromo-N-pyridin-4-yl-nicotinamide with 1-[3-(4,4,5,5-tetramethyl-[1,3,2]dioxaborolan-2-yl)-phenyl]-1H-pyrazole gives the compound "A4";
HPLC/MS: 1.44 min, [M+H]=357;
¹H NMR (400 MHz, DMSO-d₆) δ [ppm] 11.40 (s, 1H, NH), 8.74 (t, J=7.2, 2H), 8.72 (s, 1H), 8.62 (d, J=2.3, 1H), 8.53 (d, J=2.4, 1H), 8.19 (d, J=7.2, 2H), 8.16 (t, J=1.8, 1H), 7.83 (ddd, J=7.9, 2.1, 1.0, 1H), 7.78 (d, J=1.6, 1H), 7.67 (dd, J=6.6, 1.4, 1H), 7.60 (t, J=7.9, 1H), 7.38 (s, 2H), 6.58 (dd, J=2.4, 1.8, 1H);

2-Amino-5-(4-pyrazol-1-yl-phenyl)-N-pyridin-4-yl-nicotinamide ("A5")

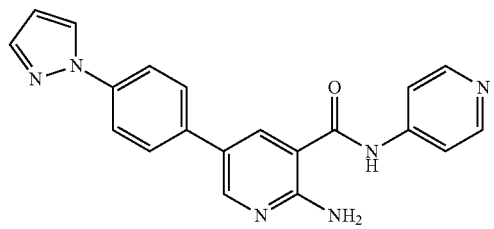 [SMILES: Nc1ncc(-c2ccc(-n3cccn3)cc2)cc1C(=O)Nc1ccncc1]

The reaction of 2-amino-5-bromo-N-pyridin-4-yl-nicotinamide with [4-(1H-pyrazol-1-yl)phenyl]boronic acid gives the compound "A5";
HPLC/MS: 1.38 min, [M+H]=357;
¹H NMR (500 MHz, DMSO-d₆) δ [ppm] 10.60 (s, 1H, NH), 8.59 (d, J=2.4, 1H), 8.54 (d, J=2.4, 1H), 8.52-8.45 (m, 2H), 8.40 (d, J=2.4, 1H), 7.98-7.92 (m, 2H), 7.88-7.84 (m, 2H), 7.78-7.72 (m, 3H), 7.16 (d, J=15.2, 2H), 6.60-6.56 (m, 1H);

2-Amino-5-[1-(2-methoxy-ethyl)-1H-pyrazol-4-yl]-N-pyridin-4-yl-nicotinamide ("A6")

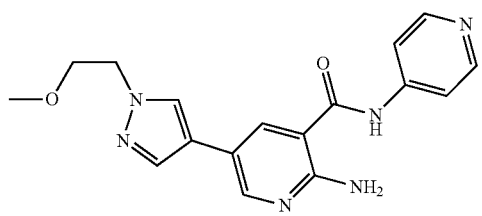 [SMILES: COCCn1cc(-c2cnc(N)c(C(=O)Nc3ccncc3)c2)cn1]

The reaction of 2-amino-5-bromo-N-pyridin-4-yl-nicotinamide with 1-(2-methoxy-ethyl)-4-(4,4,5,5-tetramethyl-[1,3,2]dioxaborolan-2-yl)-1H-pyrazole gives the compound "A6";
HPLC/MS: 1.05 min, [M+H]=339;
¹H NMR (400 MHz, DMSO-d₆) δ [ppm] 11.37 (s, 1H, NH), 8.75 (d, J=7.2, 2H), 8.51 (d, J=2.2, 1H), 8.34 (d, J=2.3, 1H), 8.18 (d, J=7.2, 2H), 8.12 (s, 1H), 7.89 (s, 1H), 4.29 (t, J=5.3, 3H), 3.72 (t, J=5.3, 3H), 3.23 (s, 3H);

2-Amino-N-pyridin-4-yl-5-(4-sulfamoyl-phenyl)-nicotinamide ("A7")

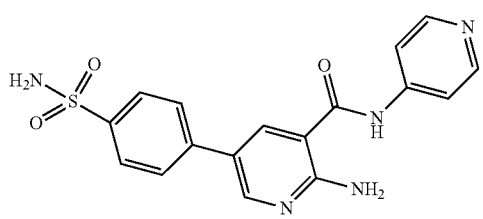 [SMILES: Nc1ncc(-c2ccc(S(N)(=O)=O)cc2)cc1C(=O)Nc1ccncc1]

The reaction of 2-amino-5-bromo-N-pyridin-4-yl-nicotinamide with benzene-sulfonamide-4-boronic acid pinacol ester gives the compound "A7";

HPLC/MS: 1.12 min, [M+H]=370;

$^1$H NMR (400 MHz, DMSO-d$_6$) δ [ppm] 10.57 (s, 1H, NH), 8.61 (d, J=2.3, 1H), 8.55-8.46 (m, 2H), 8.42 (d, J=2.4, 1H), 7.92 (m, 4H), 7.80-7.65 (m, 2H), 7.35 (s, 2H), 7.24 (s, 2H);

2-Amino-N-(2-methyl-pyridin-4-yl)-5-(5-morpholin-4-ylmethyl-thiophen-2-yl)-nicotinamide ("A8")

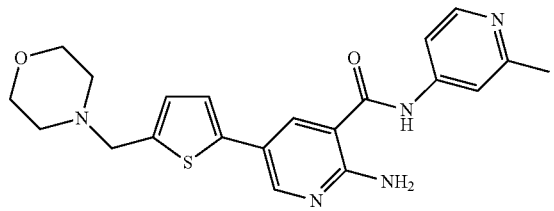 [SMILES: Cc1cc(NC(=O)c2cc(-c3ccc(CN4CCOCC4)s3)cnc2N)ccn1]

The reaction of 2-amino-5-bromo-N-(2-methyl-pyridin-4-yl)-nicotinamide with 5-(4-morpholinylmethyl)thiophene-2-boronic acid pinacol ester gives the compound "A8";

HPLC/MS: 1.02 min, [M+H]=410;

$^1$H NMR (500 MHz, DMSO-d$_6$) δ [ppm] 10.49 (s, 1H, NH), 8.44 (d, J=2.3, 1H), 8.35 (d, J=5.6, 1H), 8.23 (d, J=2.4, 1H), 7.59 (d, J=1.7, 1H), 7.53 (dd, J=5.6, 1.9, 1H), 7.32-7.27 (d, J=3.5, 1H), 7.12 (s, 2H), 6.96 (d, J=3.5, 1H), 3.71 (s, 2H), 3.61-3.53 (m, 4H), 2.45 (s, 3H), 2.43 (m, 4H);

2-Amino-N-(2-ethoxy-pyridin-4-yl)-5-(5-morpholin-4-ylmethyl-thiophen-2-yl)-nicotinamide ("A9")

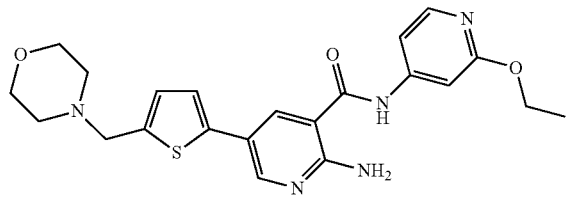 [SMILES: CCOc1cc(NC(=O)c2cc(-c3ccc(CN4CCOCC4)s3)cnc2N)ccn1]

The reaction of 2-amino-5-bromo-N-(2-ethoxy-pyridin-4-yl)-nicotinamide with 5-(4-morpholinylmethyl)thiophene-2-boronic acid pinacol ester gives the compound "A9";

HPLC/MS: 1.37 min, [M+H]=440;

$^1$H NMR (500 MHz, DMSO-d$_6$) δ [ppm] 10.51 (s, 1H, NH), 8.44 (d, J=2.3, 1H), 8.19 (d, J=2.3, 1H), 8.06 (d, J=5.7, 1H), 7.26 (m, 2H), 7.22 (d, J=1.6, 1H), 7.12 (s, 2H), 6.96 (d, J=3.5, 1H), 4.30 (q, J=7.0, 2H), 3.66 (s, 2H), 3.58 (m, 4H), 2.42 (br, 4H), 1.31 (t, J=7.0, 3H);

EXAMPLE 2

3-Amino-6-(5-morpholin-4-ylmethyl-thiophen-2-yl)-pyrazine-2-carboxylic acid pyridin-4-ylamide ("A10")

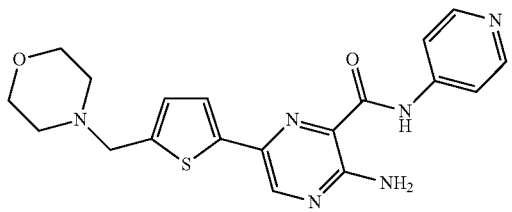 [SMILES: Nc1ncc(-c2ccc(CN3CCOCC3)s2)nc1C(=O)Nc1ccncc1]

2.1 3-Amino-6-bromo-pyrazine-2-carboxylic acid pyridin-4-ylamide

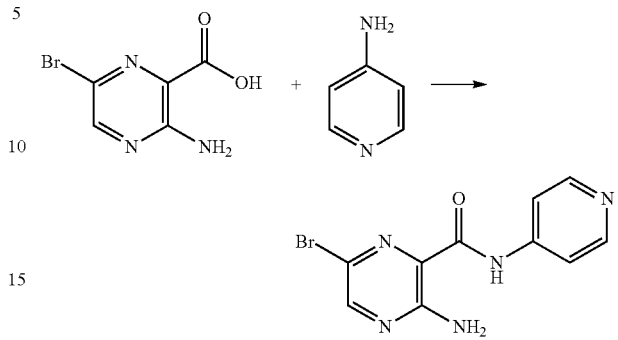

The title compound is obtained from 3-amino-6-bromo-pyrazine-2-carboxylic acid and 4-aminopyridine using the same method as described in step 1 for "A1";

HPLC/MS: 1.18 min, [M+H]=294.

2.2 3-Amino-6-(5-morpholin-4-ylmethyl-thiophen-2-yl)-pyrazine-2-carboxylic acid pyridin-4-ylamide ("A10")

The title compound is prepared analogously to step 2 for "A1"; HPLC/MS: 1.08 min, [M+H]=397.

EXAMPLE 3

6-Amino-6'-piperazin-1-yl-[3,3']bipyridinyl-5-carboxylic acid pyridin-4-ylamide ("A11")

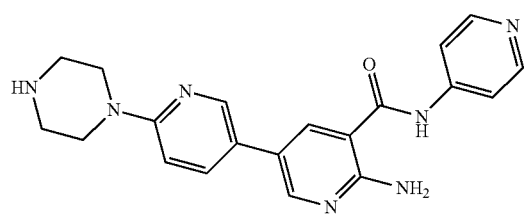 [SMILES: Nc1ncc(-c2ccc(N3CCNCC3)nc2)cc1C(=O)Nc1ccncc1]

3.1 4-[6'-Amino-5'-(pyridin-4-ylcarbamoyl)-[3,3']bipyridinyl-6-yl]-piperazine-1-carboxylic acid tert-butyl ester

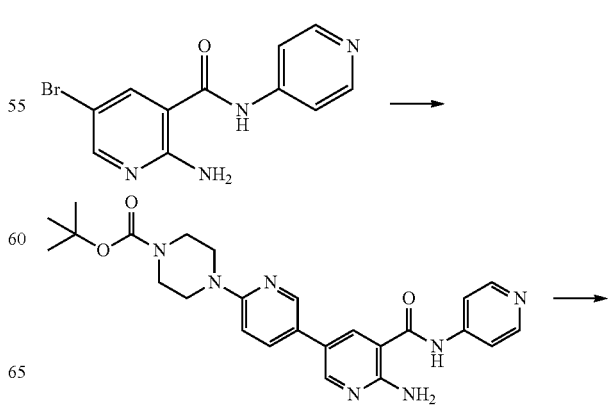

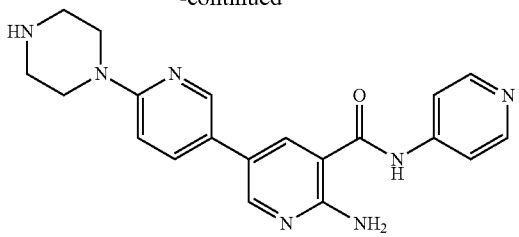

The title compound is obtained from 2-amino-5-bromo-N-(2-ethoxy-pyridin-4-yl)-nicotinamide and 2-(4-tert-butoxy-carbonylpiperazin-1-yl)pyridine-5-boronic acid, pinacol ester analogously to step 2 for "A1"; HPLC/MS: 1.43 min, [M+H]=476.

3.2 1.1 g of 4-[6'-amino-5'-(pyridin-4-ylcarbamoyl)-[3,3'] bipyridinyl-6-yl]-piperazine-1-carboxylic acid tert-butyl ester are dissolved in 25 ml dioxane. 11 ml of HCl in dioxane (4 molar) is added. The mixture is stirred 3 h at room temperature. The mixture is filtered and the solid washed with dioxane. The product is purified by chromatography; HPLC/MS: 1.02 min, [M+H]=376;

$^1$H NMR (400 MHz, DMSO-$d_6$) δ [ppm] 9.08 (d, J=2.2, 1H), 8.84 (d, J=7.3, 2H), 8.77 (d, J=2.1, 1H), 8.67 (d, J=2.3, 1H), 8.48 (dd, J=9.5, 2.4, 1H), 8.38 (d, J=7.3, 2H), 7.54 (d, J=9.5, 1H), 4.09-3.96 (m, 4H), 3.47-3.35 (m, 4H).

EXAMPLE 4

The following compounds are obtained analogously to example 2

3-Amino-6-(1-[1,3]dioxolan-2-ylmethyl-1H-pyrazol-4-yl)-pyrazine-2-carboxylic acid pyridin-4-ylamide ("A12")

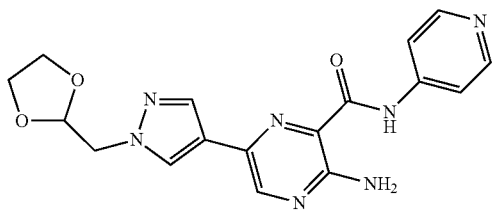 [SMILES: Nc1ncc(-c2cnn(CC3OCCO3)c2)nc1C(=O)Nc1ccncc1]

The reaction of 3-amino-6-bromo-pyrazine-2-carboxylic acid pyridin-4-ylamide (synthesis described for "A10") with 1-[1,3]dioxolan-2-ylmethyl-4-(4,4,5,5-tetramethyl-[1,3,2]dioxaborolan-2-yl)-1H-pyrazole gives the compound "A12"
HPLC/MS: 1.02 min, [M+H]=376;

$^1$H NMR (500 MHz, DMSO-$d_6$) δ [ppm] 10.55 (s, 1H, NH), 8.71 (s, 1H), 8.55-8.41 (m, 3H), 8.27 (s, 1H), 7.91-7.86 (m, 2H), 7.51 (s, 2H), 5.22 (t, J=4.3, 1H), 4.30 (d, J=4.3, 2H), 3.96-3.70 (m, 4H);

3-Amino-6-(5-piperidin-1-ylmethyl-thiophen-2-yl)-pyrazine-2-carboxylic acid pyridin-4-ylamide ("A13")

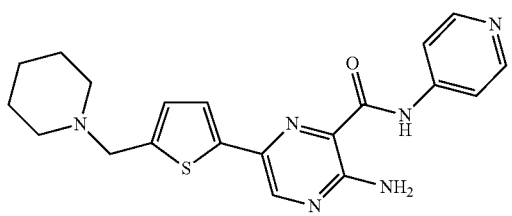

The reaction of 3-amino-6-bromo-pyrazine-2-carboxylic acid pyridin-4-ylamide (synthesis described for "A10") with 1-[5-(4,4,5,5-tetramethyl-[1,3,2]dioxaborolan-2-yl)-thiophen-2-ylmethyl]-piperidine gives the compound "A13";

HPLC/MS: 1.13 min, [M+H]=395;

$^1$H NMR (400 MHz, DMSO-$d_6$) δ [ppm] 10.41 (s, 1H, NH), 8.80 (s, 1H), 8.51 (dd, J=4.8, 1.6, 2H), 7.82 (dd, J=4.8, 1.6, 2H), 7.67 (d, J=3.6, 1H), 7.63 (s, 2H), 6.98 (d, J=3.6, 1H), 3.64 (s, 2H), 2.40 (s, 4H), 1.59-1.32 (m, 6H);

3-Amino-6-(5-pyrrolidin-1-ylmethyl-thiophen-2-yl)-pyrazine-2-carboxylic acid pyridin-4-ylamide ("A14")

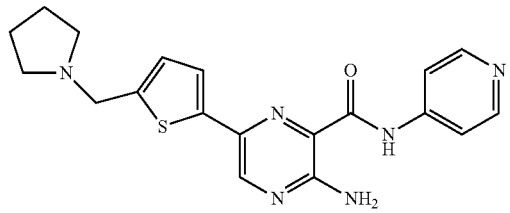 [SMILES: Nc1ncc(-c2ccc(CN3CCCC3)s2)nc1C(=O)Nc1ccncc1]

The reaction of 3-amino-6-bromo-pyrazine-2-carboxylic acid pyridin-4-ylamide (synthesis described for "A10") with 1-[5-(4,4,5,5-tetramethyl-[1,3,2]dioxaborolan-2-yl)-thiophen-2-ylmethyl]-pyrrolidine gives the compound "A14";

HPLC/MS: 1.08 min, [M+H]=381;

$^1$H NMR (500 MHz, DMSO-$d_6$) δ [ppm] 10.40 (s, 1H, NH), 8.83 (s, 1H), 8.51 (dd, J=4.8, 1.5, 2H), 7.88-7.75 (m, 2H), 7.67 (d, J=3.6, 1H), 7.63 (s, 2H), 6.96 (d, J=3.6, 1H), 3.78 (s, 2H), 2.51 (m, 4H), 1.78-1.62 (m, 4H);

2-Amino-N-(2-methyl-pyridin-4-yl)-5-(5-morpholin-4-ylmethyl-thiophen-3-yl)-nicotinamide ("A15")

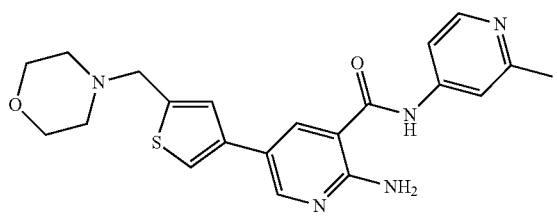 [SMILES: Cc1cc(NC(=O)c2cc(-c3csc(CN4CCOCC4)c3)cnc2N)ccn1]

Reaction of 2-amino-5-bromo-N-(2-methyl-pyridin-4-yl)-nicotinamide with 4-[4-(4,4,5,5-tetramethyl-[1,3,2]dioxaborolan-2-yl)-thiophen-2-ylmethyl]-morpholine gives the compound "A15";

HPLC/MS: 0.99 min, [M+H]=410;

$^1$H NMR (500 MHz, DMSO-$d_6$) δ [ppm] 10.45 (s, 1H, NH), 8.53 (d, J=2.3, 1H), 8.35 (d, J=5.6, 1H), 8.30 (d, J=2.3, 1H), 7.69 (d, J=1.4, 1H), 7.60 (d, J=1.7, 1H), 7.56-7.50 (m, 1H), 7.44 (s, 1H), 7.04 (s, 2H), 3.71 (s, 2H), 3.61-3.58 (m, 4H), 2.45 (m, 7H).

EXAMPLE 5

2-Amino-5-(5-morpholin-4-ylmethyl-thiophen-2-yl)-N-pyridazin-4-yl-nicotinamide ("A16")

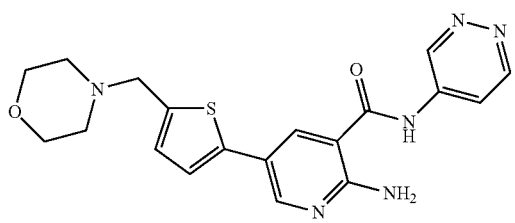 [SMILES: Nc1ncc(-c2ccc(CN3CCOCC3)s2)cc1C(=O)Nc1ccnnc1]

5.1 2-Amino-5-bromo-N-pyridazin-4-yl-nicotinamide

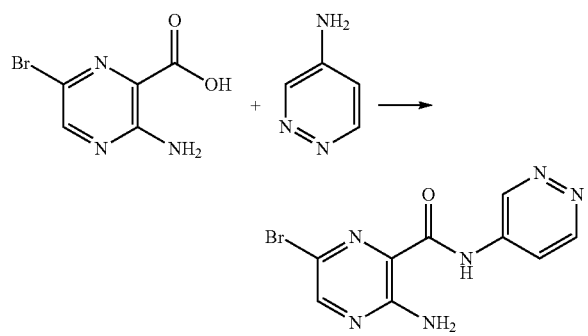

The title compound is obtained from 2-amino-5-bromonicotinic acid and 4-aminopyridazine analogously to "A1" in step 1;

HPLC/MS: 1.40 min, [M+H]=294.

5.2 2-Amino-5-(5-morpholin-4-ylmethyl-thiophen-2-yl)-N-pyridazin-4-yl-nicotinamide is obtained from 2-amino-5-bromo-N-pyridazin-4-yl-nicotinamide and 5-(4-morpholinylmethyl)thiophen-2-boronic acid pinacol ester analogously to "A1" in step 2; HPLC/MS: 1.15 min, [M+H]=397;

$^1$H NMR (500 MHz, DMSO-d$_6$) δ [ppm] 10.78 (s, 1H, NH), 9.47 (d, J=1.9, 1H), 9.08 (d, J=5.9, 1H), 8.48 (d, J=2.3, 1H), 8.27 (d, J=2.3, 1H), 8.03 (dd, J=5.9, 2.7, 1H), 7.27 (d, J=3.1, 1H), 7.20 (s, 2H), 6.98 (s, 1H), 3.68 (s, 2H), 3.59 (s, 4H), 2.48-2.35 (m, 4H).

The following compounds are obtained analogously

2-Amino-5-(1-benzyl-1H-pyrazol-4-yl)-N-(2-methyl-pyridin-4-yl)-nicotinamide ("A17")

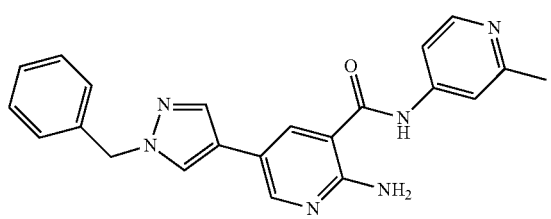 [SMILES: Cc1cc(NC(=O)c2cc(-c3cnn(Cc4ccccc4)c3)cnc2N)ccn1]

Reaction of 2-amino-5-bromo-N-(2-methyl-pyridin-4-yl)-nicotinamide with 4-[4-(4,4,5,5-Tetramethyl-[1,3,2]dioxaborolan-2-yl)-thiophen-2-ylmethyl]-morpholine gives the compound "A17";

HPLC/MS: 1.41 min, [M+H]=385;
$^1$H NMR (500 MHz, DMSO-d$_6$) δ [ppm] 10.45 (s, 1H, NH), 8.53 (d, J=2.3, 1H), 8.35 (d, J=5.6, 1H), 8.30 (d, J=2.3, 1H), 7.69 (d, J=1.4, 1H), 7.60 (d, J=1.7, 1H), 7.55 (dd, J=5.6, 1.9, 1H), 7.44 (s, 1H), 7.04 (s, 2H), 3.71 (s, 2H), 3.63-3.57 (m, 4H), 2.45 (s+m, 7H);

2-Amino-5-(3-pyrazol-1-yl-phenyl)-N-pyridazin-4-yl-nicotinamide ("A18")

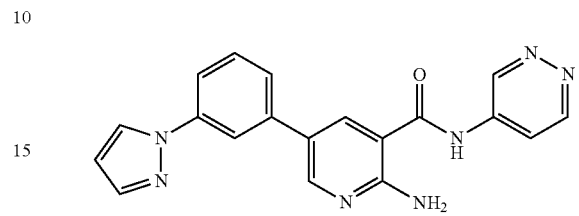

Reaction of 2-amino-5-bromo-N-pyridazin-4-yl-nicotinamide (see step 1 in the synthesis of "A16") and 1-[3-(4,4,5,5-tetramethyl-[1,3,2]dioxaborolan-2-yl)-phenyl]-1H-pyrazole gives the compound "A18";

HPLC/MS: 1.15 min, [M+H]=397;
$^1$H NMR (400 MHz, DMSO-d$_6$) δ [ppm] 11.06 (s, 1H, NH), 9.54 (d, J=2.1, 1H), 9.14 (d, J=5.9, 1H), 8.67 (dd, J=4.1, 2.4, 2H), 8.58 (d, J=2.3, 1H), 8.19 (t, J=1.8, 1H), 8.14 (dd, J=6.0, 2.7, 1H), 7.89-7.80 (m, 1H), 7.77 (d, J=1.7, 1H), 7.68 (d, J=7.9, 1H), 7.59 (t, J=7.9, 1H), 7.37 (s, 2H), 6.60-6.56 (m, 1H);

2-Amino-N-(3-methyl-pyridin-4-yl)-5-(4-pyrazol-1-yl-phenyl)-nicotinamide ("A19")

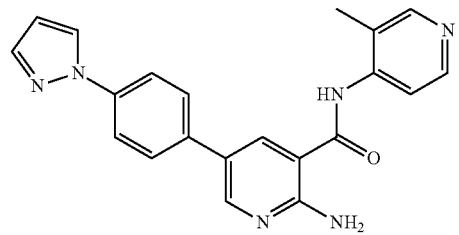 [SMILES: Cc1cnccc1NC(=O)c1cc(-c2ccc(-n3cccn3)cc2)cnc1N]

Reaction of 2-amino-5-bromo-N-(3-methyl-pyridin-4-yl)-nicotinamide with [4-(1H-pyrazol-1-yl)phenyl]boronic acid gives the compound "A19";

HPLC/MS: 1.41 min, [M+H]=371;
$^1$H NMR (500 MHz, DMSO-d$_6$) δ [ppm] 10.07 (s, 1H, NH), 8.59 (d, J=2.3, 1H), 8.55 (d, J=2.4, 1H), 8.45 (s, 1H), 8.44 (d, J=2.3, 1H), 8.40 (d, J=5.3, 1H), 7.96-7.91 (m, 2H), 7.90-7.83 (m, 2H), 7.76 (d, J=1.6, 1H), 7.53 (d, J=5.3, 1H), 7.17 (s, 2H), 6.60-6.54 (m, 1H), 2.28 (s, 3H);

2-Amino-5-[1-(2-methoxy-ethyl)-1H-pyrazol-4-yl]-N-(2-methyl-pyridine-4-yl)-nicotinamide ("A20")

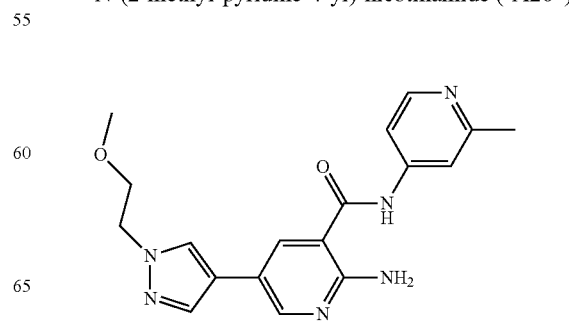

Reaction of 2-amino-5-bromo-N-(2-methyl-pyridin-4-yl)-nicotinamide with 1-(2-methoxy-ethyl)-4-(4,4,5,5-tetramethyl-[1,3,2]dioxaborolan-2-yl)-1H-pyrazole gives the compound "A20";

HPLC/MS: 1.11 min, [M+H]=353;

$^1$H NMR (500 MHz, DMSO-d$_6$) δ [ppm] 10.44 (s, 1H, NH), 8.43 (d, J=2.2, 1H), 8.36 (d, J=5.6, 1H), 8.20 (d, J=2.2, 1H), 8.09 (s, 1H), 7.86 (d, J=0.5, 1H), 7.62 (s, 1H), 7.55 (d, J=5.6, 1H), 6.94 (s, 2H), 4.33-4.22 (m, 2H), 3.76-3.66 (m, 2H), 3.25 (s, 3H), 2.46 (s, 3H);

2-Amino-N-(3-methyl-pyridin-4-yl)-5-(5-morpholin-4-ylmethyl-thiophen-2-yl)-nicotinamide ("A21")

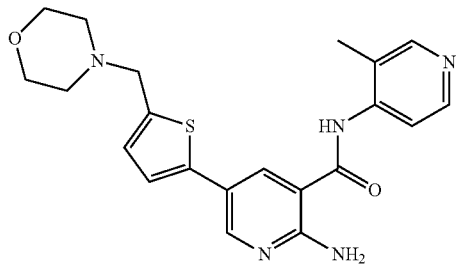 [SMILES: Cc1cnccc1NC(=O)c1cc(-c2ccc(CN3CCOCC3)s2)cnc1N]

Reaction of 2-amino-5-bromo-N-(3-methyl-pyridin-4-yl)-nicotinamide with 5-(4-morpholinylmethyl)thiophene-2-boronic acid pinacol ester gives the compound "A21"; HPLC/MS: 0.97 min, [M+H]=410;

$^1$H NMR (500 MHz, DMSO-d$_6$) δ [ppm] 10.8 (br, 1H, NH), 8.72 (d, J=2.2, 1H), 8.70 (s, 1H), 8.67 (d, J=6.7, 1H), 8.52-8.47 (m, 2H), 7.54 (d, J=3.7, 1H), 7.34 (d, J=3.7, 1H), 4.61 (s, 2H), 4.01-3.87 (m, 2H), 3.67 (m, 2H), 3.33 (m, 2H), 3.14 (m, 2H);

2-Amino-5-[1-(2-methoxy-ethyl)-1H-pyrazol-4-yl]-N-(3-methyl-pyridin-4-yl)-nicotinamide ("A22")

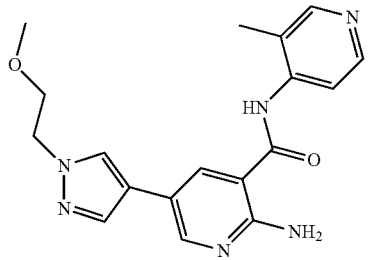 [SMILES: COCCn1cc(-c2cnc(N)c(C(=O)Nc3ccncc3C)c2)cn1]

Reaction of 2-amino-5-bromo-N-(3-methyl-pyridin-4-yl)-nicotinamide with 1-(2-methoxy-ethyl)-4-(4,4,5,5-tetramethyl-[1,3,2]dioxaborolan-2-yl)-1H-pyrazole gives the compound "A22"; HPLC/MS: 1.07 min, [M+H]=353;

2-Amino-5-(4'-methyl-biphenyl-3-yl)-N-pyridin-4-yl-nicotinamide ("A23")

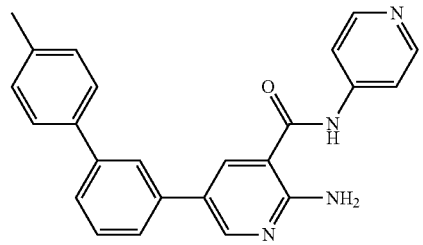 [SMILES: Cc1ccc(-c2cccc(-c3cnc(N)c(C(=O)Nc4ccncc4)c3)c2)cc1]

Reaction of 2-amino-5-bromo-N-pyridin-4-yl-nicotinamide with [3-(p-tolyl)phenyl]-boronic acid gives the compound "A23";

HPLC/MS: 1.90 min, [M+H]=381;
$^1$H NMR (500 MHz, DMSO-d$_6$) δ [ppm] 11.4 (s, 1H, NH), 9.03 (d, J=2.2, 1H), 8.75 (d, J=6.6, 2H), 8.71 (d, J=2.1, 1H), 8.25 (d, J=7.3, 2H), 8.00 (s, 1H), 7.69 (dd, J=10.1, 8.7, 2H), 7.62 (d, J=8.1, 2H), 7.56 (t, J=7.7, 1H), 7.37 (br, 2H, NH2), 7.25 (d, J=8.1, 2H), 2.31 (s, 3H);

2-Amino-5-[1-(2-methoxy-ethyl)-1H-pyrazol-4-yl]-N-pyridazin-4-yl-nicotinamide ("A24")

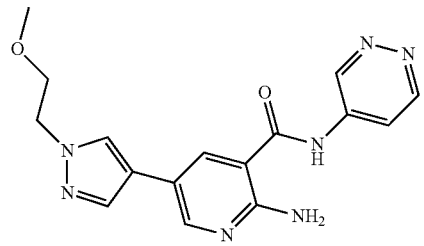 [SMILES: COCCn1cc(-c2cnc(N)c(C(=O)Nc3ccnnc3)c2)cn1]

Reaction of 2-amino-5-bromo-N-pyridazin-4-yl-nicotinamide (see step 1 in the synthesis of "A16") with 1-(2-methoxy-ethyl)-4-(4,4,5,5-tetramethyl-[1,3,2]dioxaborolan-2-yl)-1H-pyrazole gives the compound "A24";

HPLC/MS: 1.21 min, [M+H]=340;

$^1$H NMR (500 MHz, DMSO-d$_6$) δ [ppm] 10.98 (br, 1H, NH), 9.51-9.48 (m, 1H), 9.17 (d, J=6.1, 1H), 8.48 (d, J=2.2, 1H), 8.42 (d, J=1.6, 1H), 8.14 (m, 2H), 7.91 (s, 1H), 7.36 (br, 2H), 4.29 (t, J=5.3, 2H), 3.72 (t, J=5.3, 3H), 3.25 (s, 3H);

2-Amino-5-(1-carbamoylmethyl-1H-pyrazol-4-yl)-N-pyridin-4-yl-nicotinamide ("A25")

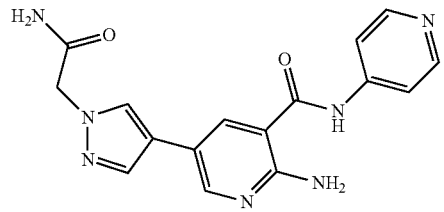 [SMILES: NC(=O)Cn1cc(-c2cnc(N)c(C(=O)Nc3ccncc3)c2)cn1]

Reaction of 2-amino-5-bromo-N-pyridin-4-yl-nicotinamide with 2-[4-(4,4,5,5-tetramethyl-[1,3,2]dioxaborolan-2-yl)-pyrazol-1-yl]-acetamide gives the compound "A25"; HPLC/MS: 0.94 min, [M+H]=338;

¹H NMR (400 MHz, DMSO-d₆) δ [ppm] 10.51 (s, 1H, NH), 8.48 (dd, J=4.8, 1.5, 2H), 8.44 (d, J=2.3, 1H), 8.22 (d, J=2.3, 1H), 8.08 (d, J=0.5, 1H), 7.88 (d, J=0.6, 1H), 7.72 (dd, J=4.8, 1.6, 2H), 7.49 (s, 1H), 7.24 (s, 1H), 6.94 (s, 2H), 4.78 (s, 2H);

2-Amino-N-(2,6-dimethyl-pyridin-4-yl)-5-(5-morpholin-4-ylmethyl-thiophen-2-yl)-nicotinamide ("A26")

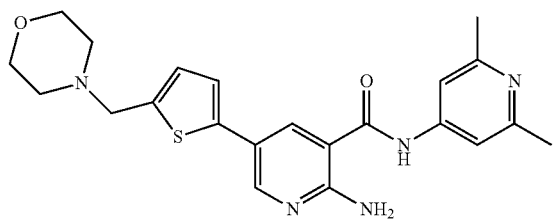 [SMILES: Cc1cc(NC(=O)c2cc(-c3ccc(CN4CCOCC4)s3)cnc2N)cc(C)n1]

Reaction of 2-amino-5-bromo-N-(2,6-dimethyl-pyridin-4-yl)-nicotinamide with 5-(4-morpholinylmethyl)thiophene-2-boronic acid pinacol ester gives the compound "A26"; HPLC/MS: 1.09 min, [M+H]=424;

¹H NMR (400 MHz, DMSO-d₆) δ [ppm] 10.43 (s, 1H, NH), 8.43 (d, J=2.3, 1H), 8.21 (d, J=2.3, 1H), 7.43 (s, 2H), 7.26 (d, J=3.5, 1H), 7.14 (s, 2H), 6.96 (d, J=3.5, 1H), 3.68 (s, 2H), 3.64-3.54 (m, 4H), 2.53-2.47 (m, 4H), 2.43 (s, 6H).

EXAMPLE 6

2-Amino-5-(5-morpholin-4-ylmethyl-thiophen-2-yl)-N-pyrimidin-4-yl-nicotinamide ("A27")

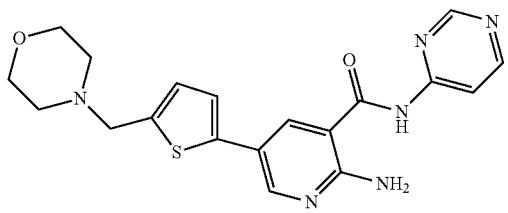 [SMILES: Nc1ncc(-c2ccc(CN3CCOCC3)s2)cc1C(=O)Nc1ccncn1]

6.1 Reaction of 2-amino-5-bromo-pyridine-3-carboxylic acid with pyrimidin-4-amine according to the synthesis described for "A1" step 1, gives 2-amino-5-bromo-N-pyrimidin-4-yl-pyridine-3-carboxamide.

6.2 "A27" is prepared from 2-amino-5-bromo-N-pyrimidin-4-yl-pyridine-3-carboxamide and 5-(4-morpholinylmethyl)thiophene-2-boronic acid pinacol ester according to step 2 of the synthesis of "A1";

HPLC/MS: 1.27 min, [M+H]=397;

¹H NMR (400 MHz, DMSO-d₆) δ [ppm] 11.34 (s, 1H, NH), 8.97 (d, J=0.9, 1H), 8.72 (d, J=5.8, 1H), 8.46 (d, J=2.3, 1H), 8.40 (d, J=2.3, 1H), 8.14 (dd, J=5.8, 1.2, 1H), 7.33 (d, J=3.5, 1H), 7.25 (s, 2H), 6.97 (d, J=3.4, 1H), 3.69 (s, 2H), 3.65-3.56 (m, 4H), 2.45 (s, 4H).

EXAMPLE 7

2-Amino-N-furo[3,2-b]pyridin-7-yl-5-[1-(2-methoxy-ethyl)-1H-pyrazol-4-yl]-nicotinamide ("A28")

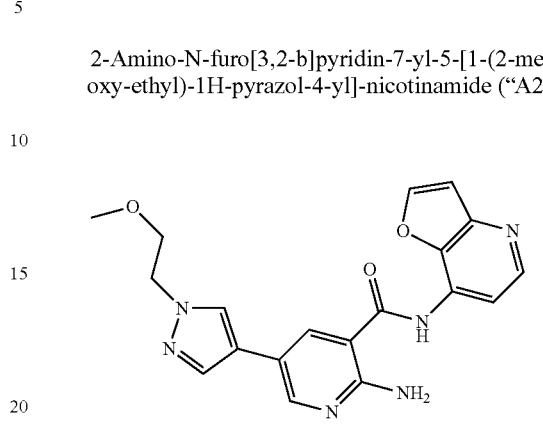

7.1 Reaction of 2-amino-5-bromo-pyridine-3-carboxylic acid with furo[3,2-b]pyridin-7-amine according to the synthesis described for "A1" step 1, gives 2-Amino-5-bromo-N-furo[3,2-b]pyridin-7-yl-pyridine-3-carboxamide.

7.2 "A28" is obtained from 2-amino-5-bromo-N-furo[3,2-b]pyridin-7-yl-pyridine-3-carboxamide and 1-(2-methoxy-ethyl)-4-(4,4,5,5-tetramethyl-[1,3,2]dioxaborolan-2-yl)-1H-pyrazole according to the procedure described for "A1" step 2;

HPLC/MS: 1.22 min, [M+H]=379;

¹H NMR (500 MHz, DMSO-d₆) δ [ppm] 10.70 (s, 1H, NH), 8.48-8.44 (m, 2H), 8.34 (d, J=2.0, 1H), 8.32 (d, J=2.2, 1H), 8.10 (s, 1H), 7.88 (s, 1H), 7.60 (d, J=5.3, 1H), 7.15 (d, J=2.2, 1H), 7.02 (s, 2H), 4.28 (t, J=5.3, 2H), 3.71 (t, J=5.3, 2H), 3.25 (s, 3H).

The following compounds are obtained analogously

2-Amino-N-furo[3,2-b]pyridin-7-yl-5-(5-morpholin-4-ylmethyl-thiophen-2-yl)-nicotinamide ("A29")

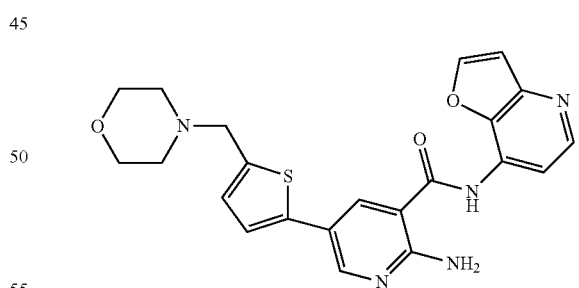

Reaction of 2-amino-5-bromo-N-furo[3,2-b]pyridin-7-yl-pyridine-3-carboxamide (synthesis described above) with 5-(4-morpholinylmethyl)thiophene-2-boronic acid pinacol ester gives the compound "A29";

HPLC/MS: 1.17 min, [M+H]=436;

¹H NMR (500 MHz, DMSO-d₆) δ [ppm] 10.85 (s, 1H, NH), 8.48 (t, J=3.5, 2H), 8.36 (d, J=2.3, 1H), 8.33 (d, J=2.2, 1H), 7.62 (d, J=5.3, 1H), 7.30 (d, J=3.5, 1H), 7.23 (s, 2H), 7.16 (d, J=2.2, 1H), 6.98 (d, J=3.5, 1H), 3.68 (s, 2H), 3.62-3.56 (m, 4H), 2.44 (m, 4H);

4-[6-Amino-5-(pyridin-4-ylcarbamoyl)-pyridin-3-yl]-benzoic acid methyl ester ("A30")

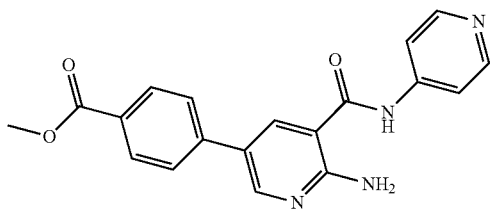 [SMILES: COC(=O)c1ccc(-c2cnc(N)c(C(=O)Nc3ccncc3)c2)cc1]

Reaction of 2-amino-5-bromo-N-pyridin-4-yl-nicotinamide with 4-methoxycarbonyl)-benzoic acid gives the compound "A30"; HPLC/MS: 1.48 min, [M+H]=349;

4-[6-Amino-5-(pyridin-4-ylcarbamoyl)-pyridin-3-yl]-benzoic acid ("A31")

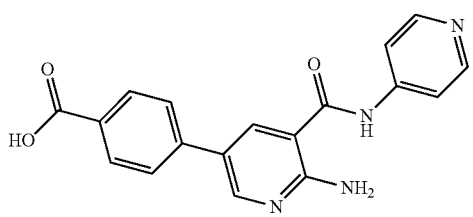 [SMILES: Nc1ncc(-c2ccc(C(=O)O)cc2)cc1C(=O)Nc1ccncc1]

190 mg of 4-[6-amino-5-(pyridin-4-ylcarbamoyl)-pyridin-3-yl]-benzoic acid methyl ester are dissolved in 20 ml of MeOH. 175 mg $Na_2CO_3$ in 6 ml of water are added.

The reaction mixture is stirred over night at 50° C.

The desired material "A31" is purified by chromatography; HPLC/MS: 1.28 min, [M+H]=335;

$^1$H NMR (400 MHz, DMSO-$d_6$) δ [ppm] 13.24-12.61 (m, 1H, OH), 11.36 (s, 1H, NH), 8.74 (d, J=6.7, 2H), 8.69 (d, J=2.4, 1H), 8.51 (d, J=2.4, 1H), 8.18 (d, J=7.2, 2H), 8.06-7.98 (m, 2H), 7.90-7.81 (m, 2H), 7.40 (s, 2H);

3-{4-[6-Amino-5-(pyridin-4-ylcarbamoyl)-pyridin-3-yl]-phenyl}-propionic acid ("A32")

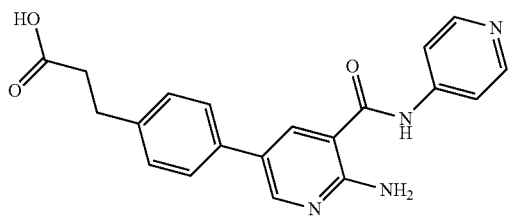 [SMILES: Nc1ncc(-c2ccc(CCC(=O)O)cc2)cc1C(=O)Nc1ccncc1]

Reaction of 2-amino-5-bromo-N-pyridin-4-yl-nicotinamide with 3-(4-boronophenyl)-propanoic acid gives the compound "A32"; HPLC/MS: 1.28 min, [M+H]=363;

$^1$H NMR (500 MHz, DMSO-$d_6$) δ [ppm] 12.09 (s, 1H, OH), 10.52 (s, 1H, NH), 8.48 (dd, J=6.7, 4.2, 3H), 8.31 (d, J=2.2, 1H), 7.72 (d, J=6.1, 2H), 7.62 (d, J=8.1, 2H), 7.32 (d, J=8.1, 2H), 7.09 (s, 2H), 2.86 (t, J=7.5, 2H), 2.56 (t, J=7.5, 2H);

2-Amino-N-(3-chloro-pyridin-4-yl)-5-(5-morpholin-4-ylmethyl-thiophen-2-yl)-nicotinamide ("A33")

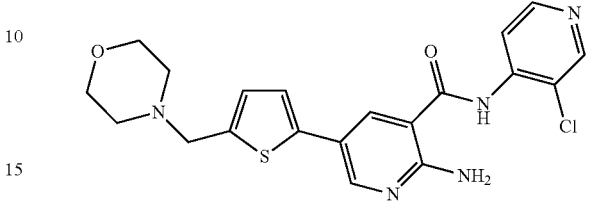

Reaction of 2-amino-5-bromo-N-(3-chloro-4-pyridyl)pyridine-3-carboxamide with 5-(4-morpholinylmethyl)thiophene-2-boronic acid pinacol ester gives the compound "A33"; HPLC/MS: 1.25 min, [M+H]=343;

$^1$H NMR (500 MHz, DMSO-$d_6$) δ [ppm] 10.30 (s, 1H, NH), 8.70 (s, 1H), 8.53 (d, J=5.3, 1H), 8.49 (d, J=2.3, 1H), 8.30 (d, J=2.4, 1H), 7.79 (d, J=5.3, 1H), 7.28 (d, J=3.5, 1H), 7.21 (s, 2H), 6.97 (d, J=3.5, 1H), 3.68 (s, 2H), 3.62-3.55 (m, 4H), 2.44 (s, 4H),

2-Amino-5-(1H-pyrazol-4-yl)-N-pyridin-4-yl-nicotinamide ("A34")

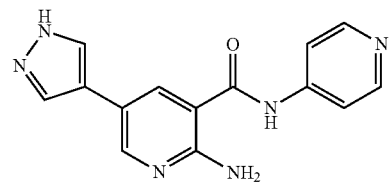 [SMILES: Nc1ncc(-c2cn[nH]c2)cc1C(=O)Nc1ccncc1]

Reaction of 2-amino-5-bromo-N-pyridin-4-yl-nicotinamide with 4-(4,4,5,5-tetramethyl-1,3,2-dioxaborolan-2-yl)-1H-pyrazole gives the compound "A34";

HPLC/MS: 0.89 min, [M+H]=281;

$^1$H NMR (500 MHz, DMSO-$d_6$) δ [ppm] 12.89 (s, 1H, NH), 10.48 (s, 1H, NH), 8.47 (dd, J=10.1, 4.2, 3H), 8.23 (d, J=2.2, 1H), 8.11 (s, 1H), 7.91 (s, 1H), 7.71 (dd, J=10.9, 9.6, 2H), 6.91 (s, 2H);

4-{[2-Amino-5-(5-morpholin-4-ylmethyl-thiophen-2-yl)-pyridine-3-carbonyl]-amino}-nicotinic acid methyl ester ("A35")

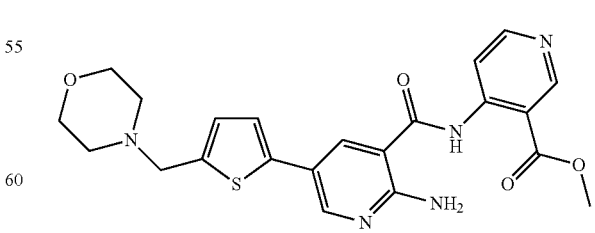

Reaction of methyl 4-[(2-amino-5-bromo-pyridine-3-carbonyl)amino]pyridine-3-carboxylate with 5-(4-morpholinylmethyl)thiophene-2-boronic acid pinacol ester gives compound "A35"; HPLC/MS: 1.36 min, [M+H]=454;

$^1$H NMR (500 MHz, DMSO-d$_6$) δ [ppm] (s, 1H, NH), 9.04 (s, 1H), 8.70 (d, J=5.8, 1H), 8.52 (d, J=2.3, 1H), 8.34 (d, J=5.8, 1H), 8.20 (d, J=2.3, 1H), 7.31 (s, 2H), 7.26 (d, J=3.5, 1H), 6.98 (d, J=3.5, 1H), 3.92 (s, 3H), 3.69 (s, 2H), 3.62-3.53 (m, 4H), 2.44 (s, 4H);

N-(2-Acetylamino-pyridin-4-yl)-2-amino-5-(5-morpholin-4-ylmethyl-thiophen-2-yl)-nicotinamide ("A36")

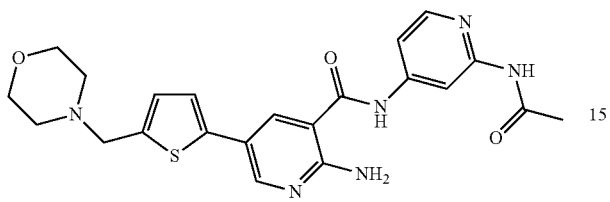

Reaction of N-(2-acetamido-4-pyridyl)-2-amino-5-bromo-pyridine-3-carboxamide with 5-(4-morpholinylmethyl)thiophene-2-boronic acid pinacol ester gives the compound "A36"; HPLC/MS: 1.14 min, [M+H]=453;
$^1$H NMR (500 MHz, DMSO-d$_6$) δ [ppm] 10.63 (s, 1H, NH), 10.37 (s, 1H, NH), 8.43 (d, J=2.3, 1H), 8.38 (d, J=1.2, 1H), 8.23 (d, J=2.3, 1H), 8.20 (d, J=5.6, 1H), 7.60 (dd, J=5.6, 1.9, 1H), 7.26 (d, J=3.5, 1H), 7.13 (s, 2H), 6.96 (d, J=3.5, 1H), 3.67 (s, 2H), 3.61-3.57 (m, 4H), 2.43 (s, 4H), 2.09 (s, 3H);

3-[6-Amino-5-(pyridin-4-ylcarbamoyl)-pyridin-2-yl]-benzoic acid ("A37")

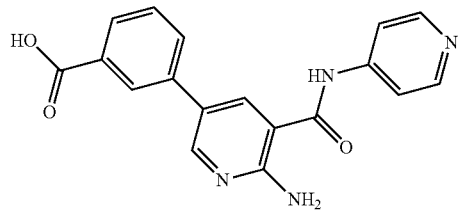 [SMILES: Nc1ncc(-c2cccc(C(=O)O)c2)cc1C(=O)Nc1ccncc1]

1. (3-Methoxycarbonylphenyl)boronic acid and 2-amino-5-bromo-N-pyridin-4-yl-nicotinamide are reacted analogously to "A1" step 2 to give methyl 3-[6-amino-5-(4-pyridylcarbamoyl)-3-pyridyl]benzoate.
2. "A37" is obtained from methyl 3-[6-amino-5-(4-pyridylcarbamoyl)-3-pyridyl]benzoate using the method described for "A31";
HPLC/MS: 1.19 min, [M+H]=335;
$^1$H NMR (400 MHz, DMSO-d$_6$) δ [ppm] 13.07 (br, 1H, OH), 11.41 (s, 1H, NH), 8.74 (d, J=7.2, 2H), 8.64 (d, J=2.4, 1H), 8.48 (d, J=2.4, 1H), 8.26 (t, J=1.6, 1H), 8.19 (d, J=7.2, 2H), 8.01-7.88 (m, 2H), 7.62 (t, J=7.8, 1H), 7.38 (s, 2H);

2-Amino-N-(3-chloro-pyridin-4-yl)-5-[1-(2-methoxy-ethyl-)-1H-pyrazol-4-yl]nicotinamide ("A38")

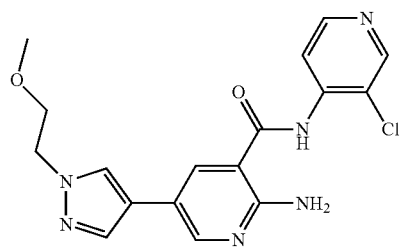 [SMILES: COCCn1cc(-c2cnc(N)c(C(=O)Nc3ccncc3Cl)c2)cn1]

Reaction of 2-amino-5-bromo-N-(3-chloro-4-pyridyl)pyridine-3-carboxamide with 1-(2-methoxy-ethyl)-4-(4,4,5,5-tetramethyl-[1,3,2]dioxaborolan-2-yl)-1H-pyrazole gives the compound "A38"; HPLC/MS: 1.39 min, [M+H]=373;
$^1$H NMR (500 MHz, DMSO-d$_6$) δ [ppm] 10.16 (s, 1H, NH), 8.69 (s, 1H), 8.51 (d, J=5.3, 1H), 8.46 (d, J=2.2, 1H), 8.28 (d, J=2.3, 1H), 8.09 (s, 1H), 7.86 (s, 1H), 7.79 (d, J=5.3, 1H), 7.00 (s, 2H), 4.28 (t, J=5.3, 2H), 3.71 (t, J=5.3, 2H), 3.24 (s, 4H);

2-Amino-N-(4-methoxy-phenyl)-5-(5-morpholin-4-ylmethyl-thiophen-2-yl)-nicotinamide ("A39")

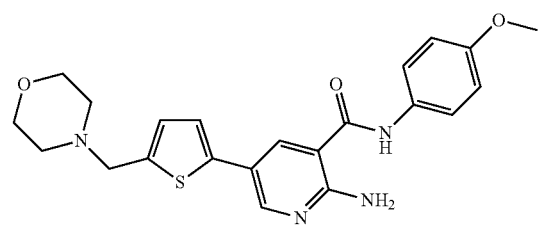 [SMILES: COc1ccc(NC(=O)c2cc(-c3ccc(CN4CCOCC4)s3)cnc2N)cc1]

Reaction of 2-amino-5-bromo-N-(4-methoxyphenyl)pyridine-3-carboxamide with 5-(4-morpholinylmethyl)thiophene-2-boronic acid pinacol ester gives the compound "A39"; HPLC/MS: 1.46 min, [M+H]=425;

2-Amino-N-(6-methoxy-pyridin-3-yl)-5-(5-morpholin-4-ylmethyl-thiophen-2-yl)-nicotinamide ("A40")

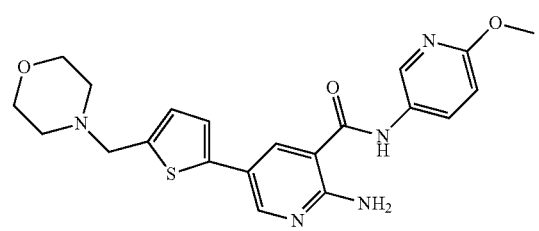 [SMILES: COc1ccc(NC(=O)c2cc(-c3ccc(CN4CCOCC4)s3)cnc2N)cn1]

Reaction of 2-amino-5-bromo-N-(6-methoxy-3-pyridyl)pyridine-3-carboxamide with 5-(4-morpholinylmethyl)thiophene-2-boronic acid pinacol ester gives the compound "A40"; HPLC/MS: 1.29 min, [M+H]=426;

EXAMPLE 8

2-Amino-N-(3-methylcarbamoyl-pyridin-4-yl)-5-(5-morpholin-4-ylmethyl-thiophen-2-yl)-nicotinamide ("A41")

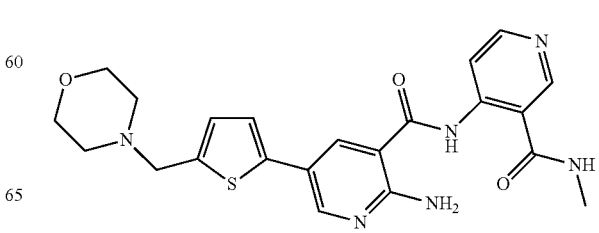

100 mg of methyl 4-[[2-amino-5-[5-(morpholinomethyl)-2-thienyl]pyridine-3-carbonyl]amino]pyridine-3-carboxylate (MSC 2392368) are dissolved in 4 ml THF and 4 ml of methylamine (40% in water) are added. The mixture is stirred for 2 h at room temperature. The mixture is evaporated and treated with petrol ether and ethyl acetate. After filtration 79 mg of a yellow solid is obtained;

HPLC/MS: 1.17 min, [M+H]=453;

$^1$H NMR (500 MHz, DMSO-d$_6$) δ [ppm] 12.76 (s, 1H), 9.05 (d, J=4.3, 1H), 8.94 (s, 1H), 8.61 (d, J=5.7, 1H), 8.51 (d, J=2.3, 1H), 8.45 (d, J=5.7, 1H), 8.16 (d, J=2.3, 1H), 7.35 (s, 2H), 7.25 (d, J=3.5, 1H), 6.98 (d, J=3.5, 1H), 3.68 (s, 2H), 3.60-3.57 (m, 4H), 2.86 (d, J=4.5, 3H), 2.44 (m, 4H).

EXAMPLE 9

2-Amino-5-[1-(2-hydroxy-ethyl)-1H-pyrazol-4-yl]-N-pyridin-4-yl-nicotinamide ("A42")

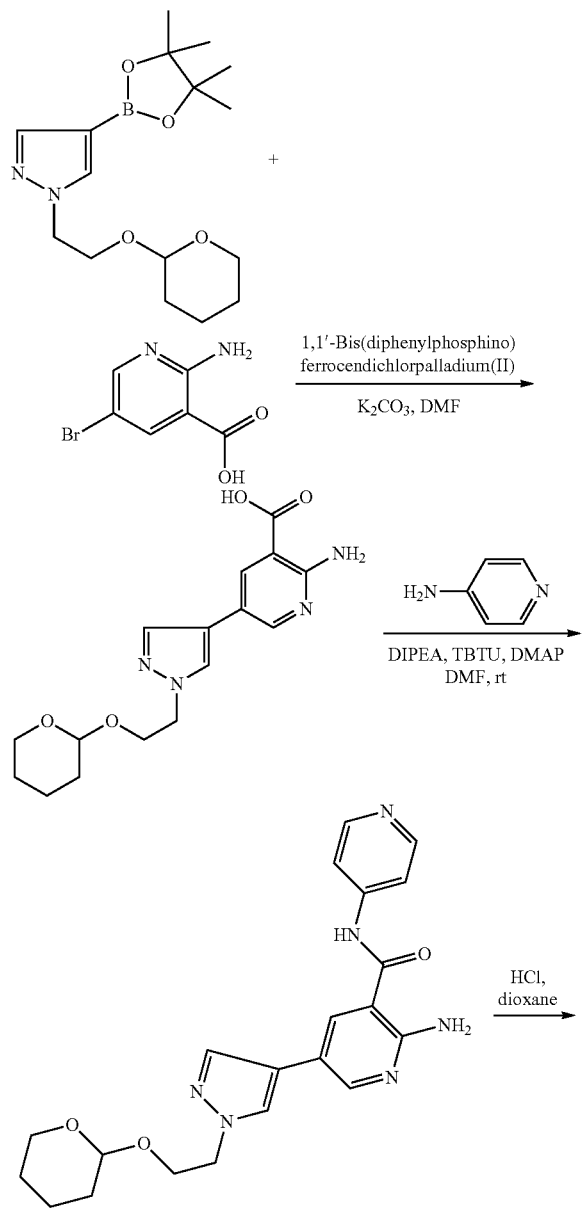

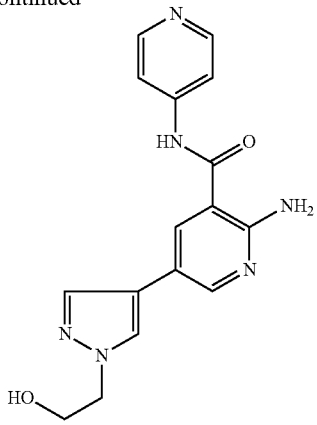

9.1 2-Amino-5-{1-[2-(tetrahydro-pyran-2-yloxy)-ethyl]-1H-pyrazol-4-yl}-nicotinic acid 1.5 g 1-[2-(tetrahydropyran-2-yloxy)-ethyl]-4-(4,4,5,5-tetramethyl-[1,3,2]dioxa-borolan-2-yl)-1H-pyrazol and 808 mg 2-amino-5-bromonicotinic acid are dissolved in 10 ml of DMF. 3.3 g of potassium carbonate are added to the solution. The mixture is heated to 80° C. 395 mg of 1,1'-bis(diphenylphosphino)ferrocenedichloropalladium(II), dichloromethane adduct are added and the mixture is heated for 2 h.

The solution is evaporated and the crude product is purified by silica gel chromatography using ethyl acetate/MeOH 9:1; 496 mg of 2-Amino-5-{1-[2-(tetrahydro-pyran-2-yloxy)-ethyl]-1H-pyrazol-4-yl}-nicotinic acid as a brown oil;

HPLC/MS: 1.27 min, [M+H]=333.

9.2 2-Amino-N-pyridin-4-yl-5-{1-[2-(tetrahydro-pyran-2-yloxy)-ethyl]-1H-pyrazol-4-yl}-nicotinamide:

303 mg of 2-Amino-5-{1-[2-(tetrahydro-pyran-2-yloxy)-ethyl]-1H-pyrazol-4-yl}-nicotinic acid, 84 mg of 4-aminopyridine and 284 mg of O-(1H-benzotriazol-1-yl)-N,N,N',N'-tetramethyluroniumtetrafluorborate (TBTU) are dissolved in 10 ml of DMF. 0.15 ml of N-ethyldiisopropylamine and 21 mg of 4-(dimethylamino)-pyridine are added. The mixture is stirred over night at room temperature.

The reaction mixture is evaporated and purified by silica gel chromatography using dichloromethane/MeOH 9:1.

160 mg of 2-Amino-N-pyridin-4-yl-5-{1-[2-(tetrahydro-pyran-2-yloxy)-ethyl]-1H-pyrazol-4-yl}-nicotinamide are obtained as a yellow solid; HPLC/MS: 1.27 min, [M+H]=409.

9.3 2-Amino-5-[1-(2-hydroxy-ethyl)-1H-pyrazol-4-yl]-N-pyridin-4-yl-nicotinamide:

160 mg of 2-Amino-N-pyridin-4-yl-5-{1-[2-(tetrahydro-pyran-2-yloxy)-ethyl]-1H-pyrazol-4-yl}-nicotinamide are dissolved in 4 ml of dichloromethane. 0.4 ml of HCl in dioxane (ca. 4 mol/l) are added. After 1 h, the precipitate is filtered off and washed with dichloromethane.

99 mg of 2-Amino-5-[1-(2-hydroxy-ethyl)-1H-pyrazol-4-yl]-N-pyridin-4-yl-nicotinamide are obtained as yellow solid; HPLC/MS: 0.98 min, [M+H]=325;

$^1$H NMR (400 MHz, DMSO-d$_6$) δ [ppm] 10.56 (s, 1H, NH), 8.50 (d, J=6.2, 2H), 8.43 (d, J=2.2, 1H), 8.21 (d, J=2.3, 1H), 8.09 (s, 1H), 7.86 (s, 1H), 7.76 (d, J=6.3, 2H), 6.94 (s, 2H), 4.90 (s, 1H, OH), 4.16 (t, J=5.6, 2H), 3.76 (d, J=4.8, 2H).

EXAMPLE 10

The following compounds are obtained analogously to example 1;

HPLC Method: A—0.1% TFA in H$_2$O, B—0.1% TFA in ACN: Flow—2.0 ml/min.

Column: X Bridge C8 (50×4.6 mm.3.5 μ).

2-Amino-5-(5-morpholin-4-ylmethyl-thiophen-3-yl)-N-pyridin-4-yl-nicotinamide ("A43")

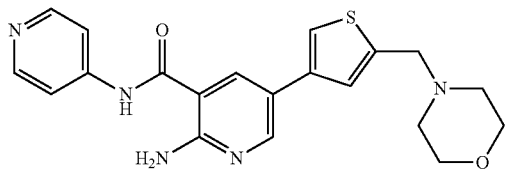 [SMILES: Nc1ncc(-c2csc(CN3CCOCC3)c2)cc1C(=O)Nc1ccncc1]

¹H NMR (400 MHz, DMSO-d₆) δ [ppm] 10.53 (s, 1H), 8.53 (d, J=2.08 Hz, 1H), 8.48 (d, J=5.00 Hz, 2H), 8.30 (d, J=2.12 Hz, 1H), 7.69-7.71 (m, 3H), 7.44 (s, 1H), 7.07-7.12 (m, 2H), 3.69 (s, 2H), 3.57-3.59 (m, 4H), 2.49-2.49 (m, 4H);

LCMS: Mass found (M+1, 396);

HPLC>97%, Rt (min): 1.362.

5-(4-Acetyl-1H-pyrrol-2-yl)-2-amino-N-pyridin-4-yl-nicotinamide ("A44")

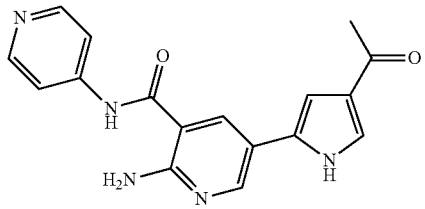 [SMILES: CC(=O)c1c[nH]c(-c2cnc(N)c(C(=O)Nc3ccncc3)c2)c1]

¹H NMR (400 MHz, DMSO-d₆) δ [ppm] 11.96 (s, 1H), 10.61 (s, 1H), 8.48-8.53 (m, 1H), 8.47 (d, J=1.40 Hz, 2H), 8.40 (d, J=2.04 Hz, 1H), 7.74 (dd, J=1.48, 4.90 Hz, 2H), 7.68 (dd, J=1.64, 2.88 Hz, 1H), 7.07 (s, 2H), 6.85 (t, J=2.24 Hz, 1H), 2.34 (s, 3H);

LCMS: Mass found (M+1, 322);

HPLC>93%, RTL (min): 1.62.

2-Amino-5-furan-3-yl-N-pyridin-4-yl-nicotinamide ("A45")

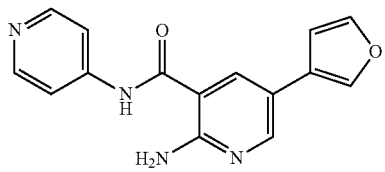 [SMILES: Nc1ncc(-c2ccoc2)cc1C(=O)Nc1ccncc1]

¹H NMR (400 MHz, DMSO-d₆) δ [ppm] 10.54 (s, 1H), 8.44-8.44 (m, 3H), 8.23 (d, J=2.32 Hz, 1H), 8.12 (d, J=2.36 Hz, 1H), 7.74 (t, J=3.36 Hz, 1H), 7.68 (d, J=4.64 Hz, 2H), 6.97-7.02 (m, 2H);

LCMS: Mass found (M+1, 281);

HPLC>96%, Rt (min): 1.64.

2-Amino-5-(1-benzyl-1H-pyrazol-4-yl)-N-pyridin-4-yl-nicotinamide ("A46")

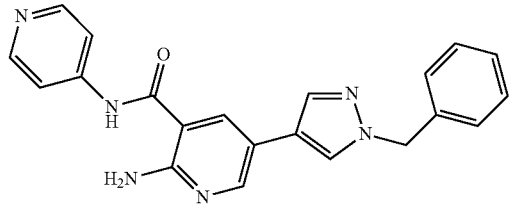 [SMILES: Nc1ncc(-c2cnn(Cc3ccccc3)c2)cc1C(=O)Nc1ccncc1]

¹H NMR (400 MHz, DMSO-d₆) δ [ppm] 10.49 (s, 1H), 8.43-8.48 (m, 3H), 8.20 (dd, J=2.28, 6.54 Hz, 2H), 7.90-7.91 (m, 2H), 7.69 (dd, J=1.52, 4.82 Hz, 2H), 7.25-7.37 (m, 5H), 6.94 (s, 1H), 5.34 (s, 1H);

LCMS: Mass found (M+1, 371);

HPLC>98%, Rt (min): 2.34.

2-Amino-5-(1-methyl-1H-pyrazol-3-yl)-N-pyridin-4-yl-nicotinamide ("A47")

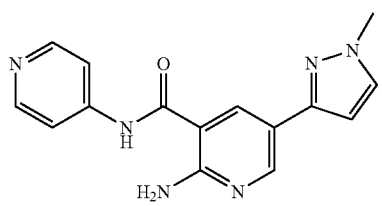 [SMILES: Cn1ccc(-c2cnc(N)c(C(=O)Nc3ccncc3)c2)n1]

¹H NMR (400 MHz, DMSO-d₆) δ [ppm] 10.65 (s, 1H), 8.59 (d, J=2.20 Hz, 1H), 8.48 (d, J=6.20 Hz, 2H), 8.36 (d, J=2.20 Hz, 1H), 7.73 (dd, J=2.12, 4.42 Hz, 3H), 7.07 (s, 1H), 6.66 (d, J=2.24 Hz, 1H), 3.87 (s, 3H);

LCMS: Mass found (M+1, 295);

HPLC>99%, Rt (min): 1.46.

2-Amino-5-(3,5-dimethyl-1H-pyrazol-4-yl)-N-pyridin-4-yl-nicotinamide ("A48")

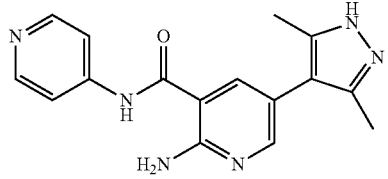 [SMILES: Cc1n[nH]c(C)c1-c1cnc(N)c(C(=O)Nc2ccncc2)c1]

¹H NMR (400 MHz, DMSO-d₆) δ [ppm] 12.29 (s, 1H), 10.36 (s, 1H), 8.45 (d, J=5.24 Hz, 2H), 8.09 (d, J=2.00 Hz, 1H), 8.00 (d, J=2.00 Hz, 1H), 7.70 (d, J=6.24 Hz, 2H), 7.01 (s, 1H), 2.16 (s, 6H);

LCMS: Mass found (M+1, 309);

HPLC>99%, Rt (min): 3.71.

2-Amino-N-pyridin-4-yl-5-thiophen-3-yl-nicotinamide ("A49")

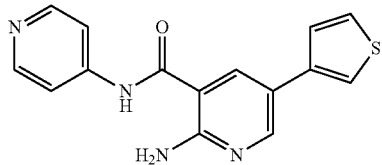 [SMILES: Nc1ncc(-c2ccsc2)cc1C(=O)Nc1ccncc1]

$^1$H NMR (400 MHz, DMSO-d$_6$) δ [ppm] 10.53 (s, 1H), 8.57 (d, J=2.28 Hz, 1H), 8.47 (d, J=6.24 Hz, 2H), 8.35 (d, J=2.28 Hz, 1H), 7.80-7.81 (m, 1H), 7.71 (dd, J=1.48, 4.86 Hz, 2H), 7.66 (dd, J=2.92, 5.00 Hz, 1H), 7.59 (dd, J=1.20, 5.00 Hz, 1H), 7.09 (s, 2H);

LCMS: Mass found (M+1, 297);
HPLC>95%, Rt (min): 1.88.

2-Amino-5-(1-methyl-1H-pyrrol-2-yl)-N-pyridin-4-yl-nicotinamide ("A50")

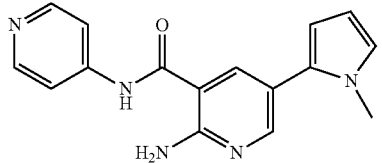 [SMILES: Cn1cccc1-c1cnc(N)c(C(=O)Nc2ccncc2)c1]

$^1$H NMR (400 MHz, DMSO-d$_6$) δ [ppm] 10.45 (s, 1H), 8.46 (d, J=6.12 Hz, 2H), 8.24 (d, J=2.16 Hz, 1H), 8.14 (d, J=2.12 Hz, 1H), 7.71 (d, J=6.32 Hz, 2H), 7.13 (s, 2H), 6.83 (t, J=2.00 Hz, 1H), 6.16 (dd, J=1.84, 3.52 Hz, 1H), 6.05-6.07 (m, 1H), 3.60 (s, 3H);

LCMS: Mass found (M+1, 294);
HPLC>95%, Rt (min): 1.84.

2-Amino-5-[1-(2-morpholin-4-yl-ethyl)-1H-pyrazol-4-yl]-N-pyridin-4-yl-nicotinamide ("A51")

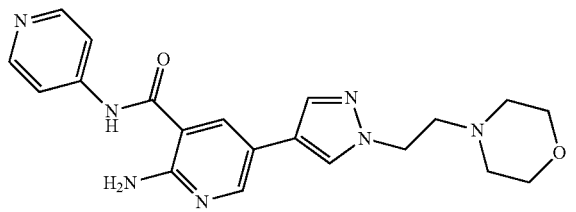 [SMILES: Nc1ncc(-c2cnn(CCN3CCOCC3)c2)cc1C(=O)Nc1ccncc1]

$^1$H NMR (400 MHz, DMSO-d$_6$) δ [ppm] 10.51 (s, 1H), 8.47 (dd, J=1.48, 4.82 Hz, 2H), 8.42 (dd, J=2.24, Hz, 1H), 8.18 (dd, J=2.24, Hz, 1H), 8.12 (s, 1H), 7.84-7.85 (m, 1H), 7.70 (dd, J=1.52, 4.80 Hz, 2H), 6.92 (s, 2H), 4.23 (t, J=6.64 Hz, 2H), 3.54 (t, J=4.68 Hz, 4H), 2.73 (t, J=6.64 Hz, 2H), 2.41 (t, J=4.40 Hz, 4H);

LCMS: Mass found (M+1, 394);
HPLC>99%, Rt (min): 3.84

2-Amino-5-benzo[b]thiophen-2-yl-N-pyridin-4-yl-nicotinamide ("A52")

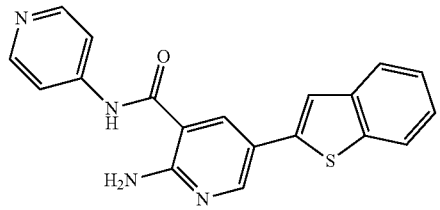 [SMILES: Nc1ncc(-c2cc3ccccc3s2)cc1C(=O)Nc1ccncc1]

$^1$H NMR (400 MHz, DMSO-d$_6$) δ [ppm] 11.41 (s, 1H), 8.73 (d, J=6.52 Hz, 2H), 8.65 (d, J=2.32 Hz, 1H), 8.15 (s, 1H), 8.15 (d, J=6.88 Hz, 2H), 7.97 (d, J=7.52 Hz, 1H), 7.79-7.82 (m, 2H), 7.32-7.43 (m, 4H);

LCMS: Mass found (M+1, 347);
HPLC>94%, Rt (min): 2.87.

5-(5-Acetyl-thiophen-2-yl)-2-amino-N-pyridin-4-yl-nicotinamide ("A53")

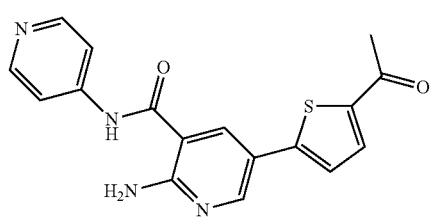 [SMILES: CC(=O)c1ccc(-c2cnc(N)c(C(=O)Nc3ccncc3)c2)s1]

$^1$H NMR (400 MHz, DMSO-d$_6$) δ [ppm] 10.62 (s, 1H), 8.60 (d, J=2.40 Hz, 1H), 8.49 (dd, J=1.40, 4.86 Hz, 2H), 8.37 (d, J=2.40 Hz, 1H), 7.95 (d, J=4.00 Hz, 1H), 7.71 (dd, J=1.56, 4.82 Hz, 2H), 7.59 (d, J=3.96 Hz, 1H), 7.39 (s, 2H), 2.48 (s, 3H)

LCMS: Mass found (M+1, 339);
HPLC>96%, Rt (min): 2.01.

2-Amino-5-(5-morpholin-4-ylmethyl-thiophen-2-yl)-N-pyridin-4-yl-nicotinamide ("A54")

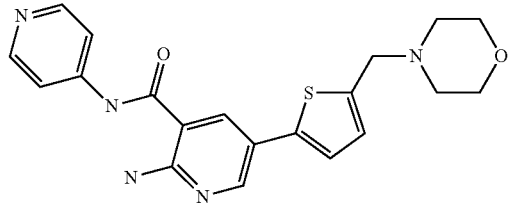 [SMILES: Nc1ncc(-c2ccc(CN3CCOCC3)s2)cc1C(=O)Nc1ccncc1]

$^1$H NMR (400 MHz, DMSO-d$_6$) δ [ppm] 8.27-8.34 (m, 3H), 7.60 (s, 2H), 7.06 (d, J=3.64 Hz, 1H), 6.93 (d, J=3.36 Hz, 1H), 3.65 (s, 2H), 3.58 (t, J=4.48 Hz, 4H), 2.41-2.49 (m, 4H), 1.50 (s, 3H);

LCMS: Mass found (M+1, 396);
HPLC>98%, Rt (min): 1.39.

2-Amino-5-(1H-indol-2-yl)-N-pyridin-4-yl-nicotinamide ("A55")

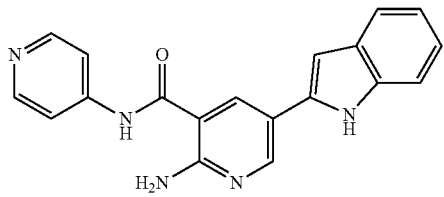 [SMILES: Nc1ncc(-c2cc3ccccc3[nH]2)cc1C(=O)Nc1ccncc1]

¹H NMR (400 MHz, DMSO-d₆) δ [ppm] 11.43 (s, 1H), 10.63 (s, 1H), 8.69 (d, J=2.04 Hz, 1H), 8.47-8.49 (m, 3H), 7.73 (d, J=5.12 Hz, 2H), 7.50 (d, J=7.64 Hz, 1H), 7.37 (d, J=7.96 Hz, 1H), 7.13 (s, 2H), 6.83-7.08 (m, 3H);

LCMS: Mass found (M+1, 330);

HPLC>99%, Rt (min): 2.60.

2-Amino-5-(1H-indol-3-yl)-N-pyridin-4-yl-nicotinamide ("A56")

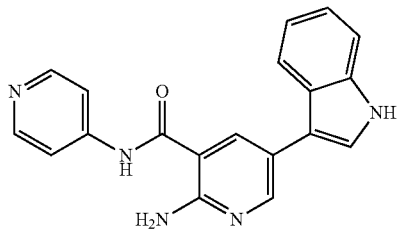 [SMILES: Nc1ncc(-c2c[nH]c3ccccc23)cc1C(=O)Nc1ccncc1]

¹H NMR (400 MHz, DMSO-d₆) δ [ppm] 11.33 (s, 1H), 10.55 (s, 1H), 8.46-8.51 (m, 3H), 8.30 (d, J=2.28 Hz, 2H), 7.83 (d, J=7.92 Hz, 1H), 7.67-7.82 (m, 2H), 7.44 (d, J=8.00 Hz, 1H), 7.05-7.16 (m, 2H), 6.93 (s, 2H);

LCMS: Mass found (M+1, 330);

HPLC>93%, Rt (min): 2.23.

2-Amino-N-pyridin-4-yl-5-(1H-pyrrol-2-yl)-nicotinamide ("A57")

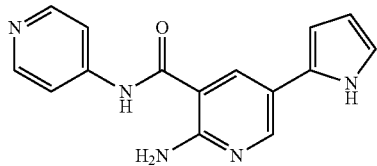 [SMILES: Nc1ncc(-c2ccc[nH]2)cc1C(=O)Nc1ccncc1]

¹H NMR (400 MHz, DMSO-d₆) δ [ppm] 11.15 (s, 1H), 10.54 (s, 1H), 8.46-8.48 (m, 3H), 8.22 (d, J=2.28 Hz, 1H), 7.71 (dd, J=1.52, 4.86 Hz, 2H), 6.89 (s, 2H), 6.82 (dd, J=2.56, 4.02 Hz, 1H), 6.42 (t, J=3.60 Hz, 1H), 6.10 (dd, J=2.52, 5.66 Hz, 1H), LCMS: Mass found (M+1, 280);

HPLC>94%, Rt (min): 1.71.

2-Amino-5-(1H-imidazo[1,2-a]pyridin-2-yl)-N-pyridin-4-yl-nicotinamide ("A58")

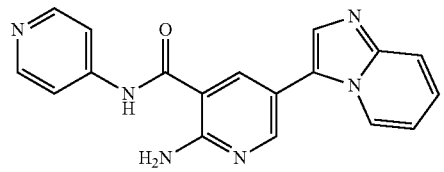 [SMILES: Nc1ncc(-c2cnc3ccccn23)cc1C(=O)Nc1ccncc1]

¹H NMR (400 MHz, DMSO-d₆) δ [ppm] 10.46 (s, 1H), 8.55 (d, J=6.88 Hz, 1H), 8.47 (d, J=6.04 Hz, 2H), 8.41 (d, J=2.12 Hz, 1H), 8.35 (d, J=2.00 Hz, 1H), 7.79 (s, 1H), 7.74-7.77 (m, 2H), 7.63-7.65 (m, 1H), 7.26-7.30 (m, 3H), 6.92-6.94 (m, 1H).

LCMS: Mass found (M+1, 331);

HPLC>91%, Rt (min): 3.68.

2-Amino-N-pyridin-4-yl-5-(1H-pyrrol-3-yl)-nicotinamide ("A59")

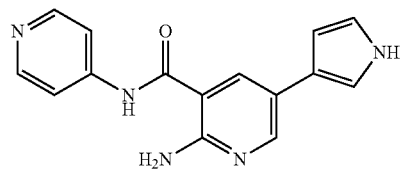 [SMILES: Nc1ncc(-c2cc[nH]c2)cc1C(=O)Nc1ccncc1]

¹H NMR (400 MHz, DMSO-d₆) δ [ppm] 10.90 (s, 1H), 10.50 (s, 1H), 8.47 (dd, J=1.52, 4.80 Hz, 2H), 8.40 (dd, J=2.24, Hz, 1H), 8.15 (dd, J=2.28, Hz, 1H), 7.72 (dd, J=1.52, 4.78 Hz, 2H), 7.18 (dd, J=1.88, 4.20 Hz, 1H), 6.79-6.82 (m, 3H), 6.43-6.45 (m, 1H);

LCMS: Mass found (M+1, 280);

HPLC>98%, Rt (min): 1.43.

2-Amino-5-benzofuran-3-yl-N-pyridin-4-yl-nicotinamide ("A60")

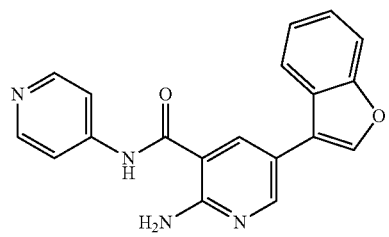 [SMILES: Nc1ncc(-c2coc3ccccc23)cc1C(=O)Nc1ccncc1]

¹H NMR (400 MHz, DMSO-d₆) δ [ppm] 10.58 (s, 1H), 8.54-8.55 (m, 3H), 8.33-8.36 (m, 2H), 7.95-7.97 (m, 1H), 7.72 (d, J=3.44 Hz, 2H), 7.65-7.65 (m, 1H), 7.32-7.41 (m, 2H), 7.13 (s, 2H);

LCMS: Mass found (M+1, 331);

HPLC>93%, Rt (min): 2.50.

2-Amino-5-(1-methyl-1H-pyrazol-4-yl)-N-pyridin-4-yl-nicotinamide ("A61")

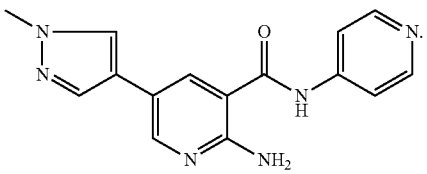 [SMILES: Cn1cc(-c2cnc(N)c(C(=O)Nc3ccncc3)c2)cn1]

EXAMPLE 11

LC-MS Conditions
Hewlett Packard HP 1200 series system with the following features: ion source: electrospray (positive mode); scan: 100-1000 m/e; fragmentation voltage: 100 V; gas temperature: 350° C., UV: 220 nm.
Method 1
HPLC/MS conditions:
column: Chromolith SpeedROD RP-18e, 50-4.6
gradient: A:B=96:4 to 0:100
    4% B→100% B: 0 min bis 2.8 min
    100% B: 2.8 min bis 3.3 min
    100% B→4% B: 3.3 min bis 4 min
flow rate: 2.4 ml/min
eluent A: water+0.05% formic acid
eluent B: acetonitrile+0.04% formic acid
wavelength: 220 nm
mass spectroscopy: positive mode
Method 2
HPLC/MS conditions:
column: Chromolith SpeedROD RP-18e, 50-4.6
gradient: A:B=100:0 to 0:100
    0% B→0% B: 0 min bis 0.5 min
    0% B→100% B 0.5 min bis 2.6 min
    100% B: 2.6 min bis 3.0 min
    100% B→0%B: 3.0 min bis 3.1 min
flow rate: 2.4 ml/min
eluent A: water+0.05% formic acid
eluent B: acetonitrile+0.04% formic acid
wavelength: 220 nm
mass spectroscopy: positive mode 2-Amino-5-(3-hydroxymethyl-phenyl)-N-pyridin-4-yl-nicotinamide ("A62")

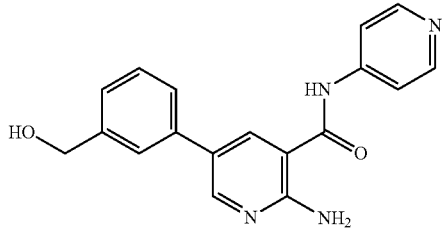 [SMILES: Nc1ncc(-c2cccc(CO)c2)cc1C(=O)Nc1ccncc1]

100 mg of 2-amino-5-bromo-N-pyridin-4-yl-nicotinamide and 62.2 mg 3-hydroxy-methyl)-benzeneboronic acid are dissolved in 4 ml of DMF. 90.4 mg $Na_2CO_3$ and 1 ml water are added under argon. 13.9 mg of [1,1-Bis(diphenylphosphino)ferrocene]dichloropalladium(II) are added. The mixture is stirred for 14 h at 100° C.

The reaction mixture is cooled to room temperature and the DMF is evaporated and the product was purified by chromatography.
45 mg of "A62" are obtained; method 1: HPLC/MS: 1.11 min, [M+H]=321;
$^1$H NMR (400 MHz, DMSO-$d_6$) δ [ppm] 9.01 (1 H, d, J 2.2), 8.88-8.83 (2 H, m), 8.67 (1 H, d, J 2.3), 8.34-8.29 (2 H, m), 7.79 (1 H, s), 7.69 (1 H, d, J 7.6), 7.52 (1 H, t, J 7.6), 7.46 (1 H, d, J 7.8), 4.65 (2 H, s).
The following compounds are obtained analogously:

2-Amino-5-(2-hydroxymethyl-phenyl)-N-pyridin-4-yl-nicotinamide ("A63")

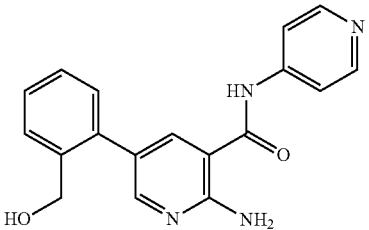 [SMILES: Nc1ncc(-c2ccccc2CO)cc1C(=O)Nc1ccncc1]

Reaction of 2-amino-5-bromo-N-pyridin-4-yl-nicotinamide with 2-(hydroxymethyl)-benzeneboronic acid gives "A63"; method 1: HPLC/MS: 1.07 min, [M+H]=321;
$^1$H NMR (500 MHz, DMSO-$d_6$/TFA-$d_1$) δ [ppm] 8.88 (1 H, d, J 2.1), 8.81 (2 H, d, J 7.2), 8.52 (1 H, d, J 2.1), 8.31 (2 H, d, J 7.3), 7.63 (1 H, d, J 7.3), 7.53-7.44 (3 H, m), 4.52 (2 H, s);

2-Amino-5-(2-tert-butylsulfamoyl-phenyl)-N-pyridin-4-yl-nicotinamide ("A64")

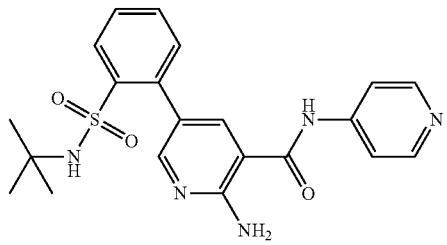 [SMILES: CC(C)(C)NS(=O)(=O)c1ccccc1-c1cnc(N)c(C(=O)Nc2ccncc2)c1]

Reaction of 2-amino-5-bromo-N-pyridin-4-yl-nicotinamide with 2-tert.-butyl-sulfamoyl-benzeneboronic acid gives "A64"; method 1: HPLC/MS: 1.41 min, [M+H]=426;
$^1$H NMR (400 MHz, DMSO-$d_6$/TFA-$d_1$) δ [ppm] 8.86-8.80 (3 H, m), 8.39 (1 H, d, J 2.1), 8.28 (2 H, d, J 7.3), 8.15 (1 H, dd, J 7.9, 1.2), 7.73 (2 H, dtd, J 31.4, 7.6, 1.4), 7.57 (1 H, dd, J 7.6, 1.2), 1.09 (9 H, s);

2-Amino-5-(4-amino-phenyl)-N-pyridin-4-yl-nicotinamide ("A65")

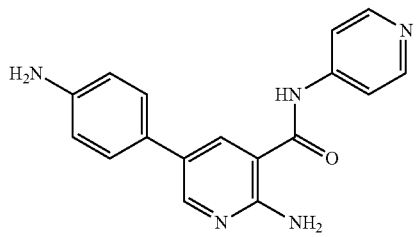 [SMILES: Nc1ccc(-c2cnc(N)c(C(=O)Nc3ccncc3)c2)cc1]

Reaction of 2-amino-5-bromo-N-pyridin-4-yl-nicotinamide with 4-aminophenyl-boronic acid hydrochloride gives "A65"; method 2: HPLC/MS: 1.53 min, [M+H]=306;
$^1$H NMR (400 MHz, DMSO-d$_6$/TFA-d$_1$) δ [ppm] 9.05 (1 H, d, J 2.2), 8.87 (2 H, d, J 7.5), 8.72 (1 H, d, J 2.2), 8.36 (2 H, d, J 7.3), 7.99 (2 H, d, J 8.5), 7.60-7.55 (2 H, m);

2-Amino-5-(2-formyl-phenyl)-N-pyridin-4-yl-nicotinamide ("A66")

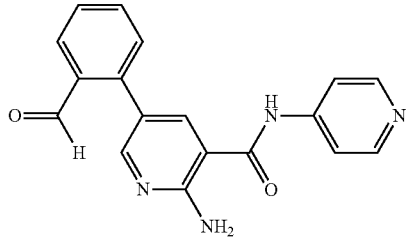 [SMILES: Nc1ncc(-c2ccccc2C=O)cc1C(=O)Nc1ccncc1]

Reaction of 2-amino-5-bromo-N-pyridin-4-yl-nicotinamide with 2-formylphenyl-boronic acid gives "A66"; method 1: HPLC/MS: 1.23 min, [M+H]=319;
$^1$H NMR (400 MHz, DMSO-d$_6$/TFA-d$_1$) δ [ppm] 10.08 (1 H, s), 8.88 (1 H, d, J 2.2), 8.81 (2 H, d, J 7.3), 8.51 (1 H, d, J 2.2), 8.32-8.28 (2 H, m), 8.11-8.07 (1 H, m), 7.83 (1 H, td, J 7.6, 1.5), 7.72 (1 H, t, J 7.2), 7.64 (1 H, dd, J 7.6, 0.9);

3-[6-Amino-5-(pyridin-4-ylcarbamoyl)-pyridin-3-yl]-benzoic acid ethyl ester ("A67")

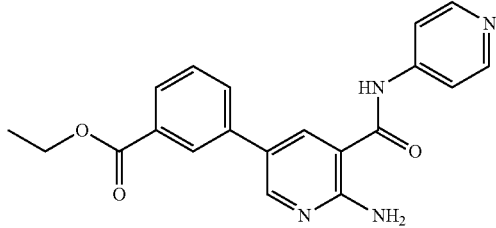 [SMILES: CCOC(=O)c1cccc(-c2cnc(N)c(C(=O)Nc3ccncc3)c2)c1]

Reaction of 2-amino-5-bromo-N-pyridin-4-yl-nicotinamide with 3-ethoxycarbonyl-phenylboronic acid gives "A67"; method 1: HPLC/MS: 1.48 min, [M+H]=363;
$^1$H NMR (400 MHz, DMSO-d$_6$/TFA-d$_1$) δ [ppm] 9.06 (1 H, d, J 2.2), 8.85 (2 H, d, J 7.3), 8.76 (1 H, d, J 2.2), 8.41 (1 H, t, J 1.7), 8.33 (2 H, d, J 7.3), 8.13-8.03 (2 H, m), 7.70 (1 H, t, J 7.8), 4.41 (2 H, q, J 7.1), 1.39 (3 H, t, J 7.1);

2-Amino-5-(4-hydroxymethyl-phenyl)-N-pyridin-4-yl-nicotinamide ("A68")

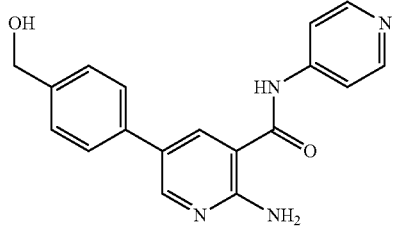 [SMILES: Nc1ncc(-c2ccc(CO)cc2)cc1C(=O)Nc1ccncc1]

Reaction of 2-amino-5-bromo-N-pyridin-4-yl-nicotinamide with 4-(hydroxymethyl)-phenylboronic acid; method 1: HPLC/MS: 1.12 min, [M+H]=321;
$^1$H NMR (400 MHz, DMSO-d$_6$/TFA-d$_1$) δ [ppm] 9.02 (1 H, d, J 2.2), 8.83 (2 H, d, J 7.3), 8.65 (1 H, d, J 2.2), 8.33 (2 H, d, J7.3), 7.79 (2 H, d, J 8.2), 7.54 (2 H, d, J 8.4), 4.63 (2 H, s);

2-Amino-5-(3-hydroxy-phenyl)-N-pyridin-4-yl-nicotinamide ("A69")

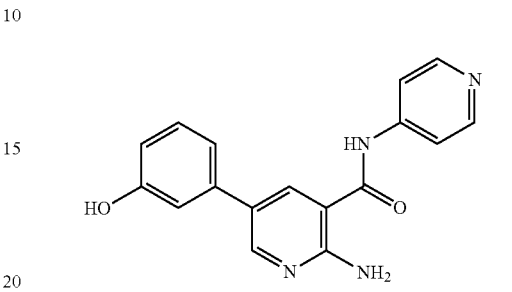

Reaction of 2-amino-5-bromo-N-pyridin-4-yl-nicotinamide with 3-hydroxyphenyl-boronic acid pinacol ester gives "A70"; method 1: HPLC/MS: 1.12 min, [M+H]=307.
$^1$H NMR (400 MHz, DMSO-d$_6$/TFA-d$_1$) δ [ppm] 9.02 (1 H, d, J 2.2), 8.82 (2 H, d, J 5.1), 8.62 (1 H, s), 8.34 (2 H, d, J 7.3), 7.36 (1 H, t, J 7.8), 7.22 (2 H, d, J 8.1), 6.96 (1 H, dd, J 7.5, 1.8);

2-[6-Amino-5-(pyridin-4-ylcarbamoyl)-pyridin-3-yl]-benzoic acid ethyl ester ("A70")

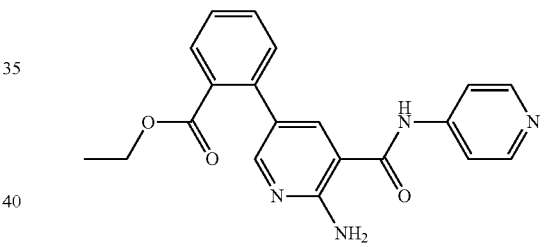

Reaction of 2-amino-5-bromo-N-pyridin-4-yl-nicotinamide with ethyl-2-(4,4,5,5-tetramethyl-1,3,2-dioxaborolan-2-yl)benzoate gives "A70"; method 1: HPLC/MS: 1.37 min, [M+H]=363;
$^1$H NMR (500 MHz, DMSO-d$_6$/TFA-d$_1$) δ [ppm] 8.86 (1 H, d, J 2.1), 8.79 (2 H, d, J 7.1), 8.40 (1 H, d, J 2.0), 8.32 (2 H, d, J 7.3), 8.12 (1 H, dd, J 7.8, 0.9), 7.75 (1 H, td, J 7.6, 1.1), 7.64 (1 H, td, J 7.7, 0.9), 7.57 (1 H, d, J 7.5), 4.23 (2 H, q, J 7.1), 1.22 (3 H, t);

4-[6-Amino-5-(pyridin-4-ylcarbamoyl)-pyridin-3-yl]-benzoic acid ethyl ester ("A71")

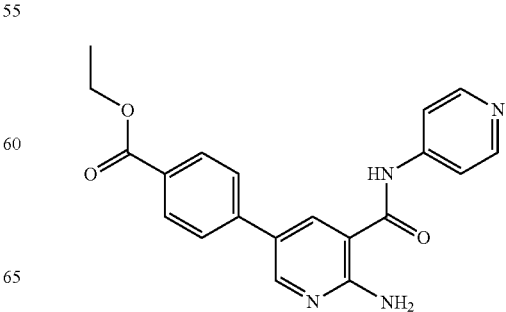

Reaction of 2-amino-5-bromo-N-pyridin-4-yl-nicotinamide with 4-ethoxycarbonyl-phenylboronic acid gives "A71"; method 1: HPLC/MS: 1.46 min, [M+H]=363;
$^1$H NMR (500 MHz, DMSO-d$_6$/TFA-d$_1$) δ [ppm] 9.08 (1 H, d, J 2.2), 8.84 (2 H, d, J 7.2), 8.77 (1 H, d, J 2.1), 8.33 (2 H, d, J 7.2), 8.17 (2 H, d, J 8.5), 7.97 (2 H, d, J 8.4), 4.38 (2 H, q, J 7.1), 1.38 (3 H, t, J 7.1);

2-Amino-5-(4-hydroxy-phenyl)-N-pyridin-4-yl-nicotinamide ("A72")

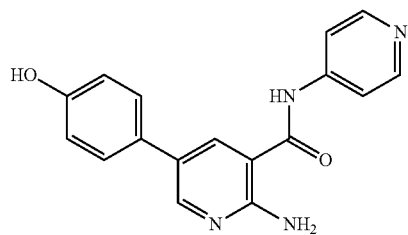 [SMILES: Nc1ncc(-c2ccc(O)cc2)cc1C(=O)Nc1ccncc1]

Reaction of 2-amino-5-bromo-N-pyridin-4-yl-nicotinamide with 4-hydroxybenzene-boronic acid gives "A72"; method 1: HPLC/MS: 1.07 min, [M+H]=307;
$^1$H NMR (500 MHz, DMSO-d$_6$/TFA-d$_1$) δ [ppm] 8.99 (1 H, d, J 2.1), 8.78 (2 H, dd, J 7.2, 2.4), 8.51 (1 H, t, J 2.1), 8.35 (2 H, d, J 7.2), 7.61 (2 H, dd, J 8.5, 1.8), 7.01 (2 H, d, J 8.6);

2-Amino-5-(2-hydroxy-phenyl)-N-pyridin-4-yl-nicotinamide ("A73")

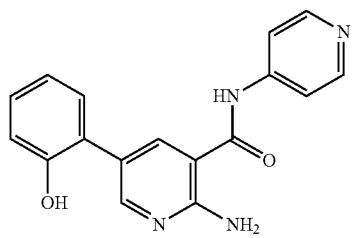 [SMILES: Nc1ncc(-c2ccccc2O)cc1C(=O)Nc1ccncc1]

Reaction of 2-amino-5-bromo-N-pyridin-4-yl-nicotinamide with 2-(4,4,5,5-tetramethyl-1,3,2-dioxaborolan-2-yl) phenol gives "A73"; method 1: HPLC/MS: 1.16 min, [M+H]=307;
$^1$H NMR (500 MHz, DMSO-d$_6$/TFA-d$_1$) δ [ppm] 8.95 (1 H, d, J 2.1), 8.83 (2 H, d, J 7.2), 8.62 (1 H, d, J 2.1), 8.30 (2 H, d, J 7.2), 7.53 (1 H, dd, J 7.7, 1.5), 7.32-7.27 (1 H, m), 7.11-7.07 (1 H, m), 7.03-6.98 (1 H, m);

2-Amino-5-(3-formyl-phenyl)-N-pyridin-4-yl-nicotinamide ("A74")

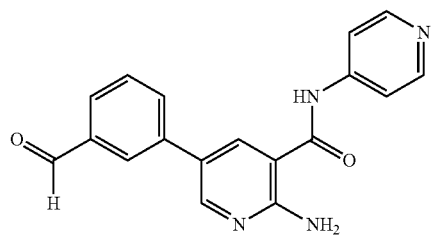 [SMILES: Nc1ncc(-c2cccc(C=O)c2)cc1C(=O)Nc1ccncc1]

Reaction of 2-amino-5-bromo-N-pyridin-4-yl-nicotinamide with 3-formylbenzene-boronic acid gives "A75"; method 1: HPLC/MS: 1.29 min, [M+H]=319;
$^1$H NMR (500 MHz, DMSO-d$_6$/TFA-d$_1$) δ [ppm] 10.13 (1 H, s), 9.13 (1 H, d, J 2.2), 8.83-8.75 (3 H, m), 8.36 (3 H, d, J 7.2), 8.14-8.02 (2 H, m), 7.78 (1 H, t, J 7.7);

2-Amino-5-(4-formyl-phenyl)-N-pyridin-4-yl-nicotinamide ("A75")

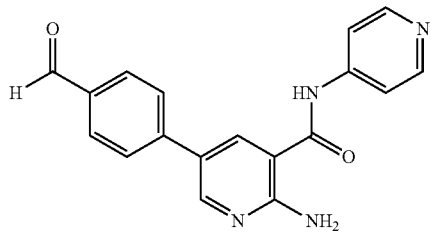 [SMILES: Nc1ncc(-c2ccc(C=O)cc2)cc1C(=O)Nc1ccncc1]

Reaction of 2-amino-5-bromo-N-pyridin-4-yl-nicotinamide with 4-formylbenzene-boronic acid gives "A75"; method 1: HPLC/MS: 1.29 min, [M+H]=319;
$^1$H NMR (500 MHz, DMSO-d$_6$/TFA-d$_1$) δ [ppm] 10.10 (1 H, s), 9.08 (1 H, d, J 2.2), 8.86 (2 H, d, J 7.2), 8.82 (1 H, d, J 2.2), 8.32 (2 H, d, J 7.3), 8.12-8.05 (4 H, m);

2-Amino-5-(3-aminomethyl-phenyl)-N-pyridin-4-yl-nicotinamide ("A76")

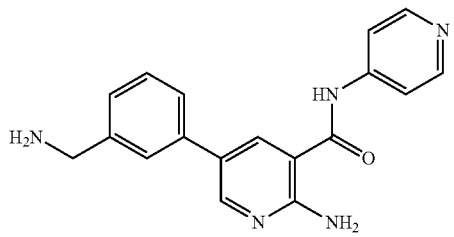 [SMILES: NCc1cccc(-c2cnc(N)c(C(=O)Nc3ccncc3)c2)c1]

Reaction of 2-amino-5-bromo-N-pyridin-4-yl-nicotinamide with 3-aminomethyl-phenylboronic acid hydrochloride gives "A76"; method 1: HPLC/MS: 0.94 min, [M+H]=320;
$^1$H NMR (500 MHz, DMSO-d$_6$/TFA-d$_1$) δ [ppm] 8.99 (1 H, d, J 2.3), 8.86 (2 H, d, J 7.3), 8.65 (1 H, d, J 2.2), 8.31 (2 H, d, J 7.3), 7.93 (1 H, s), 7.87 (1 H, d, J 7.6), 7.61 (2 H, dt, J 15.7, 7.7), 4.17 (2 H, s);

2-Amino-5-(4-aminomethyl-phenyl)-N-pyridin-4-yl-nicotinamide ("A77")

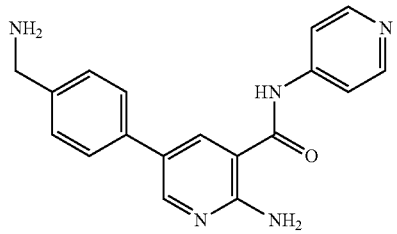

Reaction of 2-amino-5-bromo-N-pyridin-4-yl-nicotinamide with 4-aminomethyl-phenylboronic acid hydrochloride gives "A77"; method 1: HPLC/MS: 1.07 min, [M+H]=320;

¹H NMR (500 MHz, DMSO-d₆/TFA-d₁) δ [ppm] 9.02 (1 H, d, J 2.2), 8.86 (2 H, d, J 7.3), 8.73 (1 H, d, J 2.3), 8.31 (2 H, d, J 7.3), 7.91 (2 H, d, J 8.4), 7.67 (2 H, d, J 8.4), 4.15 (2 H, s);

2-Amino-N-pyridin-4-yl-5-(3-sulfamoyl-phenyl)-nicotinamide ("A78")

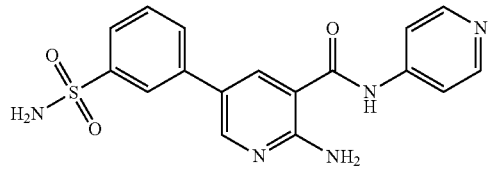 [SMILES: Nc1ncc(-c2cccc(S(N)(=O)=O)c2)cc1C(=O)Nc1ccncc1]

Reaction of 2-amino-5-bromo-N-pyridin-4-yl-nicotinamide with benzenesulfon-amide-3-boronic acid pinacol ester gives "A78"; method 1: HPLC/MS: 1.13 min, [M+H]=370;
¹H NMR (500 MHz, DMSO-d₆/TFA-d₁) δ [ppm] 9.01 (1 H, d, J 2.2), 8.86 (2 H, d, J 7.3), 8.74 (1 H, d, J 2.3), 8.33-8.28 (3 H, m), 8.05 (1 H, d, J 7.8), 7.98 (1 H, d, J 7.9), 7.77 (1 H, t, J 7.9);

2-Amino-5-[3-(4-hydroxy-piperidine-1-sulfonyl)-phenyl]-N-pyridin-4-yl-nicotinamide ("A79")

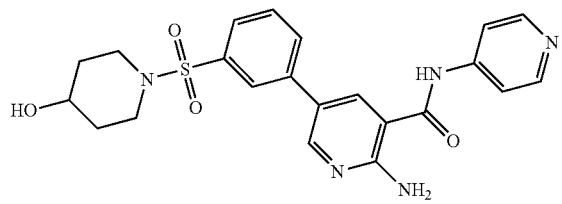 [SMILES: Nc1ncc(-c2cccc(S(=O)(=O)N3CCC(O)CC3)c2)cc1C(=O)Nc1ccncc1]

Reaction of 2-amino-5-bromo-N-pyridin-4-yl-nicotinamide with 1-[3-(4,4,5,5-tetramethyl-[1,3,2]dioxaborolan-2-yl)-benzenesulfonyl]-piperidin-4-ol gives "A79"; method 1: HPLC/MS: 1.29 min, [M+H]=454;
¹H NMR (400 MHz, DMSO-d₆/TFA-d₁) δ [ppm] 9.01 (1 H, d, J 2.3), 8.86 (2 H, d, J 7.3), 8.80 (1 H, d, J 2.2), 8.30 (2 H, d, J 7.3), 8.19-8.13 (2 H, m), 7.87-7.80 (2 H, m), 3.64-3.57 (1 H, m), 3.25-3.17 (2 H, m), 2.93-2.89 (2 H, m), 1.83-1.75 (2 H, m), 1.58-1.44 (2 H, m);

4-[6-Amino-5-(pyridin-4-ylcarbamoyl)-pyridin-3-yl]-2-fluoro-benzoic acid methyl ester ("A80")

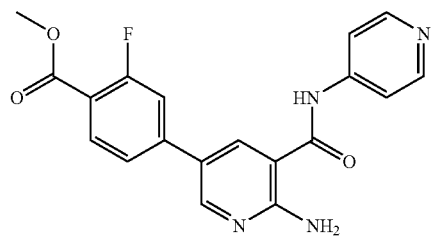 [SMILES: COC(=O)c1ccc(-c2cnc(N)c(C(=O)Nc3ccncc3)c2)cc1F]

Reaction of 2-amino-5-bromo-N-pyridin-4-yl-nicotinamide with 3-fluoro-4-methoxycarbonyl-phenylboronic acid gives "A80"; method 1: HPLC/MS: 1.48 min, [M+H]=367;

¹H NMR (400 MHz, DMSO-d₆/TFA-d₁) δ [ppm] 9.10 (1 H, d, J 2.2), 8.84 (3 H, t, J 4.8, 2.5), 8.34 (2 H, d, J 7.3), 8.09 (1 H, t, J 8.0), 7.87 (1 H, dd, J 12.2, 1.6), 7.80 (1 H, dd, J 8.2, 1.7), 3.92 (3H, s);

{2-[6-Amino-5-(pyridin-4-ylcarbamoyl)-pyridin-3-yl]-phenyl}-carbamic acid tert.-butyl ester ("A81")

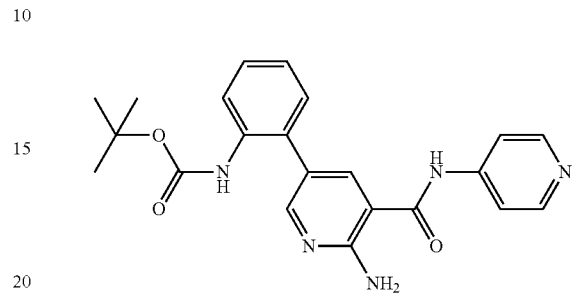

Reaction of 2-amino-5-bromo-N-pyridin-4-yl-nicotinamide with [2-(4,4,5,5-tetramethyl-[1,3,2]dioxaborolan-2-yl)-phenyl]-carbamic acid tert-butyl ester gives "A81"; method 1: HPLC/MS: 1.38 min, [M+H]=406;

{3-[6-Amino-5-(pyridin-4-ylcarbamoyl)-pyridin-3-yl]-phenyl}-carbamic acid tert.-butyl ester ("A82")

Reaction of 2-amino-5-bromo-N-pyridin-4-yl-nicotinamide with 3-(N-Boc-amino)phenylboronic acid gives "A82"; method 1: HPLC/MS: 1.56 min, [M+H]=406.

EXAMPLE 12

2-Amino-5-{4-[(2-methoxy-ethyl)-methyl-carbamoyl]-phenyl}-N-pyridin-4-yl-nicotinamide ("A83")

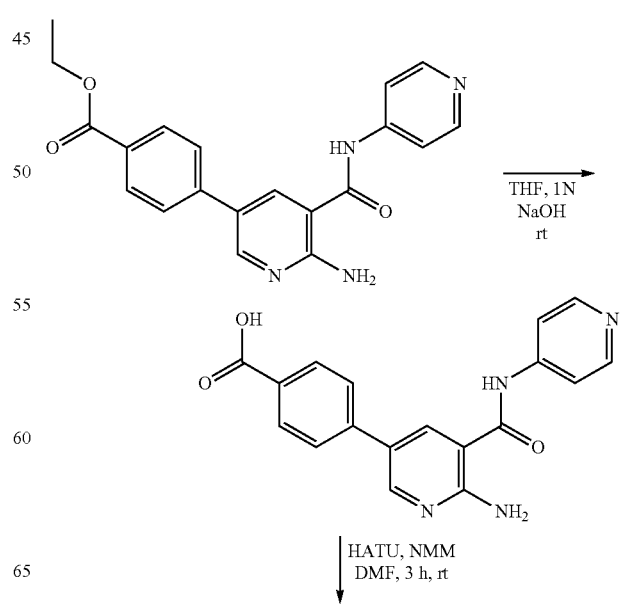

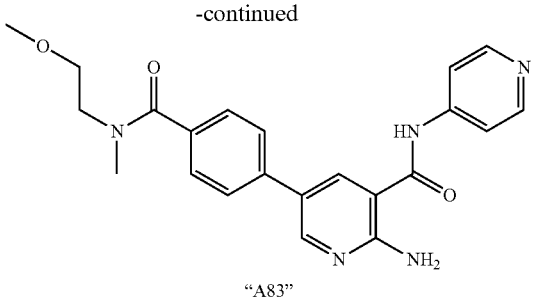

"A83"

12.1 4-[6-Amino-5-(pyridin-4-ylcarbamoyl)-pyridin-3-yl]-benzoic acid ("A31")

A solution of 4-[6-amino-5-(pyridin-4-ylcarbamoyl)-pyridin-3-yl]-benzoic acid ethyl ester (290 mg, 0.08 mmol), THF (5 mL) and 1N NaOH (4 mL, 25.0) is stirred at room temperature for 14 h. The THF is removed in vacuo and the mixture acidified with 1N HCl.

The resulting precipitate is filtered off, washed with water and dried. 260 mg of the desired product are obtained as a white solid; method 1: HPLC/MS: 1.21 min, [M+H]=335;

$^1$H NMR (400 MHz, DMSO-d$_6$/TFA-d$_1$) δ [ppm] 9.13 (1 H, s), 8.93-8.70 (4 H, m), 8.38 (2 H, d, J 6.6), 7.97 (2 H, d, J 8.4), 7.83 (1 H, d, J 8.5).

Using the above mentioned procedure the following compounds are obtained analogously:

3-[6-Amino-5-(pyridin-4-ylcarbamoyl)-pyridin-3-yl]-benzoic acid ("A84")

Reaction of 3-[6-amino-5-(pyridin-4-ylcarbamoyl)-pyridin-3-yl]-benzoic acid ethyl ester gives "A84"; method 1: HPLC/MS: 1.21 min, [M+H]=335;

$^1$H NMR (500 MHz, DMSO-d$_6$/TFA-d$_1$) δ [ppm] 9.12 (1 H, d, J 2.2), 8.85 (2 H, d, J 7.2), 8.78 (1 H, d, J 2.2), 8.44 (1 H, s), 8.37 (2 H, d, J 7.2), 8.10 (2 H, d, J 7.9), 7.68 (1 H, t, J 7.8);

2-[6-Amino-5-(pyridin-4-ylcarbamoyl)-pyridin-3-yl]-benzoic acid ("A85")

Reaction of 2-[6-amino-5-(pyridin-4-ylcarbamoyl)-pyridin-3-yl]-benzoic acid ethyl ester gives "A85"; method 1: HPLC/MS: 1.15 min, [M+H]=335;

$^1$H NMR (500 MHz, DMSO-d$_6$/TFA-d$_1$) δ [ppm] 8.86 (1 H, d, J 2.1), 8.79 (2 H, d, J 7.1), 8.40 (1 H, d, J 2.0), 8.32 (2 H, d, J 7.3), 8.12 (1 H, dd, J 7.8, 0.9), 7.75 (1 H, td, J 7.6, 1.1), 7.64 (1 H, td, J 7.7, 0.9), 7.57 (1 H, d, J 7.5);

4-[6-Amino-5-(pyridin-4-ylcarbamoyl)-pyridin-3-yl]-2-fluoro-benzoic acid ("A86")

Reaction of 4-[6-amino-5-(pyridin-4-ylcarbamoyl)-pyridin-3-yl]-2-fluoro-benzoic acid methyl ester gives "A86"; method 1: HPLC/MS: 1.22 min, [M+H]=353;

$^1$H NMR (400 MHz, DMSO-d$_6$/TFA-d$_1$) δ [ppm] 9.13 (1 H, d, J 2.2), 8.83 (3 H, t, J 4.7), 8.37 (2 H, d, J 7.4), 8.10 (1 H, t, J 8.0), 7.85 (1 H, dd, J 12.1, 1.7), 7.78 (1 H, dd, J 8.2, 1.7).

12.2 2-Amino-5-{4-[(2-methoxy-ethyl)-methyl-carbamoyl]-phenyl}-N-pyridin-4-yl-nicotinamide ("A83")

60 mg (0.18 mmol) of 4-[6-amino-5-(pyridin-4-ylcarbamoyl)-pyridin-3-yl]-benzoic acid and 23.13 μl (0.22 mmol) of N-(methoxyethyl)methylamine are dissolved in 2 mL DMF. 102.36 mg HATU ((2-(7-aza-1H-benzotriazole-1-yl)-1,1,3,3-tetramethyl-uronium hexafluorophosphate) and 59.19 μL N-methylmorpholine are added to the solution. The mixture is stirred for 3 h at room temperature. The DMF is evaporated and the product is purified by chromatography.

16 mg of "A83" are obtained; method 1: HPLC/MS: 1.22 min, [M+H]=406;

$^1$H NMR (500 MHz, DMSO-d$_6$/TFA-d$_1$) δ [ppm] 9.05 (1 H, d, J 2.2), 8.86 (2 H, d, J 7.3), 8.74 (1 H, d, J 2.2), 8.31 (2 H, d, J 7.3), 7.89 (2 H, d, J 8.0), 7.60 (2 H, d, J 8.3), 3.75-3.57 (2 H, m), 3.53-3.41 (3 H, m), 3.38-3.19 (2 H, m), 3.04 (3 H, s).

Using the above mentioned procedure the following compounds are obtained analogously:

2-Amino-5-(4-diethylcarbamoyl-phenyl)-N-pyridin-4-yl-nicotinamide ("A87")

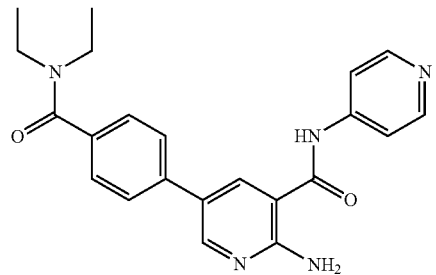 [SMILES: CCN(CC)C(=O)c1ccc(-c2cnc(N)c(C(=O)Nc3ccncc3)c2)cc1]

Reaction of 4-[6-amino-5-(pyridin-4-ylcarbamoyl)-pyridin-3-yl]-benzoic acid with diethyl amine gives "A87"; method 1: HPLC/MS: 1.36 min, [M+H]=390;

$^1$H NMR (500 MHz, DMSO-d$_6$/TFA-d$_1$) δ [ppm] 9.05 (1 H, d, J 2.3), 8.86 (2 H, d, J 7.3), 8.74 (1 H, d, J 2.2), 8.31 (2 H, d, J 7.3), 7.90 (2 H, d, J 8.4), 7.55 (2 H, d, J 8.3), 3.60-3.17 (4 H, m), 1.29-1.00 (6 H, m);

2-Amino-5-(4-carbamoyl-phenyl)-N-pyridin-4-yl-nicotinamide ("A88")

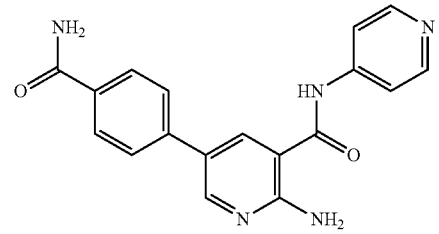 [SMILES: NC(=O)c1ccc(-c2cnc(N)c(C(=O)Nc3ccncc3)c2)cc1]

Reaction of 4-[6-amino-5-(pyridin-4-ylcarbamoyl)-pyridin-3-yl]-benzoic acid with ammonia gives "A88"; method 1: HPLC/MS: 1.10 min, [M+H]=334;

$^1$H NMR (500 MHz, DMSO-d$_6$/TFA-d$_1$) δ [ppm] 9.06 (1 H, d, J 2.2), 8.86 (2 H, d, J 7.2), 8.77 (1 H, d, J 2.2), 8.31 (2 H, d, J 7.2), 8.11 (2 H, d, J 8.4), 7.94 (2 H, d, J 8.4);

2-Amino-5-{4-[bis-(2-methoxy-ethyl)-carbamoyl]-phenyl}-N-pyridin-4-yl-nicotinamide ("A89")

Reaction of 4-[6-amino-5-(pyridin-4-ylcarbamoyl)-pyridin-3-yl]-benzoic acid with bis-(2-methoxy-ethyl)-amine gives "A89"; method 1: HPLC/MS: 1.30 min, [M+H]=450;

$^1$H NMR (500 MHz, DMSO-d$_6$/TFA-d$_1$) δ [ppm] 9.08 (1 H, d, J 2.2), 8.83 (2 H, d, J 7.2), 8.72 (1 H, d, J 2.1), 8.34 (2 H, d, J 7.3), 7.88 (2 H, d, J 8.2), 7.59 (2 H, d, J 8.3), 3.73-3.26 (14 H, m);

2-Amino-5-{4-[(2-dimethylamino-ethyl)-methyl-carbamoyl]-phenyl}-N-pyridin-4-yl-nicotinamide ("A90")

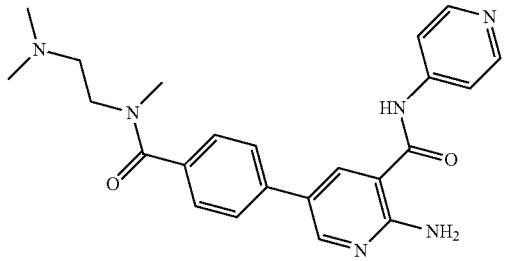 [SMILES: CN(C)CCN(C)C(=O)c1ccc(-c2cnc(N)c(C(=O)Nc3ccncc3)c2)cc1]

Reaction of 4-[6-amino-5-(pyridin-4-ylcarbamoyl)-pyridin-3-yl]-benzoic acid with N,N,N'-trimethylethylenediamine gives "A90"; method 2: HPLC/MS: 1.55 min, [M+H] 419;

$^1$H NMR (500 MHz, DMSO-d$_6$/TFA-d$_1$) δ [ppm] 9.08 (1 H, d, J 2.1), 8.80 (2 H, dd, J 7.3, 1.1), 8.71 (1 H, d, J 2.0), 8.35 (2 H, d, J 7.3), 7.91 (2 H, d, J 8.1), 7.69 (2 H, d, J 8.1), 3.90 (2 H, t), 3.46 (2 H, t), 3.05 (3 H, s), 2.95 (6 H, s);

2-Amino-5-{4-[(2-dimethylamino-ethyl)-ethyl-carbamoyl]-phenyl}-N-pyridin-4-yl-nicotinamide ("A91")

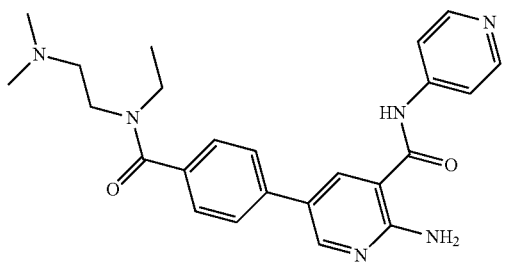 [SMILES: CCN(CCN(C)C)C(=O)c1ccc(-c2cnc(N)c(C(=O)Nc3ccncc3)c2)cc1]

Reaction of 4-[6-amino-5-(pyridin-4-ylcarbamoyl)-pyridin-3-yl]-benzoic acid with N'-ethyl-N,N-dimethyl-ethane-1,2-diamine gives "A91"; method 1: HPLC/MS: 1.08 min, [M+H]=433;

$^1$H NMR (500 MHz, DMSO-d$_6$/TFA-d$_1$) δ [ppm] 9.09 (1 H, d, J 2.2), 8.80 (2 H, d, J 7.3), 8.71 (1 H, d, J 2.2), 8.36 (2 H, d, J 7.4), 7.91 (2 H, d, J 8.3), 7.64 (2 H, d, J 8.3), 3.86 (2 H, t), 3.44 (2 H, t, J 6.4), 3.41-3.27 (2 H, m), 2.98 (6 H, s), 1.14 (3 H, t, J 6.6);

2-Amino-5-[4-(2-methoxy-ethylcarbamoyl)-phenyl]-N-pyridin-4-yl-nicotinamide ("A92")

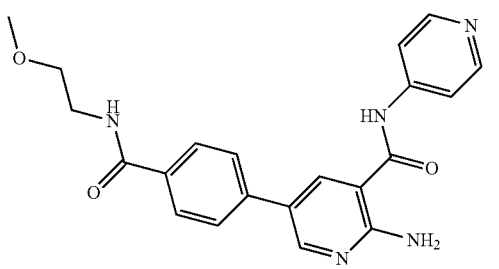 [SMILES: COCCNC(=O)c1ccc(-c2cnc(N)c(C(=O)Nc3ccncc3)c2)cc1]

Reaction of 4-[6-amino-5-(pyridin-4-ylcarbamoyl)-pyridin-3-yl]-benzoic acid with 2-methoxy-ethylamine gives "A92"; method 1: HPLC/MS: 1.25 min, [M+H]=392;

$^1$H NMR (500 MHz, DMSO-d$_6$/TFA-d$_1$) δ [ppm] 9.10 (1 H, d, J 2.2), 8.81 (2 H, d, J 7.3), 8.74 (1 H, d, J 2.2), 8.35 (2 H, d, J 7.4), 8.11 (2 H, d, J 8.5), 7.91 (2 H, d, J 8.5), 3.55 (4 H, s), 3.34 (3 H, s);

2-Amino-5-{4-[bis-(2-hydroxy-ethyl)-carbamoyl]-phenyl}-N-pyridin-4-yl-nicotinamide ("A93")

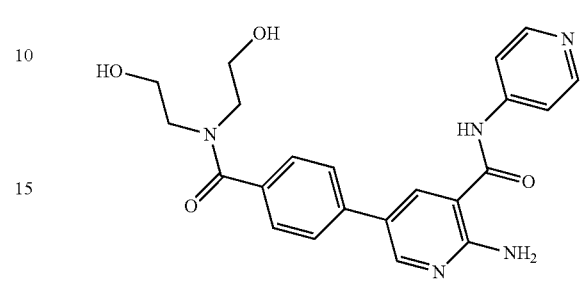

Reaction of 4-[6-amino-5-(pyridin-4-ylcarbamoyl)-pyridin-3-yl]-benzoic acid with 2-(2-hydroxy-ethylamino)-ethanol gives "A93"; method 2: HPLC/MS: 1.62 min, [M+H]=422;

$^1$H NMR (500 MHz, DMSO-d$_6$) δ [ppm] 8.57 (1 H, d, J 2.3), 8.49 (2 H, dd, J 4.8, 1.5), 8.39 (1 H, d, J 2.3), 7.77 (2 H, d, J 8.3), 7.73 (2 H, dd, J 4.8, 1.5), 7.49 (2 H, d, J 8.3), 3.64-3.46 (8 H, m);

2-Amino-5-[4-(3-methoxy-propylcarbamoyl)-phenyl]-N-pyridin-4-yl-nicotinamide ("A94")

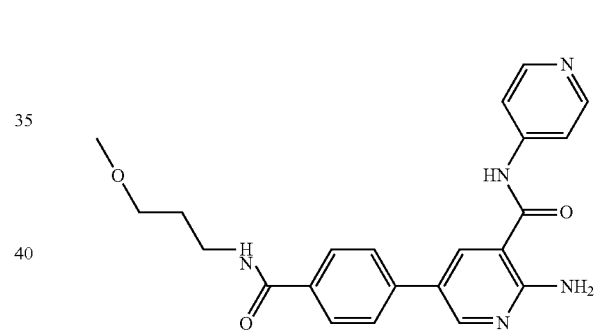

Reaction of 4-[6-amino-5-(pyridin-4-ylcarbamoyl)-pyridin-3-yl]-benzoic acid with 3-methoxy-propylamine gives "A94"; method 1: HPLC/MS: 1.30 min, [M+H]=406;

$^1$H NMR (500 MHz, DMSO-d$_6$/TFA-d$_1$) δ [ppm] 9.11 (1 H, d, J 2.2), 8.76 (2 H, d), 8.69 (1 H, d, J 2.1), 8.37 (2 H, d, J 7.3), 8.07 (2 H, d, J 3.3), 7.88 (2 H, d, J 8.4), 3.48-3.45 (4 H, m), 3.31 (3 H, s), 1.88 (2 H, p, J 6.5);

2-Amino-5-{4-[methyl-(3-methyl-3H-imidazol-4-ylmethyl)-carbamoyl]-phenyl}-N-pyridin-4-yl-nicotinamide ("A95")

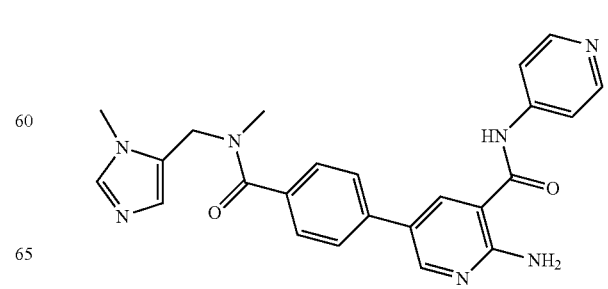

Reaction of 4-[6-amino-5-(pyridin-4-ylcarbamoyl)-pyridin-3-yl]-benzoic acid with methyl-(3-methyl-3H-imidazol-4-ylmethyl)-amine gives "A95"; method 1: HPLC/MS: 1.07 min, [M+H]=442;

$^1$H NMR (500 MHz, DMSO-d$_6$/TFA-d$_1$) δ [ppm] 9.09 (1 H, s), 9.08 (1 H, d, J 2.1), 8.79 (2 H, d, J 7.3), 8.70 (1 H, d, J 2.0), 8.35 (2 H, d, J 7.3), 7.89 (2 H, d, J 8.3), 7.71 (1 H, s), 7.68 (2 H, d, J 8.3), 3.97 (2 H, s), 3.00 (3 H, s), 2.79 (3 H, s);

2-{4-[6-Amino-5-(pyridin-4-ylcarbamoyl)-pyridin-3-yl]-benzoylamino}-ethyl carbamic acid tert.-butyl ester ("A96")

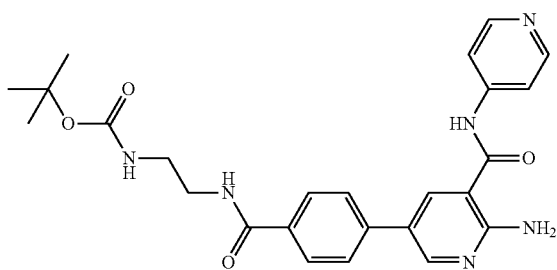 [SMILES: CC(C)(C)OC(=O)NCCNC(=O)c1ccc(-c2cnc(N)c(C(=O)Nc3ccncc3)c2)cc1]

Reaction of 4-[6-amino-5-(pyridin-4-ylcarbamoyl)-pyridin-3-yl]-benzoic acid with (2-amino-ethyl)-carbamic acid tert-butyl ester gives "A96"; method 1: HPLC/MS: 1.47 min, [M+H]=477;

2-Amino-5-{3-[(2-methoxy-ethyl)-methyl-carbamoyl]-phenyl}-N-pyridin-4-yl-nicotinamide ("A97")

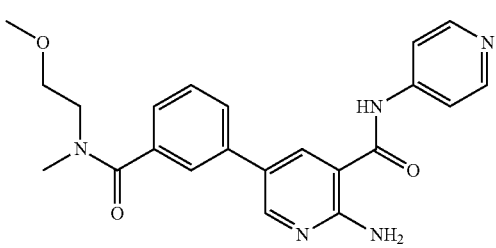 [SMILES: COCCN(C)C(=O)c1cccc(-c2cnc(N)c(C(=O)Nc3ccncc3)c2)c1]

Reaction of 3-[6-amino-5-(pyridin-4-ylcarbamoyl)-pyridin-3-yl]-benzoic acid with N-(methoxy-ethyl)-methyl-amine gives "A97"; method 1: HPLC/MS: 1.23 min, [M+H]=406;

$^1$H NMR (500 MHz, DMSO-d$_6$/TFA-d$_1$) δ [ppm] 9.03 (1 H, s), 8.86 (2 H, d, J 7.3), 8.74 (1 H, s), 8.31 (2 H, d, J 7.4), 7.88 (2 H, d, J 1.6), 7.62 (1 H, t, J 7.9), 7.49 (1 H, d, J 7.7), 3.73-2.96 (10 H, m);

2-Amino-5-(3-diethylcarbamoyl-phenyl)-N-pyridin-4-yl-nicotin-amide ("A98")

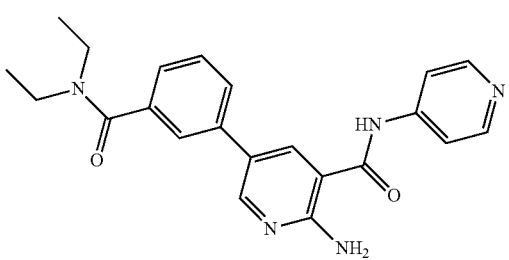 [SMILES: CCN(CC)C(=O)c1cccc(-c2cnc(N)c(C(=O)Nc3ccncc3)c2)c1]

Reaction of 3-[6-amino-5-(pyridin-4-ylcarbamoyl)-pyridin-3-yl]-benzoic acid with diethyl amine gives "A98"; method 1: HPLC/MS: 1.37 min, [M+H]=390;

$^1$H NMR (500 MHz, DMSO-d$_6$/TFA-d$_1$) δ [ppm] 9.04 (1 H, d, J 2.1), 8.85 (2 H, d, J 7.2), 8.74 (1 H, d, J 2.1), 8.31 (2 H, d, J 7.2), 7.89 (1H, d, J 8.1), 7.84 (1H, s), 7.62 (1 H, t, J 7.7), 7.45 (1 H, d, J 7.5), 3.57-3.23 (4 H, m), 1.28-1.01 (6 H, m);

2-Amino-5-(3-carbamoyl-phenyl)-N-pyridin-4-yl-nicotinamide ("A99")

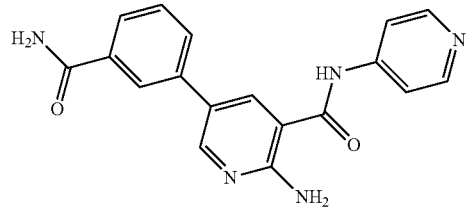 [SMILES: NC(=O)c1cccc(-c2cnc(N)c(C(=O)Nc3ccncc3)c2)c1]

Reaction of 3-[6-amino-5-(pyridin-4-ylcarbamoyl)-pyridin-3-yl]-benzoic acid with ammonia gives "A99"; method 2: HPLC/MS: 1.64 min, [M+H]=334.

$^1$H NMR (500 MHz, DMSO-d$_6$/TFA-d$_1$) δ [ppm] 9.07 (1 H, d, J 2.2), 8.85 (2 H, d, J 7.3), 8.76 (1 H, d, J 2.2), 8.36 (1 H, t, J 1.7), 8.32 (2 H, d, J 7.3), 8.00 (2 H, td, J 8.3, 1.6), 7.65 (1 H, t, J 7.8);

2-Amino-5-(2-diethylcarbamoyl-phenyl)-N-pyridin-4-yl-nicotin-amide ("A100")

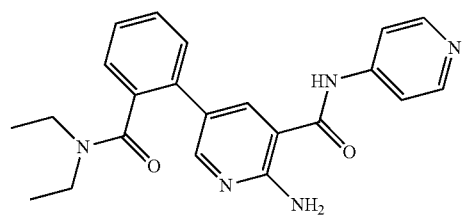 [SMILES: CCN(CC)C(=O)c1ccccc1-c1cnc(N)c(C(=O)Nc2ccncc2)c1]

Reaction of 2-[6-amino-5-(pyridin-4-ylcarbamoyl)-pyridin-3-yl]-benzoic acid with diethyl amine gives "A100"; method 2: HPLC/MS: 1.35 min, [M+H]=390;

$^1$H NMR (500 MHz, DMSO-d$_6$) δ [ppm] 8.83 (2 H, d, J 7.3), 8.81 (1 H, d, J 2.2), 8.35 (1 H, d, J 2.1), 8.31 (2 H, d, J 7.3), 7.70-7.67 (1 H, m), 7.62 (1 H, td, J 7.6, 1.3), 7.56 (1 H, ddd, J 6.0, 5.5, 1.4), 7.45 (1 H, dd, J 7.5, 1.1), 3.47-3.30 (2 H, m), 3.03 (2 H, q, J 7.0), 1.02-0.91 (3 H, m);

2-Amino-5-(2-carbamoyl-phenyl)-N-pyridin-4-yl-nicotinamide ("A101")

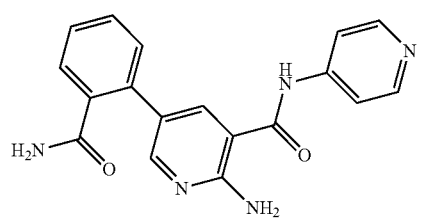 [SMILES: NC(=O)c1ccccc1-c1cnc(N)c(C(=O)Nc2ccncc2)c1]

Reaction of 2-[6-amino-5-(pyridin-4-ylcarbamoyl)-pyridin-3-yl]-benzoic acid with ammonia gives "A101"; method 1: HPLC/MS: 1.05 min, [M+H]=334;

¹H NMR (500 MHz, DMSO-d₆/TFA-d₁) δ [ppm] 8.86 (1 H, d, J 2.1), 8.79 (2 H, d, J 7.1), 8.40 (1 H, d, J 2.0), 8.32 (2 H, d, J 7.3), 8.12 (1 H, dd, J 7.8, 0.9), 7.75 (1 H, td, J 7.6, 1.1), 7.64 (1 H, td, J 7.7, 0.9), 7.57 (1 H, d, J 7.5);

2-Amino-5-{3-fluoro-4-[(2-methoxy-ethyl)-methyl-carbamoyl]-phenyl}-N-pyridin-4-yl-nicotinamide ("A102")

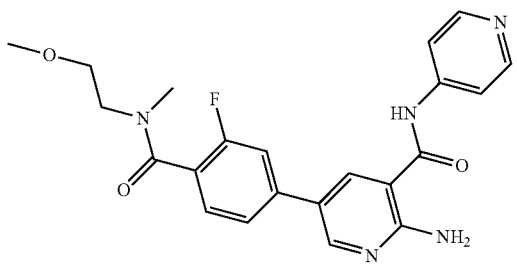 [SMILES: COCCN(C)C(=O)c1ccc(-c2cnc(N)c(C(=O)Nc3ccncc3)c2)cc1F]

Reaction of 4-[6-amino-5-(pyridin-4-ylcarbamoyl)-pyridin-3-yl]-2-fluoro-benzoic acid with N-(methoxyethyl)-methylamine gives "A102"; method 1: HPLC/MS: 1.34 min, [M+H]=424;

¹H NMR (500 MHz, DMSO-d₆/TFA-d₁) δ [ppm] 9.09 (1 H, d, J 2.0), 8.81 (2 H, d, J 7.2), 8.76 (1 H, d, J 2.2), 8.35 (2 H, d, J 7.3), 8.08 (1 H, s), 7.82-7.69 (1 H, m), 7.57 (1 H, td, J 7.6, 2.9), 3.72 (1 H, t, J 5.5), 3.63 (1 H, t, J 5.5), 3.43 (2 H, dd, J 10.0, 4.1), 3.36 (2 H, s), 3.23 (1 H, s), 3.10 (2 H, s), 2.97 (1 H, s);

EXAMPLE 13

2-Amino-5-(2-amino-phenyl)-N-pyridin-4-yl-nicotinamide ("A103")

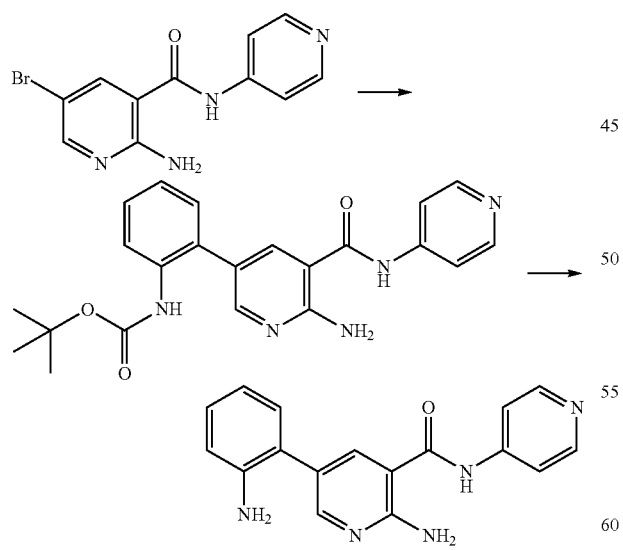

13.1 2-[6-Amino-5-(pyridin-4-ylcarbamoyl)-pyridin-3-yl]-phenyl-carbamic acid tert.-butyl ester The title compound is obtained from 2-amino-5-bromo-N-(2-ethoxy-pyridin-4-yl)-nicotinamide and [2-(4,4,5,5-tetramethyl-[1,3,2]dioxaborolan-2-yl)-phenyl]-carbamic acid tert.-butyl ester analogously to the preparation of "A62"; method 1: HPLC/MS: 1.34 min, [M+H]=406.

13.2 2-Amino-5-(2-amino-phenyl)-N-pyridin-4-yl-nicotinamide 100 mg of {2-[6-Amino-5-(pyridin-4-ylcarbamoyl)-pyridin-3-yl]-phenyl}-carbamic acid tert.-butyl ester are dissolved in 2 ml dichloromethane. 0.5 ml of HCl in dioxane (4 molar) are added. The mixture is stirred 2 h at room temperature. The mixture is filtered and the solid washed with dichloromethane. 80 mg of "A103", hydrochloride salt, are obtained; method 1: HPLC/MS: 1.17 min, [M+H]=306;

¹H NMR (500 MHz, DMSO-d₆/TFA-d₁) δ [ppm] 8.99 (1 H, d, J 2.2), 8.85 (2 H, d, J 7.3), 8.49 (1 H, d, J 2.1), 8.43 (2 H, d, J 7.5), 7.68-7.55 (4 H, m).

Using the above mentioned procedure the following compounds are obtained analogously:

2-Amino-5-(3-amino-phenyl)-N-pyridin-4-yl-nicotinamide ("A104")

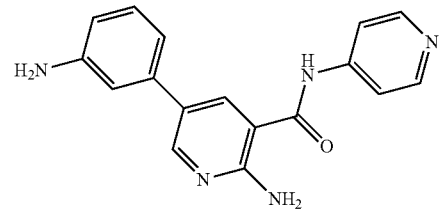 [SMILES: Nc1cccc(-c2cnc(N)c(C(=O)Nc3ccncc3)c2)c1]

Solvolysis of {3-[6-amino-5-(pyridin-4-ylcarbamoyl)-pyridin-3-yl]-phenyl}-carbamic acid tert.-butyl ester gives "A104"; method 1: HPLC/MS: 0.99 min, [M+H]=306;

¹H NMR (500 MHz, DMSO-d₆/TFA-d₁) δ [ppm] 9.02 (1 H, d, J 2.2), 8.86 (2 H, d, J 7.3), 8.69 (1 H, d, J 2.2), 8.37 (2 H, d, J 7.3), 7.94 (1 H, d, J 8.1), 7.86 (1 H, t, J 1.8), 7.70 (1 H, t, J 7.9), 7.54 (1 H, dd, J 8.0, 1.2);

2-Amino-5-[4-(2-amino-ethylcarbamoyl)-phenyl]-N-pyridin-4-yl-nicotinamide ("A105")

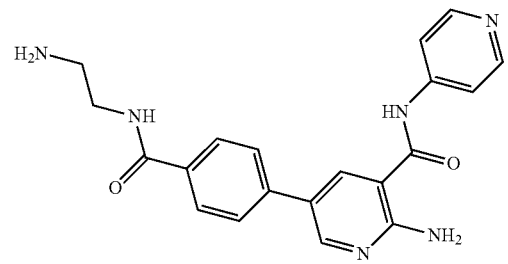 [SMILES: NCCNC(=O)c1ccc(-c2cnc(N)c(C(=O)Nc3ccncc3)c2)cc1]

Solvolysis of (2-{4-[6-Amino-5-(pyridin-4-ylcarbamoyl)-pyridin-3-yl]-benzoylamino}-ethyl)-carbamic acid tert.-butyl ester gives "A105"; method 2: HPLC/MS: 1.57 min, [M+H]=377;

¹H NMR (500 MHz, DMSO-d₆/TFA-d₁) δ [ppm] 9.18 (1 H, d, J 2.2), 8.77 (2 H, d, J 7.3), 8.72 (1 H, d, J 2.2), 8.42 (2 H, d, J 7.3), 8.13 (2 H, d, J 8.4), 7.96 (2 H, d, J 8.5), 3.67 (2 H, t, J 10.6, 4.6), 3.14 (2 H, t, J 5.8).

EXAMPLE 14

2-Amino-N-pyridin-4-yl-5-(2-sulfamoyl-phenyl)-nicotinamide ("A106")

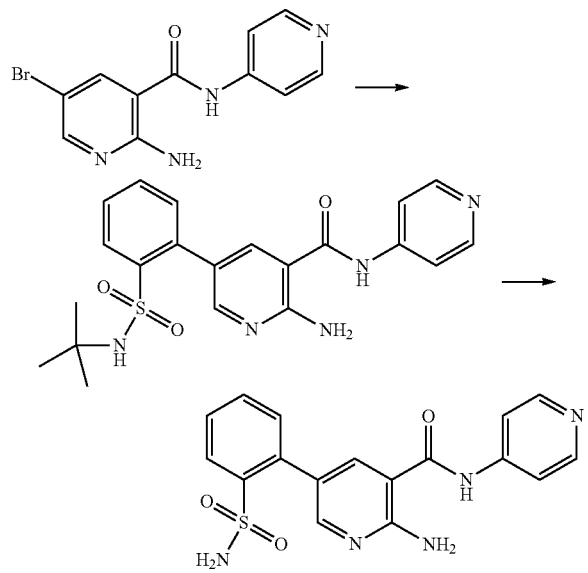

14.1 2-Amino-5-(2-tert.-butylsulfamoyl-phenyl)-N-pyridin-4-yl-nicotin-amide

The compound is obtained by reaction of 2-amino-5-bromo-N-(2-ethoxy-pyridin-4-yl)-nicotinamide with 2-tert.-butylsulfamoyl-benzeneboronic acid analogously to step 1 for "A62"; method 1: HPLC/MS: 1.41 min, [M+H]=426;

¹H NMR (400 MHz, DMSO-d₆/TFA-d₁) δ [ppm] 8.86-8.80 (3 H, m), 8.39 (1 H, d, J 2.1), 8.28 (2 H, d, J 7.3), 8.15 (1 H, dd, J 7.9, 1.2), 7.73 (2 H, dtd, J 31.4, 7.6, 1.4), 7.57 (1 H, dd, J 7.6, 1.2), 1.09 (9 H, s).

14.2 2-Amino-N-pyridin-4-yl-5-(2-sulfamoyl-phenyl)-nicotinamide ("A106")

20 mg 2-Amino-5-(2-tert.-butylsulfamoyl-phenyl)-N-pyridin-4-yl-nicotinamide is dissolved in 0.5 ml of trifluoroacetic acid. The mixture is stirred at 80° C. for 14 h. The reaction mixture is cooled to room temperature, 2 ml heptan is added and the solvent is removed in vacuo, the residue is dissolved in methylene chloride and the resulting precipitate is filtered off, to give 17 mg "A106" as trifluoro-acetate salt; method 1: HPLC/MS: 1.07 min, [M+H]=370;

¹H NMR (400 MHz, DMSO-d₆/TFA-d₁) δ [ppm] 8.86 (1 H, d, J 2.2), 8.82 (2 H, d, J 7.3), 8.42 (1 H, d, J 2.2), 8.33 (2 H, d, J 7.5), 8.18 (1 H, dd, J 7.8, 1.4), 7.73 (2H, dtd, J 22.4, 7.6, 1.4), 7.58 (1 H, dd, J 7.4, 1.4).

EXAMPLE 15

2-Amino-5-[4-(tert-butylamino-methyl)-phenyl]-N-pyridin-4-yl-nicotinamide ("A107")

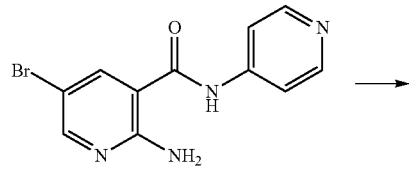

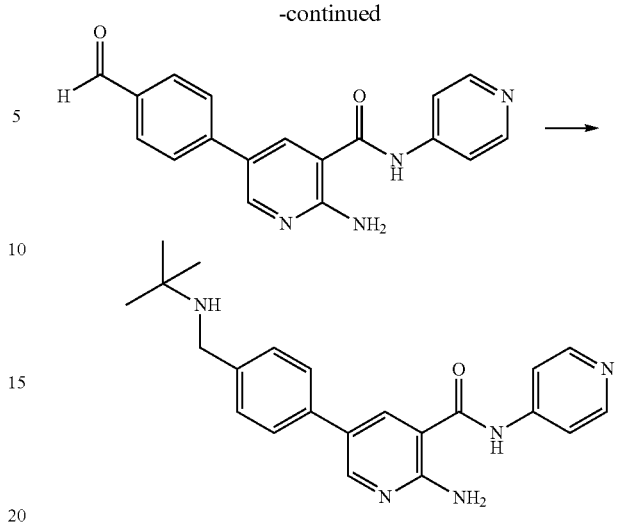

15.1 2-Amino-5-(4-formyl-phenyl)-N-pyridin-4-yl-nicotinamide

The title compound is obtained by reaction of 2-amino-5-bromo-N-(2-ethoxy-pyridin-4-yl)-nicotinamide with 4-formylbenzeneboronic acid analogously to step 1 for "A62"; method 1: HPLC/MS: 1.29 min, [M+H]=319;

¹H NMR (500 MHz, DMSO-d₆/TFA-d₁) δ [ppm] 10.10 (1 H, s), 9.08 (1 H, d, J 2.2), 8.86 (2 H, d, J 7.2), 8.82 (1 H, d, J 2.2), 8.32 (2 H, d, J 7.3), 8.12-8.05 (4 H, m).

15.2 2-Amino-5-[4-(tert-butylamino-methyl)-phenyl]-N-pyridin-4-yl-nicotinamide ("A107")

70 mg NaB(OAc)₃H is added to a mixture of 50 mg 2-amino-5-(4-formyl-phenyl)-N-pyridin-4-yl-nicotinamide, 20.6 µl tert.-butylamine and 9 µl acetic acid in 0.5 ml 1,2-dichloroethane and 0.5 ml tetrahydrofuran. The resulting suspension is stirred at 50° C. for 14 h. The reaction mixture is made basic with a 2N NaOH solution and extracted with dichloromethane. The organic layer is washed with brine, then separated and dried over Na₂SO₄. The drying agent is filtered and the solvent is removed in vacuo. The product is purified by chromatography to yield 10 mg "A107" as a white solid; method 1: HPLC/MS: 1.10 min, [M+H]=376;

¹H NMR (400 MHz, DMSO-d₆/TFA-d₁) δ [ppm] 9.05 (1 H, d, J 2.2), 8.84 (2 H, d, J 7.3), 8.75 (1 H, d, J 2.2), 8.34 (2 H, d, J 7.3), 7.94 (2 H, d, J 8.4), 7.73 (2 H, d, J 8.4), 4.20 (2 H, s), 1.44 (9 H, s).

EXAMPLE 16

2-Amino-5-(2-ethylsulfamoyl-phenyl)-N-pyridin-4-yl-nicotinamide ("A108")

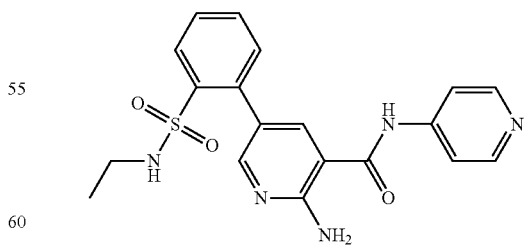

Under argon atmosphere, a reaction vessel is charged with 100 mg 2-amino-5-bromo-N-pyridin-4-yl-nicotinamide, 86 mg bis(pinacolate)diboron, 5 ml degassed N,N-dimethyl-formamide and 134 mg potassium acetate and stirred at room temperature. The reaction vessel is charged with 27 mg (1,1'-bis(diphenyl-phosphino)-ferrocen)dichloropalladium(II)

and stirred at 80° C. for 14 h. 108 mg 2-Bromo-N-ethyl-benzenesulfonamide, 27 mg (1,1'-bis(diphenylphosphino)-ferrocen)dichloro-palladium(II) and 200 μl water are added to the solution. The reaction mixture stirred at 100° C. for 14 h, cooled to room temperature and evaporated. The product is purified by chromatography. 8 mg "A108" are obtained; method 1: HPLC/MS: 1.32 min, [M+H]=398;

$^1$H NMR (500 MHz, DMSO-d$_6$/TFA-d$_1$) δ [ppm] 8.95 (1 H, d, J 2.0), 8.73 (2 H, d, J 7.3), 8.38 (1 H, d, J 2.1), 8.36 (2 H, d, J 7.3), 8.14 (1 H, d, J 7.9), 7.76 (1 H, t, J 7.5), 7.70 (1 H, t, J 7.7), 7.57 (1 H, d, J 7.5), 2.85 (2 H, q, J 7.2), 1.01 (3 H, t, J 7.2).

IC$_{50}$ values of compounds according to the invention inhibiting TBK1 and IKKε

| Compound No. | TBK1 enzyme assay IC$_{50}$ [nM] | IKKε enzyme assay IC$_{50}$ [nM] | TBK1 cell assay IC$_{50}$ [nM] |
|---|---|---|---|
| "A1" | 390 | 120 | 1100 |
| "A2" | 130 | 110 | |
| "A3" | 120 | 150 | |
| "A4" | 400 | | 4500 |
| "A5" | 120 | | 10000 |
| "A6" | 67 | 1900 | 7800 |
| "A7" | 150 | 1800 | |
| "A8" | 78 | 830 | 3100 |
| "A9" | 430 | 660 | 3000 |
| "A10" | 1000 | | |
| "A11" | 770 | 540 | 9800 |
| "A12" | 8300 | 1000 | |
| "A13" | 4000 | 1900 | |
| "A14" | 4200 | 1900 | |
| "A15" | 670 | 2000 | |
| "A16" | 240 | 110 | 9300 |
| "A17" | 330 | 340 | 8100 |
| "A18" | 790 | 640 | |
| "A19" | 1000 | 2800 | |
| "A20" | 1200 | 610 | |
| "A21" | 260 | 910 | 7000 |
| "A22" | 690 | 2400 | |
| "A23" | 7400 | 2200 | |
| "A24" | 1200 | 890 | |
| "A25" | 360 | 530 | |
| "A26" | 8200 | 5200 | |
| "A27" | 810 | 2600 | |
| "A28" | 1200 | 2900 | |
| "A29" | 890 | 2400 | |
| "A30" | 1600 | 1900 | |
| "A31" | 400 | 990 | |
| "A32" | 250 | 600 | |
| "A33" | 250 | 600 | |
| "A34" | 280 | 740 | |
| "A35" | 450 | | |
| "A36" | 190 | 540 | |
| "A37" | 1100 | 3200 | |
| "A38" | 740 | 1500 | |
| "A39" | 910 | 390 | |
| "A40" | | | |
| "A41" | | | |
| "A42" | 670 | 1700 | |
| "A43" | 140 | 330 | |
| "A44" | 240 | 420 | |
| "A45" | 610 | 140 | |
| "A46" | 120 | 240 | |
| "A47" | 330 | 380 | |
| "A48" | | | |
| "A49" | 410 | 930 | |
| "A50" | 320 | | |
| "A51" | 740 | 270 | |
| "A52" | 630 | | |
| "A53" | 160 | 510 | |
| "A54" | 88 | 450 | |
| "A55" | 390 | | |
| "A56" | 510 | 340 | |
| "A57" | 410 | 3300 | |
| "A58" | 370 | 1800 | |
| "A59" | 150 | 830 | |
| "A60" | 230 | 300 | |
| "A61" | 160 | 480 | |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. Compounds of the formula I

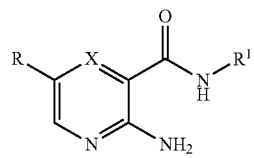

in which:

X denotes CH,

R denotes Ar or Het,

R$^1$ denotes furyl, thienyl, pyrrolyl, imidazolyl, pyrazolyl, oxazolyl, isoxazolyl, thiazolyl, para-pyridyl, pyrimidyl, pyridazinyl, indolyl, isoindolyl, benzimid-azolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by Hal, A, OR$^5$, CN, COOA, COOH, CON(R$^5$)$_2$ and/or NR$^5$COA', Ar denotes phenyl, biphenyl or naphtyl, each of which is unsubstituted or mono-, di- or trisubstituted by Hal, A, Het$^1$, (CH$_2$)$_n$OR$^5$, (CH$_2$)$_n$N(R$^5$)$_2$, NO$_2$, CN, (CH$_2$)$_n$COOR$^5$, CON(R$^5$)$_2$, CONH(CH$_2$)$_q$NHCOOA', CON[R$^5$(CH$_2$)$_n$Het$^1$], NR$^5$COA, NHCOOA, NR$^5$SO$_2$A, COR$^5$, SO$_2$Het$^2$, SO$_2$N(R$^5$)$_2$ and/or S(O)$_p$A, Het denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl, 1,3-benzo-dioxolyl, benzothiophenyl, benzofuranyl or imidazopyridyl, each of which is unsubstituted or mono-, di- or trisubstituted by A, COA, (CH$_2$)$_p$Het$^2$, OH, OA, Hal, (CH$_2$)$_p$N(R$^5$)$_2$, NO$_2$, CN, (CH$_2$)$_p$COOR$^5$, (CH$_2$)$_p$CON(R$^5$)$_2$, NR$^5$COA, (CH$_2$)$_p$COHet$^2$ and/or (CH$_2$)$_p$phenyl, Het$^1$ denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, each of which is unsubstituted or mono-, di- or trisubstituted by A, OH, OA, Hal, CN and/or (CH$_2$)$_p$COOR$^5$, Het$^2$ denotes dihydropyrrolyl, pyrrolidinyl, tetrahydroimidazolyl, dihydropyrazolyl, tetrahydropyrazolyl, dihydropyridyl, tetrahydropyridyl, piperidinyl, morpholinyl, hexahydropyridazinyl, hexahydropyrimidinyl, [1,3]dioxolanyl, piperazinyl, each of which is unsubstituted or monosubstituted by OH and/or A, A' denotes unbranched or branched alkyl having 1-6 C atoms, in which 1-7 H atoms may be replaced by F, A denotes unbranched or branched alkyl having 1-10 C atoms, in which one or two non-adjacent CH and/or $CH_2$ groups may be replaced by N, O, S atoms and/or by —CH=CH— groups and/or in addition 1-7 H atoms may be replaced by F, $R^5$ denotes H or unbranched or branched alkyl having 1-6 C atoms, in which 1-7 H atoms may be replaced by F, Hal denotes F, Cl, Br or I, n denotes 0, 1, 2, 3 or 4, p denotes 0, 1 or 2, q denotes 1, 2, 3 or 4, and pharmaceutically usable salts, tautomers and stereoisomers thereof, including mixtures thereof in all ratios.

2. Compounds according to claim 1, in which:

$R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$, and pharmaceutically usable salts, tautomers and stereoisomers thereof, including mixtures thereof in all ratios.

3. Compounds according to claim 1, in which:

Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$, and pharmaceutically usable salts, tautomers and stereoisomers thereof, including mixtures thereof in all ratios.

4. Compounds according to claim 2, in which:

Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$, and pharmaceutically usable salts, tautomers and stereoisomers thereof, including mixtures thereof in all ratios.

5. Compounds according to claim 1, in which:

Het denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl, and pharmaceutically usable salts, tautomers and stereoisomers thereof, including mixtures thereof in all ratios.

6. Compounds according to claim 2, in which:

Het denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl, and pharmaceutically usable salts, tautomers and stereoisomers thereof, including mixtures thereof in all ratios.

7. Compounds according to claim 3, in which:

Het denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl, and pharmaceutically usable salts, tautomers and stereoisomers thereof, including mixtures thereof in all ratios.

8. Compounds according to claim 1, in which:

$Het^1$ denotes pyrazolyl or imidazolyl, each of which is unsubstituted or monosubstituted by A, and pharmaceutically usable salts, tautomers and stereoisomers thereof, including mixtures thereof in all ratios.

9. Compounds according to claim 2, in which:

$Het^1$ denotes pyrazolyl or imidazolyl, each of which is unsubstituted or monosubstituted by A, and pharmaceutically usable salts, tautomers and stereoisomers thereof, including mixtures thereof in all ratios.

10. Compounds according to claim 3, in which:

$Het^1$ denotes pyrazolyl or imidazolyl, each of which is unsubstituted or monosubstituted by A, and pharmaceutically usable salts, tautomers and stereoisomers thereof, including mixtures thereof in all ratios.

11. Compounds according to claim 4, in which:

$Het^1$ denotes pyrazolyl or imidazolyl, each of which is unsubstituted or monosubstituted by A, and pharmaceutically usable salts, tautomers and stereoisomers thereof, including mixtures thereof in all ratios.

12. Compounds according to claim 1, in which:

$Het^2$ denotes pyrrolidinyl, piperidinyl, morpholinyl, [1,3]dioxolanyl, piperazinyl, each of which is unsubstituted or monosubstituted by OH and/or A, and pharmaceutically usable salts, tautomers and stereoisomers thereof, including mixtures thereof in all ratios.

13. Compounds according to claim 2, in which:

$Het^2$ denotes pyrrolidinyl, piperidinyl, morpholinyl, [1,3]dioxolanyl, piperazinyl, each of which is unsubstituted or monosubstituted by OH and/or A, and pharmaceutically usable salts, tautomers and stereoisomers thereof, including mixtures thereof in all ratios.

14. Compounds according to claim 3, in which:

$Het^2$ denotes pyrrolidinyl, piperidinyl, morpholinyl, [1,3]dioxolanyl, piperazinyl, each of which is unsubstituted or monosubstituted by OH and/or A, and pharmaceutically usable salts, tautomers and stereoisomers thereof, including mixtures thereof in all ratios.

15. Compounds according to claim 4, in which:

$Het^2$ denotes pyrrolidinyl, piperidinyl, morpholinyl, [1,3]dioxolanyl, piperazinyl, each of which is unsubstituted or monosubstituted by OH and/or A, and pharmaceutically usable salts, tautomers and stereoisomers thereof, including mixtures thereof in all ratios.

16. Compounds according to claim 5, in which:

$Het^2$ denotes pyrrolidinyl, piperidinyl, morpholinyl, [1,3]dioxolanyl, piperazinyl, each of which is unsubstituted or monosubstituted by OH and/or A, and pharmaceutically usable salts, tautomers and stereoisomers thereof, including mixtures thereof in all ratios.

17. Compounds according to claim 1, in which:

A denotes unbranched or branched alkyl having 1-6 C atoms, in which one or two non-adjacent CH and/or $CH_2$ groups may be replaced by N and/or O atoms and/or in addition 1-7 H atoms may be replaced by F, and pharmaceutically usable salts, tautomers and stereoisomers thereof, including mixtures thereof in all ratios.

18. Compounds according to claim 2, in which:

A denotes unbranched or branched alkyl having 1-6 C atoms, in which one or two non-adjacent CH and/or CH2 groups may be replaced by N and/or O atoms and/or in addition 1-7 H atoms may be replaced by F, and pharmaceutically usable salts, tautomers and stereoisomers thereof, including mixtures thereof in all ratios.

19. Compounds according to claim 3, in which:

A denotes unbranched or branched alkyl having 1-6 C atoms, in which one or two non-adjacent CH and/or $CH_2$ groups may be replaced by N and/or O atoms and/or in addition 1-7 H atoms may be replaced by F, and pharmaceutically usable salts, tautomers and stereoisomers thereof, including mixtures thereof in all ratios.

20. Compounds according to claim 4, in which:

A denotes unbranched or branched alkyl having 1-6 C atoms, in which one or two non-adjacent CH and/or $CH_2$ groups may be replaced by N and/or O atoms and/or in addition 1-7 H atoms may be replaced by F, and pharmaceutically usable salts, tautomers and stereoisomers thereof, including mixtures thereof in all ratios.

21. Compounds according to claim 5, in which:
A denotes unbranched or branched alkyl having 1-6 C atoms, in which one or two non-adjacent CH and/or $CH_2$ groups may be replaced by N and/or O atoms and/or in addition 1-7 H atoms may be replaced by F,
and pharmaceutically usable salts, tautomers and stereoisomers thereof, including mixtures thereof in all ratios.

22. Compounds according to claim 6, in which:
A denotes unbranched or branched alkyl having 1-6 C atoms, in which one or two non-adjacent CH and/or $CH_2$ groups may be replaced by N and/or O atoms and/or in addition 1-7 H atoms may be replaced by F,
and pharmaceutically usable salts, tautomers and stereoisomers thereof, including mixtures thereof in all ratios.

23. Compounds according to claim 1, in which:
X denotes CH,
R denotes Ar or Het,
$R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$,
Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$,
Het denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl,
$Het^1$ denotes pyrazolyl or imidazolyl, each of which is unsubstituted or monosubstituted by A,
$Het^2$ denotes pyrrolidinyl, piperidinyl, morpholinyl, [1,3]dioxolanyl, piperazinyl, each of which is unsubstituted or monosubstituted by OH and/or A,
A' denotes unbranched or branched alkyl having 1-6 C atoms, in which 1-7 H atoms may be replaced by F,
A denotes unbranched or branched alkyl having 1-6 C atoms, in which one or two non-adjacent CH and/or $CH_2$ groups may be replaced by N and/or O atoms and/or in addition 1-7 H atoms may be replaced by F,
$R^5$ denotes H or unbranched or branched alkyl having 1-6 C atoms, in which 1-7 H atoms may be replaced by F,
Hal denotes F, Cl, Br or I,
n denotes 0, 1, 2, 3 or 4,
p denotes 0, 1 or 2,
q denotes 1, 2, 3 or 4,
and pharmaceutically usable salts, tautomers and stereoisomers thereof, including mixtures thereof in all ratios.

24. Compounds according to claim 2, in which:
X denotes CH,
R denotes Ar or Het,
$R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$,
Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$,
Het denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl,
$Het^1$ denotes pyrazolyl or imidazolyl, each of which is unsubstituted or monosubstituted by A,
$Het^2$ denotes pyrrolidinyl, piperidinyl, morpholinyl, [1,3]dioxolanyl, piperazinyl, each of which is unsubstituted or monosubstituted by OH and/or A,
A' denotes unbranched or branched alkyl having 1-6 C atoms, in which 1-7 H atoms may be replaced by F,
A denotes unbranched or branched alkyl having 1-6 C atoms, in which one or two non-adjacent CH and/or $CH_2$ groups may be replaced by N and/or O atoms and/or in addition 1-7 H atoms may be replaced by F,
$R^5$ denotes H or unbranched or branched alkyl having 1-6 C atoms, in which 1-7 H atoms may be replaced by F,
Hal denotes F, Cl, Br or I,
n denotes 0, 1, 2, 3 or 4,
p denotes 0, 1 or 2,
q denotes 1, 2, 3 or 4,
and pharmaceutically usable salts, tautomers and stereoisomers thereof, including mixtures thereof in all ratios.

25. Compounds according to claim 3, in which:
X denotes CH,
R denotes Ar or Het,
$R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$,
Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$,
Het denotes thienyl, pyrazolyl, pyridyl, each of which is unsubstituted or mono- or disubstituted by A, $(CH_2)_pHet^2$, $(CH_2)_pCON(R^5)_2$ and/or $(CH_2)_p$phenyl,
$Het^1$ denotes pyrazolyl or imidazolyl, each of which is unsubstituted or monosubstituted by A,
$Het^2$ denotes pyrrolidinyl, piperidinyl, morpholinyl, [1,3]dioxolanyl, piperazinyl, each of which is unsubstituted or monosubstituted by OH and/or A,
A' denotes unbranched or branched alkyl having 1-6 C atoms, in which 1-7 H atoms may be replaced by F,
A denotes unbranched or branched alkyl having 1-6 C atoms, in which one or two non-adjacent CH and/or $CH_2$ groups may be replaced by N and/or O atoms and/or in addition 1-7 H atoms may be replaced by F,
$R^5$ denotes H or unbranched or branched alkyl having 1-6 C atoms, in which 1-7 H atoms may be replaced by F,
Hal denotes F, Cl, Br or I,
n denotes 0, 1, 2, 3 or 4,
p denotes 0, 1 or 2,
q denotes 1, 2, 3 or 4,
and pharmaceutically usable salts, tautomers and stereoisomers thereof, including mixtures thereof in all ratios.

26. Compounds according to claim 4, in which:
X denotes CH,
R denotes Ar or Het,
$R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$,
Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_qNHCOOA'$, $CON[R^5(CH_2)_nHet^1]$, NHCOOA, $(CH_2)_nN(R^5)_2$, $(CH_2)_nOR^5$, $(CH_2)_nCOOR^5$, $SO_2Het^2$ and/or $SO_2N(R^5)_2$, Het denotes thienyl, pyrazolyl, pyridyl, each of which is unsubstituted or mono- or disubstituted by A, $(CH_2)_p$ $Het^2$, $(CH_2)_p CON(R^5)_2$ and/or $(CH_2)_p$phenyl, $Het^1$ denotes pyrazolyl or imidazolyl, each of which is unsubstituted or monosubstituted by A, $Het^2$ denotes pyrrolidinyl, piperidinyl, morpholinyl, [1,3]dioxolanyl, piperazinyl, each of which is unsubstituted or monosubstituted by OH and/or A, A' denotes unbranched or branched alkyl having 1-6 C atoms, in which 1-7 H atoms may be replaced by F, A denotes unbranched or branched alkyl having 1-6 C atoms, in which one or two non-adjacent CH and/or $CH_2$ groups may be replaced by N and/or O atoms and/or in addition 1-7 H atoms may be replaced by F, $R^5$ denotes H or unbranched or branched alkyl having 1-6 C atoms, in which 1-7 H atoms may be replaced by F, Hal denotes F, Cl, Br or I, n denotes 0, 1, 2, 3 or 4, p denotes 0, 1 or 2, q denotes 1, 2, 3 or 4, and pharmaceutically usable salts, tautomers and stereoisomers thereof, including mixtures thereof in all ratios.

27. Compounds according to claim 5, in which:

X denotes CH,

R denotes Ar or Het, $R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$, Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_q NHCOOA'$, $CON[R^5(CH_2)_n Het^1]$, NHCOOA, $(CH_2)_n N(R^5)_2$, $(CH_2)_n OR^5$, $(CH_2)_n COOR^5$, $SO_2Het^2$ and/or $SO_2N(R^5)_2$, Het denotes thienyl, pyrazolyl, pyridyl, each of which is unsubstituted or mono- or disubstituted by A, $(CH_2)_p$ $Het^2$, $(CH_2)_p CON(R^5)_2$ and/or $(CH_2)_p$phenyl, $Het^1$ denotes pyrazolyl or imidazolyl, each of which is unsubstituted or monosubstituted by A, $Het^2$ denotes pyrrolidinyl, piperidinyl, morpholinyl, [1,3]dioxolanyl, piperazinyl, each of which is unsubstituted or monosubstituted by OH and/or A, A' denotes unbranched or branched alkyl having 1-6 C atoms, in which 1-7 H atoms may be replaced by F, A denotes unbranched or branched alkyl having 1-6 C atoms, in which one or two non-adjacent CH and/or $CH_2$ groups may be replaced by N and/or O atoms and/or in addition 1-7 H atoms may be replaced by F, $R^5$ denotes H or unbranched or branched alkyl having 1-6 C atoms, in which 1-7 H atoms may be replaced by F, Hal denotes F, Cl, Br or I, n denotes 0, 1, 2, 3 or 4, p denotes 0, 1 or 2, q denotes 1, 2, 3 or 4, and pharmaceutically usable salts, tautomers and stereoisomers thereof, including mixtures thereof in all ratios.

28. Compounds according to claim 6, in which:

X denotes CH,

R denotes Ar or Het, $R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$, Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_q NHCOOA'$, $CON[R^5(CH_2)_n Het^1]$, NHCOOA, $(CH_2)_n N(R^5)_2$, $(CH_2)_n OR^5$, $(CH_2)_n COOR^5$, $SO_2Het^2$ and/or $SO_2N(R^5)_2$, Het denotes thienyl, pyrazolyl, pyridyl, each of which is unsubstituted or mono- or disubstituted by A, $(CH_2)_p$ $Het^2$, $(CH_2)_p CON(R^5)_2$ and/or $(CH_2)_p$phenyl, $Het^1$ denotes pyrazolyl or imidazolyl, each of which is unsubstituted or monosubstituted by A, $Het^2$ denotes pyrrolidinyl, piperidinyl, morpholinyl, [1,3]dioxolanyl, piperazinyl, each of which is unsubstituted or monosubstituted by OH and/or A, A' denotes unbranched or branched alkyl having 1-6 C atoms, in which 1-7 H atoms may be replaced by F, A denotes unbranched or branched alkyl having 1-6 C atoms, in which one or two non-adjacent CH and/or $CH_2$ groups may be replaced by N and/or O atoms and/or in addition 1-7 H atoms may be replaced by F, $R^5$ denotes H or unbranched or branched alkyl having 1-6 C atoms, in which 1-7 H atoms may be replaced by F, Hal denotes F, Cl, Br or I, n denotes 0, 1, 2, 3 or 4, p denotes 0, 1 or 2, q denotes 1, 2, 3 or 4, and pharmaceutically usable salts, tautomers and stereoisomers thereof, including mixtures thereof in all ratios.

29. Compounds according to claim 7, in which:

X denotes CH,

R denotes Ar or Het, $R^1$ denotes para-pyridyl, pyrimidyl, pyridazinyl or furo[3,2-b]pyridyl, each of which is unsubstituted or monosubstituted by Hal, A, $OR^5$, COOA, COOH, $CON(R^5)_2$ and/or $NR^5COA'$, Ar denotes phenyl, biphenyl or naphtyl, each of which is unsubstituted or mono-, di- or trisubstituted by A, Hal, $Het^1$, $COR^5$, $CON(R^5)_2$, $CONH(CH_2)_q NHCOOA'$, $CON[R^5(CH_2)_n Het^1]$, NHCOOA, $(CH_2)_n N(R^5)_2$, $(CH_2)_n OR^5$, $(CH_2)_n COOR^5$, $SO_2Het^2$ and/or $SO_2N(R^5)_2$, Het denotes thienyl, pyrazolyl, pyridyl, each of which is unsubstituted or mono- or disubstituted by A, $(CH_2)_p$ $Het^2$, $(CH_2)_p CON(R^5)_2$ and/or $(CH_2)_p$phenyl, $Het^1$ denotes pyrazolyl or imidazolyl, each of which is unsubstituted or monosubstituted by A, $Het^2$ denotes pyrrolidinyl, piperidinyl, morpholinyl, [1,3]dioxolanyl, piperazinyl, each of which is unsubstituted or monosubstituted by OH and/or A, A' denotes unbranched or branched alkyl having 1-6 C atoms, in which 1-7 H atoms may be replaced by F, A denotes unbranched or branched alkyl having 1-6 C atoms, in which one or two non-adjacent CH and/or $CH_2$ groups may be replaced by N and/or O atoms and/or in addition 1-7 H atoms may be replaced by F, $R^5$ denotes H or unbranched or branched alkyl having 1-6 C atoms, in which 1-7 H atoms may be replaced by F, Hal denotes F, Cl, Br or I, n denotes 0, 1, 2, 3 or 4, p denotes 0, 1 or 2, q denotes 1, 2, 3 or 4, and pharmaceutically usable salts, tautomers and stereoisomers thereof, including mixtures thereof in all ratios.

30. Compounds according to claim 1, selected from the group consisting of:

| compound nr. | name |
|---|---|
| "A1" | 2-Amino-5-(5-piperidin-1-ylmethyl-thiophen-2-yl)-N-pyridin-4-yl-nicotinamide |
| "A2" | 2-Amino-N-pyridin-4-yl-5-(5-pyrrolidin-1-ylmethyl-thiophen-2-yl)-nicotinamide |
| "A3" | 2-Amino-5-(5-methyl-thiophen-2-yl)-N-pyridin-4-yl-nicotinamide |
| "A4" | 2-Amino-5-(3-pyrazol-1-yl-phenyl)-N-pyridin-4-yl-nicotinamide |
| "A5" | 2-Amino-5-(4-pyrazol-1-yl-phenyl)-N-pyridin-4-yl-nicotinamide |
| "A6" | 2-Amino-5-[1-(2-methoxy-ethyl)-1H-pyrazol-4-yl]-N-pyridin-4-yl-nicotinamide |
| "A7" | 2-Amino-N-pyridin-4-yl-5-(4-sulfamoyl-phenyl)-nicotinamide |
| "A8" | 2-Amino-N-(2-methyl-pyridin-4-yl)-5-(5-morpholin-4-ylmethyl-thiophen-2-yl)-nicotinamide |
| "A9" | 2-Amino-N-(2-ethoxy-pyridin-4-yl)-5-(5-morpholin-4-ylmethyl-thiophen-2-yl)-nicotinamide |
| "A11" | 6-Amino-6'-piperazin-1-yl-[3,3']bipyridinyl-5-carboxylic acid pyridin-4-ylamide |
| "A15" | 2-Amino-N-(2-methyl-pyridin-4-yl)-5-(5-morpholin-4-ylmethyl-thiophen-3-yl)-nicotinamide |
| "A16" | 2-Amino-5-(5-morpholin-4-ylmethyl-thiophen-2-yl)-N-pyridazin-4-yl-nicotinamide |
| "A17" | 2-Amino-5-(1-benzyl-1H-pyrazol-4-yl)-N-(2-methyl-pyridin-4-yl)-nicotinamide |
| "A18" | 2-Amino-5-(3-pyrazol-1-yl-phenyl)-N-pyridazin-4-yl-nicotinamide |
| "A19" | 2-Amino-N-(3-methyl-pyridin-4-yl)-5-(4-pyrazol-1-yl-phenyl)-nicotinamide |
| "A20" | 2-Amino-5-[1-(2-methoxy-ethyl)-1H-pyrazol-4-yl]-N-(2-methyl-pyridine-4-yl)-nicotinamide |
| "A21" | 2-Amino-N-(3-methyl-pyridin-4-yl)-5-(5-morpholin-4-ylmethyl-thiophen-2-yl)-nicotinamide |
| "A22" | 2-Amino-5-[1-(2-methoxy-ethyl)-1H-pyrazol-4-yl]-N-(3-methyl-pyridin-4-yl)-nicotinamide |
| "A23" | 2-Amino-5-(4'-methyl-biphenyl-3-yl)-N-pyridin-4-yl-nicotinamide |
| "A24" | 2-Amino-5-[1-(2-methoxy-ethyl)-1H-pyrazol-4-yl]-N-pyridazin-4-yl-nicotinamide |
| "A25" | 2-Amino-5-(1-carbamoylmethyl-1H-pyrazol-4-yl)-N-pyridin-4-yl-nicotinamide |
| "A26" | 2-Amino-N-(2,6-dimethyl-pyridin-4-yl)-5-(5-morpholin-4-ylmethyl-thiophen-2-yl)-nicotinamide |
| "A27" | 2-Amino-5-(5-morpholin-4-ylmethyl-thiophen-2-yl)-N-pyrimidin-4-yl-nicotinamide |
| "A28" | 2-Amino-N-furo[3,2-b]pyridin-7-yl-5-[1-(2-methoxy-ethyl)-1H-pyrazol-4-yl]-nicotinamide |
| "A29" | 2-Amino-N-furo[3,2-b]pyridin-7-yl-5-(5-morpholin-4-ylmethyl-thiophen-2-yl)-nicotinamide |
| "A30" | 4-[6-Amino-5-(pyridin-4-ylcarbamoyl)-pyridin-3-yl]-benzoic acid methyl ester |
| "A31" | 4-[6-Amino-5-(pyridin-4-ylcarbamoyl)-pyridin-3-yl]-benzoic acid |
| "A32" | 3-{4-[6-Amino-5-(pyridin-4-ylcarbamoyl)-pyridin-3-yl]-phenyl}-propionic acid |
| "A33" | 2-Amino-N-(3-chloro-pyridin-4-yl)-5-(5-morpholin-4-ylmethyl-thiophen-2-yl)-nicotinamide |
| "A34" | 2-Amino-5-(1H-pyrazol-4-yl)-N-pyridin-4-yl-nicotinamide |
| "A35" | 4-{[2-Amino-5-(5-morpholin-4-ylmethyl-thiophen-2-yl)-pyridine-3-carbonyl]-amino}-nicotinic acid methyl ester |
| "A36" | N-(2-Acetylamino-pyridin-4-yl)-2-amino-5-(5-morpholin-4-ylmethyl-thiophen-2-yl)-nicotinamide |
| "A37" | 3-[6-Amino-5-(pyridin-4-ylcarbamoyl)-pyridin-2-yl]-benzoic acid |
| "A38" | 2-Amino-N-(3-chloro-pyridin-4-yl)-5-[1-(2-methoxy-ethyl-)-1H-pyrazol-4-yl]nicotinamide |
| "A39" | 2-Amino-N-(4-methoxy-phenyl)-5-(5-morpholin-4-ylmethyl-thiophen-2-yl)-nicotinamide |
| "A40" | 2-Amino-N-(6-methoxy-pyridin-3-yl)-5-(5-morpholin-4-ylmethyl-thiophen-2-yl)-nicotinamide |
| "A41" | 2-Amino-N-(3-methylcarbamoyl-pyridin-4-yl)-5-(5-morpholin-4-yl-methyl-thiophen-2-yl)-nicotinamide |
| "A42" | 2-Amino-5-[1-(2-hydroxy-ethyl)-1H-pyrazol-4-yl]-N-pyridin-4-yl-nicotinamide |
| "A43" | 2-Amino-5-(5-morpholin-4-ylmethyl-thiophen-3-yl)-N-pyridin-4-yl-nicotinamide |
| "A44" | 5-(4-Acetyl-1H-pyrrol-2-yl)-2-amino-N-pyridin-4-yl-nicotinamide |
| "A45" | 2-Amino-5-furan-3-yl-N-pyridin-4-yl-nicotinamide |
| "A46" | 2-Amino-5-(1-benzyl-1H-pyrazol-4-yl)-N-pyridin-4-yl-nicotinamide |
| "A47" | 2-Amino-5-(1-methyl-1H-pyrazol-3-yl)-N-pyridin-4-yl-nicotinamide |
| "A48" | 2-Amino-5-(3,5-dimethyl-1H-pyrazol-4-yl)-N-pyridin-4-yl-nicotinamide |
| "A49" | 2-Amino-N-pyridin-4-yl-5-thiophen-3-yl-nicotinamide |
| "A50" | 2-Amino-5-(1-methyl-1H-pyrrol-2-yl)-N-pyridin-4-yl-nicotinamide |

| compound nr. | name |
|---|---|
| "A51" | 2-Amino-5-[1-(2-morpholin-4-yl-ethyl)-1H-pyrazol-4-yl]-N-pyridin-4-yl-nicotinamide |
| "A52" | 2-Amino-5-benzo[b]thiophen-2-yl-N-pyridin-4-yl-nicotinamide |
| "A53" | 5-(5-Acetyl-thiophen-2-yl)-2-amino-N-pyridin-4-yl-nicotinamide |
| "A54" | 2-Amino-5-(5-morpholin-4-ylmethyl-thiophen-2-yl)-N-pyridin-4-yl-nicotinamide |
| "A55" | 2-Amino-5-(1H-indol-2-yl)-N-pyridin-4-yl-nicotinamide |
| "A56" | 2-Amino-5-(1H-indol-3-yl)-N-pyridin-4-yl-nicotinamide |
| "A57" | 2-Amino-N-pyridin-4-yl-5-(1H-pyrrol-2-yl)-nicotinamide |
| "A58" | 2-Amino-5-(1H-imidazo[1,2-a]pyridin-2-yl)-N-pyridin-4-yl-nicotinamide |
| "A59" | 2-Amino-N-pyridin-4-yl-5-(1H-pyrrol-3-yl)-nicotinamide |
| "A60" | 2-Amino-5-benzofuran-3-yl-N-pyridin-4-yl-nicotinamide |
| "A61" | 2-Amino-5-(1-methyl-1H-pyrazol-4-yl)-N-pyridin-4-yl-nicotinamide | and pharmaceutically usable salts, tautomers and stereoisomers thereof, including mixtures thereof in all ratios.

31. Process for the preparation of compounds of the formula I according to claim 1 and pharmaceutically usable salts, tautomers and stereoisomers thereof, characterised in that:

a) a compound of the formula II

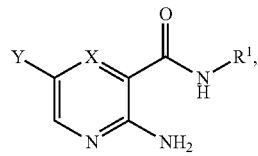

in which Y denotes an Br or I,
X and $R^1$ have the meanings indicated in claim 1,
is reacted with a compound of formula III

R-L                                III in which R has the meaning indicated in claim 1 and
L denotes a boronic acid or a boronic acid ester group,
or
b) a compound of the formula IV

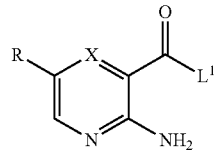

in which R and X have the meanings indicated in claim 1 and
$L^1$ denotes Cl, Br, I or a free or reactively functionally modified OH group,
is reacted with a compound of the formula V $R^1$—$NH_2$                        V in which $R^1$ has the meaning indicated in claim 1,
or
c) that it is liberated from one of its functional derivatives by treatment with a solvolysing or hydrolysing agent, and/or a base or acid of the formula I is converted into one of its salts.

32. Medicaments comprising: i) a compound of the formula I according to claim 1 and ii) pharmaceutically usable salts, tautomers and stereoisomers thereof, including mixtures thereof in all ratios.

33. A method for treating diseases selected from the group consisting of: cancer, septic shock, Primary open Angle Glaucoma (POAG), hyperplasia, rheumatoid arthritis, psoriasis, artherosclerosis, retinopathy, osteoarthritis, endometriosis, chronic inflammation, and neurodegenerative diseases comprising administering compounds of the formula I, according to claim 1, to a patient presenting at least one symptom of said diseases.

34. The method as claimed in claim 33 wherein said compounds further comprise: pharmaceutically usable salts, tautomers and stereoisomers thereof, including mixtures thereof in all ratios.

35. A method for the treatment of tumours comprising administering to a patient having a tumour the compounds of formula I according to claim 1 in combination with a compound from the group consisting of: oestrogen receptor modulator, androgen receptor modulator, retinoid receptor modulator, cytotoxic agent, antiproliferative agent, prenyl-protein transferase inhibitor, HMG-CoA reductase inhibitor, HIV protease inhibitor, reverse transcriptase inhibitor and angiogenesis inhibitors.

36. A method for the treatment of tumours comprising administering to a patient having a tumour the compounds of formula I according to claim 1 in combination with radiotherapy and a compound from the group consisting of: oestrogen receptor modulator, androgen receptor modulator, retinoid receptor modulator, cytotoxic agent, anti-proliferative agent, prenyl-protein transferase inhibitor, HMG-CoA reductase inhibitor, HIV protease inhibitor, reverse transcriptase inhibitor and angiogenesis inhibitors.

* * * * *

```
                        SEQUENCE LISTING

<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: Biotinylated I-kappa-B-alpha Peptide Substrate

<400> SEQUENCE: 1

Gly Leu Lys Lys Glu Arg Leu Leu Asp Asp Arg His Asp Ser Gly Leu
1               5                   10                  15

Asp Ser Met Lys Asp Glu Glu
            20

<210> SEQ ID NO 2
<211> LENGTH: 23
<212> TYPE: PRT
<213> ORGANISM: Artificial Sequence
<220> FEATURE:
<223> OTHER INFORMATION: Biotinylated TANK-binding kinase 1 (TBK1)
      substrate

<400> SEQUENCE: 2

Ala Lys Pro Lys Gly Asn Lys Asp Tyr His Leu Gln Thr Cys Cys Gly
1               5                   10                  15

Ser Leu Ala Tyr Arg Arg Arg
            20
```